(12) United States Patent
Sheetz et al.

(10) Patent No.: US 8,998,860 B2
(45) Date of Patent: Apr. 7, 2015

(54) SYSTEMS AND METHODS FOR IDENTIFYING AN ACCESS PORT

(75) Inventors: Kevin W. Sheetz, Sandy, UT (US); Bret Hamatake, Grantsville, UT (US); John G. Evans, South Jordan, UT (US); Richard P. Jenkins, Bluffdale, UT (US); Sean M. Worthen, West Jordan, UT (US); Loren R. Minert, South Jordan, UT (US); Alisha M. Hammond, West Jordan, UT (US); Charles L. Farnworth, Riverton, UT (US); Kelly B. Powers, North Salt Lake, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 28 days.

(21) Appl. No.: 13/524,712

(22) Filed: Jun. 15, 2012

(65) Prior Publication Data

US 2012/0259296 A1    Oct. 11, 2012

Related U.S. Application Data

(60) Division of application No. 12/610,084, filed on Oct. 30, 2009, now Pat. No. 8,202,259, and a continuation-in-part of application No. 12/420,028, filed on Apr. 7, 2009, now Pat. No. 7,947,022, which is (Continued)

(51) Int. Cl.
   *A61M 37/00*   (2006.01)
   *A61M 39/02*   (2006.01)

(52) U.S. Cl.
   CPC ....... *A61M 39/0208* (2013.01); *A61M 39/0247* (2013.01); *A61M 2039/0211* (2013.01);

(Continued)

(58) Field of Classification Search
   USPC .................................. 604/288.01, 288.02
   See application file for complete search history.

(56) References Cited

U.S. PATENT DOCUMENTS

| 445,896 A | 2/1891 | Kinsman |
|---|---|---|
| 546,440 A | 9/1895 | Tufts |

(Continued)

FOREIGN PATENT DOCUMENTS

| AU | 2008299945 A1 | 3/2009 |
|---|---|---|
| CA | 2663853 A1 | 4/2008 |

(Continued)

OTHER PUBLICATIONS

LAP-BAND® System Access Port Fill Guide I, "9.75/10.0 cm LAP-BAND System vs. 11 cm LAP-BAND System: For Product Manufactured Prior to Jul. 2001" BioEnterics Corporation.

(Continued)

*Primary Examiner* — Aarti B Berdichevsky
(74) *Attorney, Agent, or Firm* — Rutan & Tucker, LLP

(57) ABSTRACT

An access port for subcutaneous implantation is disclosed. Such an access port may comprise a body for capturing a septum for repeatedly inserting a needle therethrough into a cavity defined within the body. Further, the access port may include at least one feature structured and configured for identification of the access port subsequent to subcutaneous implantation. Methods of identifying a subcutaneously implanted access port are also disclosed. For example, a subcutaneously implanted access port may be provided and at least one feature of the subcutaneously implanted access port may be perceived. Further, the subcutaneously implanted access port may be identified in response to perceiving the at least one feature. In one embodiment, an identification feature is engraved or otherwise defined by the access port, so as to be visible after implantation via x-ray imaging technology.

19 Claims, 58 Drawing Sheets

Related U.S. Application Data a continuation-in-part of application No. 11/368,954, filed on Mar. 6, 2006, now Pat. No. 7,785,302.

(60) Provisional application No. 60/658,518, filed on Mar. 4, 2005, provisional application No. 61/110,507, filed on Oct. 31, 2008.

(52) U.S. Cl.
CPC .... *A61M2039/0238* (2013.01); *A61M 2205/32* (2013.01); *A61M 2205/582* (2013.01); *A61M 2205/6054* (2013.01)

(56) References Cited

U.S. PATENT DOCUMENTS

| | | |
|---|---|---|
| 574,387 A | 1/1897 | Buckler |
| 611,357 A | 9/1898 | Dembinski |
| 966,696 A | 8/1910 | Merrill |
| 1,713,267 A | 5/1929 | Crowley |
| 2,029,553 A | 2/1936 | Bartischi et al. |
| 2,433,480 A | 12/1947 | Rendich |
| 2,891,689 A | 6/1959 | Gould |
| D198,453 S | 6/1964 | Weichselbaum |
| 3,159,175 A | 12/1964 | Macmillan |
| 3,293,663 A | 12/1966 | Cronin |
| 3,341,417 A | 9/1967 | Sinaiko |
| 3,477,438 A | 11/1969 | Allen et al. |
| 3,518,428 A | 6/1970 | Ring |
| 3,525,357 A | 8/1970 | Koreski |
| 3,529,633 A | 9/1970 | Vailancourt |
| 3,540,670 A | 11/1970 | Rissberger |
| 3,541,438 A | 11/1970 | Nelsen et al. |
| 3,643,358 A | 2/1972 | Morderosian |
| 3,669,323 A | 6/1972 | Harker et al. |
| 3,674,183 A | 7/1972 | Venable et al. |
| 3,811,466 A | 5/1974 | Ohringer |
| 3,829,904 A | 8/1974 | Ling et al. |
| 3,831,549 A | 8/1974 | Parsons |
| 3,831,583 A | 8/1974 | Edmunds, Jr. et al. |
| 3,840,009 A | 10/1974 | Michaels et al. |
| 3,853,127 A | 12/1974 | Spademan |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 3,955,594 A | 5/1976 | Snow |
| 3,971,376 A | 7/1976 | Wichterle |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,143,853 A | 3/1979 | Abramson |
| 4,168,586 A | 9/1979 | Samis |
| 4,181,132 A | 1/1980 | Parks |
| 4,190,040 A | 2/1980 | Schulte |
| 4,190,057 A | 2/1980 | Hill et al. |
| 4,194,122 A | 3/1980 | Mitchell et al. |
| 4,196,731 A | 4/1980 | Laurin et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,447,237 A | 5/1984 | Frisch et al. |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,479,798 A | 10/1984 | Parks |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,046 A | 12/1985 | Groshong et al. |
| 4,560,375 A | 12/1985 | Schulte et al. |
| 4,569,675 A | 2/1986 | Prosl et al. |
| 4,571,749 A | 2/1986 | Fischell |
| 4,576,595 A | 3/1986 | Aas et al. |
| 4,610,665 A | 9/1986 | Matsumoto et al. |
| 4,612,877 A | 9/1986 | Hayes et al. |
| 4,626,244 A | 12/1986 | Reinicke |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stober et al. |
| 4,707,389 A | 11/1987 | Ward |
| 4,710,174 A | 12/1987 | Moden et al. |
| 4,718,894 A | 1/1988 | Lazorthes |
| 4,723,947 A | 2/1988 | Konopka |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,784,646 A | 11/1988 | Feingold |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |
| 4,904,241 A | 2/1990 | Bark |
| 4,905,709 A | 3/1990 | Bieganski et al. |
| 4,908,029 A | 3/1990 | Bark et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,961,267 A | 10/1990 | Herzog |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |

(56) References Cited

U.S. PATENT DOCUMENTS

| | | |
|---|---|---|
| 5,009,391 A | 4/1991 | Steigerwald |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,053,013 A | 10/1991 | Ensminger et al. |
| 5,059,186 A | 10/1991 | Yamamoto et al. |
| 5,069,206 A | 12/1991 | Crosbie |
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |
| 5,108,317 A | 4/1992 | Beinhaur et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,169,393 A | 12/1992 | Moorehead et al. |
| 5,171,228 A | 12/1992 | McDonald |
| 5,176,653 A | 1/1993 | Metals |
| 5,176,662 A | 1/1993 | Bartholomew et al. |
| 5,178,612 A | 1/1993 | Fenton, Jr. |
| 5,185,003 A | 2/1993 | Brethauer |
| 5,189,690 A | 2/1993 | Samuel |
| 5,193,106 A | 3/1993 | DeSena |
| 5,195,122 A | 3/1993 | Fabian |
| 5,195,123 A | 3/1993 | Clement |
| 5,201,715 A | 4/1993 | Masters |
| 5,201,722 A | 4/1993 | Moorehead et al. |
| 5,203,771 A | 4/1993 | Melker et al. |
| 5,203,777 A | 4/1993 | Lee |
| 5,205,834 A | 4/1993 | Moorehead et al. |
| 5,213,574 A | 5/1993 | Tucker |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,242,415 A | 9/1993 | Kantrowitz et al. |
| 5,246,462 A | 9/1993 | Bekki et al. |
| 5,249,598 A | 10/1993 | Schmidt |
| 5,263,930 A | 11/1993 | Ensminger |
| 5,281,205 A | 1/1994 | McPherson |
| 5,290,263 A | 3/1994 | Wigness et al. |
| 5,295,658 A | 3/1994 | Atkinson et al. |
| 5,299,253 A | 3/1994 | Wessels |
| 5,300,048 A | 4/1994 | Drewes, Jr. et al. |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,328,480 A | 7/1994 | Melker et al. |
| 5,332,398 A | 7/1994 | Miller et al. |
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard et al. |
| 5,383,223 A | 1/1995 | Inokuchi |
| 5,383,233 A | 1/1995 | Russell |
| 5,383,585 A | 1/1995 | Weiss |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,396,925 A | 3/1995 | Poli |
| 5,397,329 A | 3/1995 | Allen |
| 5,399,168 A | 3/1995 | Wadsworth, Jr. et al. |
| 5,405,402 A | 4/1995 | Dye et al. |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,453,097 A | 9/1995 | Paradis |
| 5,456,698 A | 10/1995 | Byland et al. |
| 5,476,451 A | 12/1995 | Ensminger et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,542,923 A | 8/1996 | Ensminger et al. |
| 5,545,143 A | 8/1996 | Fischell |
| 5,554,117 A | 9/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,575,770 A | 11/1996 | Melsky et al. |
| 5,593,434 A | 1/1997 | Williams |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| RE35,601 E | 9/1997 | Eckenhoff |
| 5,662,600 A | 9/1997 | Watson et al. |
| 5,662,612 A | 9/1997 | Niehoff |
| 5,662,616 A | 9/1997 | Bousquet |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,707,357 A | 1/1998 | Mikhail et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,797,886 A | 8/1998 | Roth et al. |
| 5,810,789 A | 9/1998 | Powers et al. |
| 5,814,016 A | 9/1998 | Valley et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |

(56) References Cited

U.S. PATENT DOCUMENTS

| | | |
|---|---|---|
| 5,840,063 A | 11/1998 | Flaherty |
| 5,843,069 A | 12/1998 | Butler et al. |
| 5,848,989 A | 12/1998 | Villani |
| 5,853,394 A | 12/1998 | Tolkoff et al. |
| 5,868,702 A | 2/1999 | Stevens et al. |
| 5,879,322 A | 3/1999 | Lattin et al. |
| 5,882,341 A | 3/1999 | Bousquet |
| 5,882,353 A | 3/1999 | VanBeek et al. |
| 5,895,424 A | 4/1999 | Steele, Sr. et al. |
| 5,897,528 A | 4/1999 | Schultz |
| 5,899,856 A | 5/1999 | Schoendorfer et al. |
| 5,904,934 A | 5/1999 | Maruyama et al. |
| 5,906,596 A | 5/1999 | Tallarida |
| 5,908,413 A | 6/1999 | Lange et al. |
| 5,908,414 A | 6/1999 | Otto et al. |
| 5,911,706 A | 6/1999 | Estabrook et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,927,345 A | 7/1999 | Samson |
| 5,928,197 A | 7/1999 | Niehoff |
| 5,928,744 A | 7/1999 | Heilmann et al. |
| 5,931,829 A | 8/1999 | Burbank et al. |
| 5,941,856 A | 8/1999 | Kovacs et al. |
| 5,944,023 A | 8/1999 | Johnson et al. |
| 5,944,688 A | 8/1999 | Lois |
| 5,944,698 A | 8/1999 | Fischer et al. |
| 5,944,712 A | 8/1999 | Frassica et al. |
| D413,672 S | 9/1999 | Fogarty |
| 5,947,953 A | 9/1999 | Ash et al. |
| 5,951,512 A | 9/1999 | Dalton |
| 5,951,522 A | 9/1999 | Rosato et al. |
| 5,951,929 A | 9/1999 | Wilson |
| 5,954,687 A | 9/1999 | Baudino |
| 5,954,691 A | 9/1999 | Prosl |
| 5,957,890 A | 9/1999 | Mann et al. |
| 5,961,497 A | 10/1999 | Larkin |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,989,641 A | 11/1999 | Oulie |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,056,717 A | 5/2000 | Finch et al. |
| 6,077,756 A | 6/2000 | Lin et al. |
| 6,086,555 A | 7/2000 | Eliasen et al. |
| 6,090,066 A | 7/2000 | Schnell |
| 6,099,508 A | 8/2000 | Bousquet |
| 6,102,884 A | 8/2000 | Squitieri |
| 6,113,572 A | 9/2000 | Gailey et al. |
| 6,120,492 A | 9/2000 | Finch et al. |
| 6,152,909 A | 11/2000 | Bagaoisan et al. |
| 6,161,033 A | 12/2000 | Kuhn |
| 6,171,198 B1 | 1/2001 | Troncoso et al. |
| 6,171,298 B1 | 1/2001 | Matsuura et al. |
| 6,186,982 B1 | 2/2001 | Gross et al. |
| 6,190,352 B1 | 2/2001 | Haarala et al. |
| 6,193,684 B1 | 2/2001 | Burbank et al. |
| 6,198,807 B1 | 3/2001 | DeSena |
| 6,200,338 B1 | 3/2001 | Solomon et al. |
| 6,203,570 B1 | 3/2001 | Baeke |
| 6,210,366 B1 | 4/2001 | Sanfilippo, II |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,261,259 B1 | 7/2001 | Bell |
| 6,269,148 B1 | 7/2001 | Jessop et al. |
| 6,272,370 B1 | 8/2001 | Gillies et al. |
| 6,287,293 B1 | 9/2001 | Jones et al. |
| 6,290,677 B1 | 9/2001 | Arai et al. |
| 6,305,413 B1 | 10/2001 | Fischer et al. |
| 6,306,124 B1 | 10/2001 | Jones et al. |
| D450,115 S | 11/2001 | Bertheas |
| 6,332,874 B1 | 12/2001 | Eliasen et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,473,638 B2 | 10/2002 | Ferek-Petric |
| 6,475,516 B2 | 11/2002 | DiCosmo et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,572,583 B1 | 6/2003 | Olsen et al. |
| 6,582,418 B1 | 6/2003 | Verbeek et al. |
| 6,592,571 B1 | 7/2003 | Verbeek et al. |
| 6,610,031 B1 | 8/2003 | Chin |
| 6,613,002 B1 | 9/2003 | Clark et al. |
| 6,613,662 B2 | 9/2003 | Wark et al. |
| 6,626,936 B2 | 9/2003 | Stinson |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,663,646 B1 | 12/2003 | Shah |
| 6,676,633 B2 | 1/2004 | Smith et al. |
| 6,697,664 B2 | 2/2004 | Kienzle, III et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,726,063 B2 | 4/2004 | Stull et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,808,738 B2 | 10/2004 | DiTizio et al. |
| 6,826,257 B2 | 11/2004 | Sayre et al. |
| 6,852,106 B2 | 2/2005 | Watson et al. |
| 6,856,055 B2 | 2/2005 | Michaels et al. |
| 6,878,136 B2 | 4/2005 | Fleury et al. |
| 6,878,137 B2 | 4/2005 | Benchetrit |
| 6,929,631 B1 | 8/2005 | Brugger et al. |
| 6,949,084 B2 | 9/2005 | Marggi et al. |
| 6,962,577 B2 | 11/2005 | Tallarida et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| 7,033,339 B1 | 4/2006 | Lynn |
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz |
| 7,074,232 B2 | 7/2006 | Kanner et al. |
| 7,076,305 B2 | 7/2006 | Imran et al. |
| 7,083,593 B2 | 8/2006 | Stultz |
| 7,108,686 B2 | 9/2006 | Burke et al. |
| 7,123,690 B1 | 10/2006 | Brown et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,191,011 B2 | 3/2007 | Cantlon |

(56) References Cited

U.S. PATENT DOCUMENTS

| | | |
|---|---|---|
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,235,067 B2 | 6/2007 | Morris et al. |
| D546,440 S | 7/2007 | Burnside |
| 7,242,982 B2 | 7/2007 | Singhal et al. |
| 7,248,668 B2 | 7/2007 | Galkin |
| 7,252,469 B2 | 8/2007 | Zaluzec et al. |
| 7,252,649 B2 | 8/2007 | Sherry |
| 7,261,705 B2 | 8/2007 | Edoga et al. |
| D554,253 S | 10/2007 | Kornerup |
| 7,275,682 B2 | 10/2007 | Excoffier et al. |
| 7,276,075 B1 | 10/2007 | Callas et al. |
| D556,153 S | 11/2007 | Burnside |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,442 S | 2/2008 | Blateri |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| 7,485,148 B2 | 2/2009 | Wozencroft et al. |
| 7,552,853 B2 | 6/2009 | Mas et al. |
| 7,553,298 B2 | 6/2009 | Hunt et al. |
| D595,892 S | 7/2009 | Smith et al. |
| 7,563,025 B2 | 7/2009 | Kay |
| D612,479 S | 3/2010 | Zawacki et al. |
| 7,713,251 B2 | 5/2010 | Tallarida et al. |
| 7,785,302 B2 | 8/2010 | Powers |
| 7,803,143 B2 | 9/2010 | Tallarida et al. |
| 7,806,888 B2 | 10/2010 | Frassica |
| 7,811,266 B2 | 10/2010 | Eliasen |
| D629,503 S | 12/2010 | Caffey et al. |
| D634,840 S | 3/2011 | Lombardi, III et al. |
| 7,909,804 B2 | 3/2011 | Stats |
| 7,947,022 B2 * | 5/2011 | Amin et al. ............... 604/288.02 |
| 7,959,615 B2 | 6/2011 | Stats et al. |
| 8,021,324 B2 * | 9/2011 | Bizup et al. ................. 604/88 |
| 8,025,639 B2 | 9/2011 | Powers et al. |
| 8,029,482 B2 * | 10/2011 | Maniar et al. ............ 604/288.02 |
| 8,075,536 B2 | 12/2011 | Gray et al. |
| 8,092,435 B2 * | 1/2012 | Beling et al. ............. 604/288.02 |
| 8,147,455 B2 | 4/2012 | Butts et al. |
| 8,172,894 B2 | 5/2012 | Schmid et al. |
| 8,172,896 B2 | 5/2012 | McNamara et al. |
| 8,177,762 B2 | 5/2012 | Beasley et al. |
| 8,182,453 B2 | 5/2012 | Eliasen |
| 8,197,454 B2 | 6/2012 | Mann et al. |
| 8,202,259 B2 | 6/2012 | Evans et al. |
| 8,257,325 B2 * | 9/2012 | Schweikert et al. ..... 604/288.01 |
| D676,955 S | 2/2013 | Orome |
| 8,377,034 B2 | 2/2013 | Tallarida et al. |
| 8,382,723 B2 | 2/2013 | Powers et al. |
| 8,382,724 B2 * | 2/2013 | Maniar et al. ............ 604/288.02 |
| 8,409,153 B2 | 4/2013 | Tallarida et al. |
| 8,475,417 B2 | 7/2013 | Powers et al. |
| 8,545,460 B2 | 10/2013 | Beasley et al. |
| 8,585,663 B2 | 11/2013 | Powers et al. |
| 8,603,052 B2 | 12/2013 | Powers et al. |
| 8,608,713 B2 | 12/2013 | Beasley et al. |
| 8,641,676 B2 | 2/2014 | Butts et al. |
| 8,641,688 B2 | 2/2014 | Powers et al. |
| 8,805,478 B2 | 8/2014 | Powers et al. |
| 2001/0016717 A1 | 8/2001 | Haarala et al. |
| 2001/0047165 A1 | 11/2001 | Makower et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2002/0013557 A1 | 1/2002 | Sherry |
| 2002/0052576 A1 | 5/2002 | Massengale |
| 2002/0055715 A1 | 5/2002 | Young et al. |
| 2002/0095205 A1 | 7/2002 | Edwin et al. |
| 2002/0121530 A1 | 9/2002 | Socier |
| 2002/0138068 A1 | 9/2002 | Watson et al. |
| 2002/0169418 A1 | 11/2002 | Menzi et al. |
| 2002/0173769 A1 | 11/2002 | Gray et al. |
| 2002/0173772 A1 | 11/2002 | Olsen |
| 2002/0183846 A1 | 12/2002 | Kuslich et al. |
| 2002/0188282 A1 | 12/2002 | Greenberg |
| 2003/0028173 A1 | 2/2003 | Forsberg |
| 2003/0093029 A1 | 5/2003 | McGuckin et al. |
| 2003/0109856 A1 | 6/2003 | Sherry |
| 2003/0130627 A1 | 7/2003 | Smith et al. |
| 2003/0139812 A1 | 7/2003 | Garcia et al. |
| 2003/0141477 A1 | 7/2003 | Miller |
| 2003/0181878 A1 | 9/2003 | Tallarida et al. |
| 2003/0191452 A1 | 10/2003 | Meglin et al. |
| 2003/0208184 A1 | 11/2003 | Burke et al. |
| 2003/0216694 A1 | 11/2003 | Tollini |
| 2003/0217659 A1 | 11/2003 | Yamamoto et al. |
| 2004/0006316 A1 | 1/2004 | Patton |
| 2004/0020462 A1 | 2/2004 | Sauler et al. |
| 2004/0020492 A1 | 2/2004 | Dubrul et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0078000 A1 | 4/2004 | Borchard et al. |
| 2004/0086568 A1 | 5/2004 | Ditizio et al. |
| 2004/0087877 A1 | 5/2004 | Besz et al. |
| 2004/0087885 A1 | 5/2004 | Kawano et al. |
| 2004/0106878 A1 | 6/2004 | Skujins et al. |
| 2004/0106891 A1 | 6/2004 | Langan et al. |
| 2004/0106942 A1 | 6/2004 | Taylor et al. |
| 2004/0133173 A1 | 7/2004 | Edoga et al. |
| 2004/0156472 A1 | 8/2004 | Galkin |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0186444 A1 | 9/2004 | Daly et al. |
| 2004/0199129 A1 | 10/2004 | DiMatteo |
| 2004/0199220 A1 | 10/2004 | Cantlon |
| 2004/0204692 A1 | 10/2004 | Eliasen |
| 2004/0204759 A1 | 10/2004 | Blom et al. |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0010176 A1 | 1/2005 | Dikeman et al. |
| 2005/0010286 A1 | 1/2005 | Vijay |
| 2005/0027234 A1 | 2/2005 | Waggoner et al. |
| 2005/0027261 A1 | 2/2005 | Weaver et al. |
| 2005/0038390 A1 | 2/2005 | Fago et al. |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0080401 A1 | 4/2005 | Peavey |
| 2005/0085778 A1 | 4/2005 | Parks |
| 2005/0113806 A1 | 5/2005 | De Carvalho et al. |
| 2005/0124980 A1 | 6/2005 | Sanders |
| 2005/0131352 A1 | 6/2005 | Conlon et al. |
| 2005/0148866 A1 | 7/2005 | Gunderson |
| 2005/0148869 A1 | 7/2005 | Masuda |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |

(56) References Cited

U.S. PATENT DOCUMENTS

| | | |
|---|---|---|
| 2005/0182857 A1 | 8/2005 | Kong |
| 2005/0209573 A1 | 9/2005 | Brugger et al. |
| 2005/0215874 A1 | 9/2005 | Wang et al. |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0171980 A1 | 8/2006 | Helmus et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0224128 A1 | 10/2006 | Lurvey et al. |
| 2006/0224129 A1 | 10/2006 | Beasley et al. |
| 2006/0224235 A1 | 10/2006 | Rucker |
| 2006/0241465 A1 | 10/2006 | Huennekens et al. |
| 2006/0247584 A1 | 11/2006 | Sheetz et al. |
| 2006/0253076 A1 | 11/2006 | Butts et al. |
| 2006/0264898 A1 | 11/2006 | Beasley et al. |
| 2007/0003603 A1 | 1/2007 | Karandikar et al. |
| 2007/0007839 A1 | 1/2007 | Lin |
| 2007/0010881 A1 | 1/2007 | Soye et al. |
| 2007/0016162 A1 | 1/2007 | Burbank et al. |
| 2007/0049806 A1 | 3/2007 | Adams et al. |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083111 A1 | 4/2007 | Hossack et al. |
| 2007/0083156 A1 | 4/2007 | Muto et al. |
| 2007/0100302 A1 | 5/2007 | Dicarlo et al. |
| 2007/0112332 A1 | 5/2007 | Harding et al. |
| 2007/0120683 A1 | 5/2007 | Flippen et al. |
| 2007/0135775 A1 | 6/2007 | Edoga et al. |
| 2007/0149920 A1 | 6/2007 | Michels et al. |
| 2007/0149921 A1 | 6/2007 | Michels et al. |
| 2007/0149947 A1 | 6/2007 | Byrum |
| 2007/0161958 A1 | 7/2007 | Glenn |
| 2007/0179456 A1 | 8/2007 | Glenn |
| 2007/0185462 A1 | 8/2007 | Byrum |
| 2007/0191773 A1 | 8/2007 | Wojcik |
| 2007/0207335 A1 | 9/2007 | Karandikar et al. |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0276355 A1 | 11/2007 | Nielsen et al. |
| 2007/0282308 A1 | 12/2007 | Bell |
| 2007/0293800 A1 | 12/2007 | McMaken et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0108949 A1 | 5/2008 | Beasley et al. |
| 2008/0114308 A1 | 5/2008 | di Palma et al. |
| 2008/0133265 A1 | 6/2008 | Silkaitis et al. |
| 2008/0137923 A1 | 6/2008 | Spahn |
| 2008/0138387 A1 | 6/2008 | Machiraju |
| 2008/0140025 A1 | 6/2008 | Sheetz et al. |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |
| 2009/0156928 A1 | 6/2009 | Evans et al. |
| 2009/0204072 A1 | 8/2009 | Amin et al. |
| 2009/0204074 A1 | 8/2009 | Powers et al. |
| 2009/0216216 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2009/0227964 A1 | 9/2009 | DiCarlo et al. |
| 2009/0264901 A1 | 10/2009 | Franklin et al. |
| 2009/0322541 A1 | 12/2009 | Jones et al. |
| 2010/0010339 A1 | 1/2010 | Smith et al. |
| 2010/0042073 A1 | 2/2010 | Oster et al. |
| 2010/0063451 A1 | 3/2010 | Gray et al. |
| 2010/0069743 A1 | 3/2010 | Sheetz et al. |
| 2010/0121283 A1 | 5/2010 | Hamatake et al. |
| 2010/0211026 A2 | 8/2010 | Sheetz et al. |
| 2010/0268165 A1 | 10/2010 | Maniar et al. |
| 2010/0268174 A1 | 10/2010 | Steinke et al. |
| 2011/0021922 A1 | 1/2011 | Berard-Anderson et al. |
| 2011/0092921 A1 | 4/2011 | Beling et al. |
| 2011/0118677 A1 | 5/2011 | Wiley et al. |
| 2011/0183712 A1 | 7/2011 | Eckstein et al. |
| 2011/0213700 A1 | 9/2011 | Sant'Anselmo |
| 2011/0275930 A1 | 11/2011 | Jho et al. |
| 2011/0276015 A1 | 11/2011 | Powers et al. |
| 2011/0288502 A1 | 11/2011 | Hibdon et al. |
| 2011/0311337 A1 | 12/2011 | Amin et al. |
| 2012/0018073 A1 | 1/2012 | Maniar et al. |
| 2012/0065622 A1 | 3/2012 | Cornish et al. |
| 2012/0078201 A1 | 3/2012 | Mikami |
| 2012/0191071 A1 | 7/2012 | Butts et al. |
| 2012/0226244 A1 | 9/2012 | Beasley et al. |
| 2012/0302969 A1 | 11/2012 | Wiley et al. |
| 2013/0165773 A1 | 6/2013 | Powers et al. |
| 2013/0172733 A1 | 7/2013 | Maniar et al. |
| 2013/0225990 A1 | 8/2013 | Powers et al. |
| 2013/0225991 A1 | 8/2013 | Powers |
| 2013/0245574 A1 | 9/2013 | Powers et al. |
| 2013/0338494 A1 | 12/2013 | Wiley et al. |
| 2014/0081219 A1 | 3/2014 | Powers et al. |
| 2014/0100534 A1 | 4/2014 | Beasley et al. |
| 2014/0107619 A1 | 4/2014 | Butts et al. |
| 2014/0330118 A1 | 11/2014 | Powers et al. |

FOREIGN PATENT DOCUMENTS

| | | | |
|---|---|---|---|
| CA | 2692142 | A1 | 12/2008 |
| CA | 2693972 | A1 | 1/2009 |
| CN | 102421469 | A | 4/2012 |
| CN | 102612343 | A | 7/2012 |
| DE | 3618390 | C1 | 11/1987 |
| DE | 3720414 | A1 | 12/1987 |
| DE | 10346470 | A1 | 5/2005 |
| EP | 0128525 | A2 | 12/1984 |
| EP | 0134745 | A1 | 3/1985 |
| EP | 0343910 | A2 | 11/1989 |
| EP | 0366814 | A1 | 5/1990 |
| EP | 0239244 | | 9/1991 |
| EP | 0534782 | A1 | 3/1993 |
| EP | 0619101 | A1 | 10/1994 |
| EP | 1635899 | A2 | 3/2006 |
| EP | 2006019101 | A2 | 12/2006 |
| EP | 1858565 | A1 | 11/2007 |
| EP | 1874393 | A1 | 1/2008 |
| EP | 1896117 | A2 | 3/2008 |
| EP | 1998842 | A2 | 12/2008 |
| EP | 2004272 | A2 | 12/2008 |

(56) References Cited

FOREIGN PATENT DOCUMENTS

| | | |
|---|---|---|
| EP | 2018209 A2 | 1/2009 |
| EP | 2081634 A1 | 7/2009 |
| EP | 2164559 A1 | 3/2010 |
| EP | 2167182 A1 | 3/2010 |
| EP | 2180915 A1 | 5/2010 |
| EP | 2190517 A1 | 6/2010 |
| EP | 2308547 A2 | 4/2011 |
| EP | 2320974 A1 | 5/2011 |
| EP | 2324878 A2 | 5/2011 |
| EP | 2324879 A2 | 5/2011 |
| EP | 2324880 A2 | 5/2011 |
| EP | 2365838 A1 | 9/2011 |
| EP | 2571563 A1 | 3/2013 |
| EP | 2601999 A1 | 6/2013 |
| EP | 2324879 B1 | 1/2014 |
| FR | 1509165 A | 1/1968 |
| FR | 2508008 A1 | 12/1982 |
| FR | 2809315 A1 | 11/2001 |
| GB | 178998 A | 5/1922 |
| GB | 749942 A | 6/1956 |
| GB | 966137 A | 8/1964 |
| GB | 1559140 A | 1/1980 |
| GB | 2102398 A | 2/1983 |
| GB | 2191701 A | 12/1987 |
| GB | 2350352 A | 11/2000 |
| JP | 62155857 A | 7/1987 |
| JP | 62281966 A | 12/1987 |
| JP | 6296633 A | 10/1994 |
| JP | 2000-079168 A | 3/2000 |
| JP | 2002500076 A | 1/2002 |
| JP | 2003-510136 A | 3/2003 |
| JP | 2004-350937 A | 12/2004 |
| JP | 2006025948 A | 2/2006 |
| JP | 2012-523284 A | 10/2012 |
| JP | 2013-510652 | 3/2013 |
| JP | 2013-526376 A | 6/2013 |
| WO | 8600213 A1 | 1/1986 |
| WO | 8911309 A1 | 11/1989 |
| WO | 9001958 A1 | 3/1990 |
| WO | 9206732 A1 | 4/1992 |
| WO | 9300945 A1 | 1/1993 |
| WO | 9305730 A1 | 4/1993 |
| WO | 9308986 A1 | 5/1993 |
| WO | 9515194 | 6/1995 |
| WO | 9516480 A1 | 6/1995 |
| WO | 9701370 A1 | 1/1997 |
| WO | 9706845 A1 | 2/1997 |
| WO | 9711726 A1 | 4/1997 |
| WO | 9723255 A1 | 7/1997 |
| WO | 9726931 A1 | 7/1997 |
| WO | 9817337 A1 | 4/1998 |
| WO | 9818506 A1 | 5/1998 |
| WO | 9831417 A2 | 7/1998 |
| WO | 9934859 A1 | 7/1999 |
| WO | 9938553 A1 | 8/1999 |
| WO | 9942166 A1 | 8/1999 |
| WO | 0012171 A1 | 3/2000 |
| WO | 0016844 A1 | 3/2000 |
| WO | 0033901 A1 | 6/2000 |
| WO | 0123023 A1 | 4/2001 |
| WO | 0160444 A1 | 8/2001 |
| WO | 0247549 A1 | 6/2002 |
| WO | 03084832 A1 | 10/2003 |
| WO | 03090509 A2 | 11/2003 |
| WO | 2004004800 A2 | 1/2004 |
| WO | 2004028611 A1 | 4/2004 |
| WO | 2004071555 A2 | 8/2004 |
| WO | 2004091434 A2 | 10/2004 |
| WO | 2005037055 A2 | 4/2005 |
| WO | 2005068009 A1 | 7/2005 |
| WO | 2006078915 A2 | 7/2006 |
| WO | 2006096686 A1 | 9/2006 |
| WO | 2006116438 A2 | 11/2006 |
| WO | 2006116613 A1 | 11/2006 |
| WO | 2006130133 A1 | 12/2006 |
| WO | 2006134100 A1 | 12/2006 |
| WO | 2007041471 A2 | 4/2007 |
| WO | 2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008008126 A2 | 1/2008 |
| WO | 2008019236 A1 | 2/2008 |
| WO | 2008048361 A1 | 4/2008 |
| WO | 2008062173 A1 | 5/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |
| WO | 2009012385 A1 | 1/2009 |
| WO | 2009012395 A1 | 1/2009 |
| WO | 2009035582 A1 | 3/2009 |
| WO | 2009046439 A2 | 4/2009 |
| WO | 2009046725 A1 | 4/2009 |
| WO | 2009108669 A1 | 9/2009 |
| WO | 2010030351 A1 | 3/2010 |
| WO | 2010062633 A1 | 6/2010 |
| WO | 2010118144 A1 | 10/2010 |
| WO | 2011046604 A2 | 4/2011 |
| WO | 2011062750 A1 | 5/2011 |
| WO | 2011146649 A1 | 11/2011 |
| WO | 2014031763 A2 | 2/2014 |

OTHER PUBLICATIONS

Leslie et al., "A New Simple Power Injector," Am J Roentgenol 128: 381-384, Mar. 1977.

MedComp "PortCT Technology", display at SIR Conference (Mar. 2006), Toronto, Canada.

Navilyst Medical, Implantable Ports with PASV® Valve Technology, Product Overview, <<http://www.navilystmedical.com/Products/index.cfm/9>> last accessed Jun. 4, 2012.

Nucleus Cochlear Implant Systems; User Manual for the ESPrit 3G speech processor and accessories, Issue 2, Dec. 2001 http://www.cochlearamericas.com/PDFs/UserManualSprint.pdf.

Oct. 22, 2009 Declaration of Kelly Christian, Director of Product Development at BARD Access Systems, Inc, in support of and depicting a product on the market by Quinton Company approximately ten years prior to Oct. 22, 2009, 1 page.

PCT/US1999/028695 filed Dec. 3, 1999 International Preliminary Examination Report dated Apr. 21, 2001.

PCT/US1999/028695 filed Dec. 3, 1999 Search Report dated Apr. 11, 2000.

PCT/US2006/008022 filed Mar. 6, 2006 International Preliminary Report on Patentability dated Sep. 12, 2007.

PCT/US2006/008022 filed Mar. 6, 2006 Search Report dated Jul. 5, 2006.

PCT/US2006/008022 filed Mar. 6, 2006 Written Opinion dated Apr. 9, 2007.

PCT/US2006/008022 filed Mar. 6, 2006 Written Opinion dated Jul. 5, 2006.

PCT/US2006/015695 filed Apr. 25, 2006 Partial Search Report dated Sep. 29, 2006.

PCT/US2006/015695 filed Apr. 25, 2006 Search Report dated Jan. 11, 2007.

PCT/US2006/015695 filed Apr. 25, 2006 Written Opinion dated Jan. 11, 2007.

PCT/US2006/016056 filed Apr. 27, 2006 International Preliminary Report on Patentability dated Oct. 30, 2007.

PCT/US2006/016056 filed Apr. 27, 2006 Search Report dated Sep. 20, 2006.

PCT/US2006/016056 filed Apr. 27, 2006 Written Opinion dated Oct. 27, 2007.

PCT/US2006/016056 filed Apr. 27, 2006 Written Opinion dated Sep. 20, 2006.

PCT/US2006/049007 filed Dec. 21, 2006 International Preliminary Report on Patentability dated Jul. 1, 2008.

(56) References Cited

OTHER PUBLICATIONS

PCT/US2006/049007 filed Dec. 21, 2006 Search Report dated Oct. 1, 2007.
PCT/US2006/049007 filed Dec. 21, 2006 Written Opinion dated Oct. 1, 2007.
PCT/US2007/006776 filed Mar. 19, 2007 International Preliminary Report on Patentability dated Jan. 2, 2009.
PCT/US2007/006776 filed Mar. 19, 2007 Search Report, dated Dec. 18, 2007.
PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Oct. 29, 2008.
PCT/US2007/011015 filed May 7, 2007 Search Report dated Jun. 10, 2008.
PCT/US2007/011456 filed May 11, 2007 Search Report dated Aug. 28, 2008.
PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
PCT/US2008/067679 filed Jun. 20, 2008 Search Report dated Sep. 30, 2008.
PCT/US2008/067679 filed Jun. 20, 2008 Written Opinion mailed on Sep. 30, 2008.
PCT/US2008/070330 filed Jul. 17, 2008 Search Report dated Dec. 1, 2008.
PCT/US2008/070330 filed Jul. 17, 2008 Written Opinion dated Dec. 1, 2008.
PCT/US2008/070345 filed Jul. 17, 2008 Search Report mailed on Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/062854 filed Oct. 30, 2009 International Preliminary Report on Patentability dated May 5, 2011.
PCT/US2009/062854 filed Oct. 30, 2009 International Search Report dated Dec. 10, 2009.
PCT/US2009/062854 filed Oct. 30, 2009 Search Report dated Dec. 23, 2009.
PCT/US2009/062854 filed Oct. 30, 2009 Written Opinion dated Dec. 10, 2009.
PCT/US2009/062854 filed Oct. 30, 2009 Written Opinion dated Dec. 23, 2009.
PCT/US2010/030256 filed Apr. 7, 2010 Search Report and Written Opinion dated Jun. 4, 2010.
PCT/US2010/030256 filed Apr. 7, 2010 Search Report dated Jun. 4, 2010.
U.S. Appl. No. 12/796,133, filed Jun. 8, 2010 Non-Final Office Action dated Feb. 17, 2011.
U.S. Appl. No. 12/796,133, filed Jun. 8, 2010 Notice of Allowance dated Jun. 9, 2011.
U.S. Appl. No. 12/419,854, filed Apr. 7, 2009 Non-Final Office Action dated Aug. 5, 2011.
U.S. Appl. No. 13/113,834, filed May 23, 2011 Non-Final Office Action dated Jul. 17, 2012.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.
U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.
U.S. Appl. No. 29/284,456, filed Sep. 7, 2007, titled Implantable Port Device, listing John A. Zawacki and Annemarie Boswell as inventors.
Vergara, et al., "Adverse Reactions to Contrast Medica in CT: Effects of Temperature and Ionic Property." Radiology, vol. 199, No. 2, May 1996.
Vogelzang, Robert L., "Power Injection Through Central Venous Catheters: Physiological and Hemodynamic Considerations." The McGaw Medical Center of Northwestern University, Feinberg School of Medicine. Jun. 23, 2004.
Wells, S. "Venous Access in Oncology and Haematology Patients: Part One." Nursing Standard, vol. 22, No. 52, pp. 39-46, Sep. 3, 2008.
Wikipedia, "Port Catheter", Dec. 15, 2011.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.
U.S. Appl. No. 13/159,230, filed Jun. 13, 2011 Notice of Allowance dated Aug. 1, 2012.
U.S. Appl. No. 13/250,909, filed Sep. 30, 2011 Notice of Allowance dated Aug. 6, 2012.
U.S. Appl. No. 11/368,954, filed Mar. 6, 2006 Final Office Action dated Jan. 27, 2010.
U.S. Appl. No. 11/368,954, filed Mar. 6, 2006 Supplemental Non-final Office Action mailed Oct. 2, 2009.
U.S. Appl. No. 11/380,124, filed Apr. 25, 2006 Final Office Action dated Aug. 13, 2010.
U.S. Appl. No. 11/380,124, filed Apr. 25, 2006 Final Office Action dated Oct. 20, 2011.
U.S. Appl. No. 11/380,124, filed Apr. 25, 2006 Final Office Action dated Sep. 21, 2009.
U.S. Appl. No. 11/380,124, filed Apr. 25, 2006 Non-Final Office Action dated Apr. 26, 2010.
U.S. Appl. No. 11/380,124, filed Apr. 25, 2006 Non-Final Office Action dated Apr. 7, 2011.
U.S. Appl. No. 11/380,124, filed Apr. 25, 2006 Non-Final Office Action dated Jan. 16, 2009.
U.S. Appl. No. 11/380,124, filed Apr. 25, 2006 Non-Final Office Action dated Oct. 28, 2010.
U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Final Office Action dated Mar. 8, 2011.
U.S. Appl. No. 11/380,621, filed Apr. 27, 2006 Non-Final Office Action dated Jul. 1, 2009.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action issued on Dec. 3, 2008.
U.S. Appl. No. 11/725,287, filed Mar. 19, 2007 Non-final Office Action issued on Jun. 12, 2009.
U.S. Appl. No. 11/725,287, filed Mar. 19, 2007 Non-final Office Action issued on Mar. 29, 2010.
U.S. Appl. No. 11/937,302, filed Nov. 8, 2007 Final Office Action dated Oct. 13, 2011.
U.S. Appl. No. 11/937,302, filed Nov. 8, 2007 Non-Final Office Action dated Jun. 18, 2012.
U.S. Appl. No. 11/937,302, filed Nov. 8, 2007 Final Office Action dated Feb. 11, 2011.
U.S. Appl. No. 11/937,302, filed Nov. 8, 2007 Non-Final Office Action dated Apr. 15, 2011.
U.S. Appl. No. 11/937,302, filed Nov. 8, 2007 Non-Final Office Action dated Sep. 13, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Dec. 13, 2010.

(56) References Cited

OTHER PUBLICATIONS

U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/023,280, filed Jan. 31, 2008 Notice of Allowance dated Mar. 28, 2011.
U.S. Appl. No. 12/143,377, filed Jun. 20, 2008 Final Office Action mailed Oct. 19, 2009.
U.S. Appl. No. 12/143,377, filed Jun. 20, 2008 Non-final Office Action mailed Apr. 27, 2009.
U.S. Appl. No. 12/175,182, filed Jul. 17, 2008 Non-final Office Action mailed Sep. 3, 2009.
U.S. Appl. No. 12/267,160, filed Nov. 7, 2008 Final Office Action dated Jun. 1, 2012.
U.S. Appl. No. 12/267,160, filed Nov. 7, 2008 Non-Final Office Action dated Nov. 1, 2011.
U.S. Appl. No. 12/419,854, filed Apr. 7, 2009 Final Office Action dated Nov. 29, 2011.
U.S. Appl. No. 12/419,854, filed Apr. 7, 2009 Non-Final Office Action dated Jun. 26, 2012.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jul. 29, 2010.
U.S. Appl. No. 12/419,957, filed Apr. 7, 2009 Non-Final Office Action dated Jun. 30, 2009.
U.S. Appl. No. 12/419,957, filed Apr. 7, 2009 Notice of Allowance dated Mar. 7, 2011.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Advisory Action dated Sep. 15, 2011.
U.S. Appl. No. 12/617,981, filed Nov. 13, 2009 Final Office Action dated Aug. 2, 2012.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Dec. 21, 2011.
U.S. Appl. No. 12/617,981, filed Nov. 13, 2009 Non-Final Office Action dated Jan. 5, 2011.
CN 201080020088.3 filed Nov. 7, 2011 First Office Action dated Mar. 4, 2013.
ECRI Institute, Healthcare Product Comparison System, Dec. 2007.
EP 06751664.1 filed Apr. 27, 2006 First Examination Report dated Jul. 11, 2013.
EP 06845998.1 filed Dec. 21, 2006 Examination Report dated May 13, 2013.
EP 10183380.4 filed Apr. 25, 2006 European Search Report dated May 22, 2013.
EP 10183382.0 filed Apr. 25, 2006 European Search Report dated May 22, 2013.
EP 10183394.5 filed Apr. 25, 2006 European Search Report dated May 22, 2013.
EP 10183398.6 filed Apr. 25, 2006 European Search Report dated May 22, 2013.
EP 10762377.9 filed Oct. 5, 2011 Office Action dated Jul. 17, 2013.
EP 13158343.7 filed Mar. 8, 2013 Extended European Search Report dated May 14, 2013.
Ethanol Lock Technique for Prevention and Treatment of Central line-Associated Bloodstream Infections (NEBRASKA) Aug. 13, 2011, Accessed: Jun. 29, 2013 http://www.nebraskamed.com/app_files/pdf/careers/education-programs/asp/tnmc_etohlock_final.pdf.
JP 2012-156976 filed Jul. 12, 2012 Submission of Documents by Third Party dated May 14, 2013.
Medcomp Dialysis and Vascular Access Products (MEDCOMP) Jun. 30, 2009, Accessed Jun. 29, 2013 http://www.medcompnet.com/products/flipbook/pdf/PN2114G_Medcomp_Catalog.pdf.
PCT/US2013/031035 filed Mar. 13, 2013 International Search Report and Written Opinion dated Jun. 3, 2013.
Takeuchi, Syuhei et al., "Safety Considerations in the Power Injection of Contrast Medium via a Totally Implantable Central Venous Access System," Japan Journal of Interventional Radiology vol. 20, No. 1, pp. 27-30, Jan. 2005.
U.S. Appl. No. 11/380,124, filed Apr. 25, 2006 Notice of Allowance dated Apr. 29, 2013.
U.S. Appl. No. 12/419,854, filed Apr. 7, 2009 Advisory Action dated May 17, 2013.
U.S. Appl. No. 12/419,854, filed Apr. 7, 2009 Final Office Action dated Feb. 14, 2013.
U.S. Appl. No. 12/420,007, filed Apr. 7, 2009 Final Office Action dated Mar. 22, 2013.
U.S. Appl. No. 12/917,323, filed Nov. 1, 2010 Advisory Action dated Apr. 10, 2013.
U.S. Appl. No. 13/438,586, filed Apr. 3, 2012 Advisory Action dated May 29, 2013.
U.S. Appl. No. 13/438,586, filed Apr. 3, 2012 Final Office Action dated Mar. 7, 2013.
U.S. Appl. No. 13/471,219, filed May 14, 2012 Non-Final Office Action dated Jul. 10, 2013.
U.S. Appl. No. 13/571,088, filed Aug. 9, 2012 Final Office Action dated Jul. 16, 2013.
U.S. Appl. No. 13/571,088, filed Aug. 9, 2012 Non-Final Office Action dated Feb. 27, 2013.
U.S. Appl. No. 13/776,451, filed Feb. 25, 2013 Non-Final Office Action dated Jul. 24, 2013.
U.S. Appl. No. 13/853,942, filed Mar. 29, 2013 Non-Final Office Action dated Jul. 26, 2013.
U.S. Appl. No. 95/002,089, filed Aug. 20, 2012 Action Closing Prosecution dated Jun. 12, 2013.
U.S. Appl. No. 95/002,090, filed Aug. 20, 2012 Action Closing Prosecution dated Jun. 12, 2013.
U.S. Appl. No. 95/002,092, filed Aug. 20, 2012 Action Closing Prosecution dated Jun. 12, 2013.
Allergan, Inc. LAP-BAND® System Fact Sheet. © 2007.
AngioDynamics, Smart Port Guidelines for Health Care Providers, 1996.
B. Braun, Easypump Product Page, accessed May 11, 2011.
B. Braun, Port Catheter Systems Product Page, accessed May 11, 2011.
BARD Access Systems Mar. 21, 1995 Product Release to Market form for "M.R.I. Port with 8 Fr. ChronoFlexO Catheter", "M.R.I. Port with 8Fr. ChronoFlex Catheter with Intro-Eze™", "M.R.I. Port with 8. Fr ChronoFlex Catheter and Peel Apart", "M.R.I. Port with 8Fr. ChronoFlex Catheter Demo Kit". Drawings included.
Bard Healthcare Leaflet (2001).
Baxter Guidelines on Port Maintainence (Jun. 2003).
Baxter Healthport® Focus (Oct. 1999).
Baxter Healthport® Venous Systems (Oct. 2002).
Baxter Patient Information, Healthport® System (May 1999).
Baxter Therapy Systems, Baxter Healthport® Jan. 1999.
Biffi, R. et al. "Use of totally implantable central venous access ports for high-dose chemotherapy and peripheral blood stem cell transplantation: results of a monocentre series of 376 patients." Annals of Oncology 15:296-300, 2004.
Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.
Biffi, Roberto, et al. "A Randomized, Prospective Trial of Central Venous Ports Connected to Standard Open-Ended or Groshong Cath-

(56) References Cited

OTHER PUBLICATIONS eters in Adult Oncology Patients." American Cancer Society, vol. 92, No. 5, pp. 1204-1212, Sep. 1, 2001.
BioEnterics Corporation, LAP-BAND® "Adjustable Gastric Banding System" Product Brochure.
Braun Product Catalog (Aug. 2005).
Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.
Carlson et al., "Safety Considerations in the Power Injection of Contrast Media Via Central Venous Catheters during Computed Tomographic Examinations," Investigative Radiology, (May 1992) 27: 337-340.
Clinical Plastic Products, "Oncology Jet Port Plus Catheter Systems" Instructions for Use, 2011.
Cook Vital-Port® Product Catalog (2000).
Costa, Nancy, "More Than Skin Deep: An Overview of Iodinated Contrast Media . . ." Journal for the Association for Vascular Access, vol. 8, No. 4, 2003.
Costa, Nancy, "Understanding Contrast Media." Journal of Infusion Nursing, vol. 27, No. 5, Sep./Oct. 2004.
Coyle, Douglas et al, Power Injection of Contrast Media via Peripherally Inserted Central Catheters for CT, J Vasc Interv Radiol, pp. 809-814, vol. 15, 2004.
Deltec Port Systems (Feb. and Apr. 1996).
Department of Health and Human Services, C-Port 510(k) FDA Clearance, Jun. 5, 2003.
EP 06751411 filed Apr. 25, 2006 Office Action dated Aug. 10, 2009.
EP 06751411 filed Apr. 25, 2006 Office Action dated Sep. 2, 2008.
EP 06751411 filed Apr. 25, 2006 Opposition by Aesculap AG dated Oct. 5, 2011.
EP 06751411 filed Apr. 25, 2006 Opposition by Fresenius Kabi Deutschland GmbH dated Oct. 11, 2011.
EP 06751411 filed Apr. 25, 2006 Opposition by pfm medical ag dated Oct. 12, 2011.
EP 06845998 filed Dec. 21, 2006 Office Action dated Mar. 10, 2011.
EP 06845998 filed Dec. 21, 2006 Supplementary Search Report dated Jul. 22, 2010.
EP 99964086 filed Dec. 3, 1999 Office Action dated Dec. 15, 2005.
EP 99964086 filed Dec. 3, 1999 Office Action dated Mar. 1, 2005.
EP 99964086 filed Dec. 3, 1999 Office Action dated Mar. 30, 2005.
Extravasation of Radiologic Contrast, PA-PSRS Patient Safety Advisory, vol. 1 No. 3, Sep. 2004.
Extreme Access™ Bard Access Systems, Inc. Product Brochure, 2003.
Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.
Fresenius Brochure on Intraport 1, Intraport II, and Bioport (Nov. 1998).
Gebauer, B. et al., "Contrast Media Power Injection Using Central Venous Port Catheters—Results of an In-Vitro Study," Experimental Radiology 2005: 177: 1417-1423.
Hou, Shaw-Min et al. "Comparisons of Outcomes and Survivals for Two Central Venous Access Port Systems." Journal of Surgical Oncology, 91:61-66, 2005.
Inamed Health, BioEnterics® LAP-BAND® "Adjustable Gastric Banding System" Product Brochure, Dec. 2003.
Johnson, Kathleen A., "Power Injectable Portal Systems." Journal of Radiology Nursing, vol. 28, Issue 1, Mar. 2009.
JP 2007-558331 filed Mar. 6, 2006 Office Action dated May 17, 2011.
JP 2008-509056 filed Apr. 25, 2006 Office Action dated Apr. 4, 2012.
JP 2008-509056 filed Apr. 25, 2006 Office Action dated Jun. 7, 2011.
Kaste et al., "Safe use of power injectors with central and peripheral venous access devices for pediatric CT," Pediatr Radiol (1996) 26: 499-501.
L-CATH® FOR PORTS, Luther Medical Products, Inc., Tustin, California, 2 pages, 1994.
LaMaitre Vascular "Port Implantations: using the OptiLock Implantable Port," product information, available at http://www.lemaitre.com/specs.pop.asp, last accessed Apr. 2003, 14 pages.
LAP-BAND AP™ "System with Adjustable Gastric Banding system with OMNIFORM TN Design," Product Brochure, Jul. 2007, 16 pages.
Bard Access Systems, BardPort and X-Port Implanted Ports Brochure, © 2007.
Bard Access Systems, BardPort, Slim Port and X-Port Instructions for Use, May 2003.
Bard Access Systems, BardPort™ Implanted Ports Patient Information, Feb. 1993.
Bard Access Systems, Ports Brochure, © 2003.
Bard Access Systems, Titanium Dome Implantable Port, http://www.bardacess.com, last accessed Jan. 10, 2012.
CN 200980153471.3 filed Jun. 30, 2011 First Office Action dated Dec. 25, 2012.
EP 06751411 filed Apr. 25, 2006 Decision Revoking the European Patent dated Aug. 1, 2012.
EP 06845998.1 filed Dec. 21, 2006 Examination Report dated Nov. 7, 2012.
EP 10762377.9 filed Oct. 5, 2011 European Search Report dated Aug. 3, 2012.
JP 2007-558331 filed Mar. 6, 2006 Office Action dated Jan. 22, 2013.
Medtronic IsoMed® Constant-Flow Infusion System: Clinical Reference Guide for Hepatic Arterial Infusion Therapy, Revised Sep. 2000.
Nucleus Cochlear Implant Systems; User Manual for the ESPrit and ESPrit 22 speech processor and accessories, Issue 3, Apr. 2000.
PCT/US11/37038 filed May 18, 2011 Written Opinion and Search Report dated Aug. 30, 2011.
PCT/US2011/037038 filed May 18, 2011 International Preliminary Report on Patentability dated Nov. 29, 2012.
PCT/US2011/037038 filed May 18, 2011 International Search Report and Written Opinion dated Aug. 30, 2011.
Request for Inter partes Reexamination of U.S. Patent No. 7,785,302, filed Aug. 20, 2012.
Request for Inter partes Reexamination of U.S. Patent No. 7,947,022, filed Aug. 20, 2012.
Request for Inter partes Reexamination of U.S. Patent No. 7,959,615, filed Aug. 20, 2012.
U.S. Appl. No. 11/937,302, filed Nov. 8, 2007 Final Office Action dated Nov. 8, 2012.
U.S. Appl. No. 12/267,160, filed Nov. 7, 2008 Examiner's Answer dated Dec. 5, 2012.
U.S. Appl. No. 12/420,007, filed Apr. 7, 2009 Non-Final Office Action dated Oct. 16, 2012.
U.S. Appl No. 12/917,323, filed Nov. 1, 2010 Final Office Action dated Jan. 29, 2013.
U.S. Appl. No. 12/917,323, filed Nov. 1, 2010 Non-Final Office Action dated Aug. 15, 2012.
U.S. Appl. No. 13/113,834, filed May 23, 2011 Final Office Action dated Nov. 23, 2012.
U.S. Appl. No. 13/438,586, filed Apr. 3, 2012 Non-Final Office Action dated Sep. 19, 2012.
U.S. Appl. No. 29/382,235, filed Dec. 30, 2010 Non-Final Office Action dated Oct. 3, 2012.
U.S. Appl. No. 29/382,246, filed Dec. 30, 2010 Notice of Allowance dated Oct. 3, 2012.
U.S. Appl. No. 95/002,089, filed Aug. 20, 2012 Office Action In and Order Granting/Denying Request for Inter Partes Reexamination dated Nov. 7, 2012.
U.S. Appl. No. 95/002,090, filed Aug. 20, 2012 Office Action In and Order Granting/Denying Request for Inter Partes Reexamination dated Nov. 7, 2012.
U.S. Appl. No. 95/002,092, filed Aug. 20, 2012 Office Action In and Order Granting/Denying Request for Inter Partes Reexamination dated Nov. 13, 2012.
PCT/US2010/030256 filed Apr. 7, 2010 Written Opinion dated Jun. 4, 2010.
PCT/US2010/054994 filed Nov. 1, 2010 Search Report dated Jan. 10, 2011.

(56) References Cited

OTHER PUBLICATIONS

PCT/US2010/054994 filed Nov. 1, 2010 Written Opinion dated Jan. 10, 2011.
Port-A-Cath® P.A.S. PORT® Systems by Deltec, Product Specifications, 1999.
PORT-A-CATH® "Implantable Epidural, Aterial and Peritonial Access Systems" Internet Product Listing. <<http://web.archive.org/web/20001119035900/www.deltec.com/cPacspl.htm.>> last accessed Jun. 4, 2012.
PORT-A-CATH® "Many PORT-A-CATH® System Choices" Product Brochure. © 1996 SIMS Deltec, Inc.
PORT-A-CATH® & PORT-A-CATH® II Dual-lumen Implantable Venous Access Systems Product Specifications, 2005.
PORT-A-CATH® and P.A.S. PORT® POWER P.A.C. Information Sheet, 2006.
Rappolt, Richard T., et al. "Radiopaque Codification and X-ray Identification of Ingested Drugs." Ingestive Radiology, May-Jun. 1966.
Salis et al., "Maximal flow rates possible during power injection through currently available PICCs: An in-vitro study," J Vasc Interv Radiol 2004; 15:275-281.
Sandstede, Joern, "Pediatric CT," available online at www.multislice-ct.com, MultiSLICE-CT.com, version 02, May 2, 2003.
Sanelli, et al., "Safety and Feasibility of Using a Central Venous Catheter for Rapid Contrast Injection Rates." American Journal of Radiology, vol. 183, pp. 1829-1834, Dec. 2004.
Shah, Tilak M., "Radiopaque Polymer Formulations for Medical Devices." Medical Device and Diagnostic Industry, Mar. 2000.
Smith Medical, PORT-A-CATH® "Single-lumen Implantable Vascular Access Systems" Product Specifications, 2004.
Smith, Lisa Hartkoph, "Implanted Ports, Computed Tomography, Power Injectors, and Catheter Rupture." Clinical Journal of Oncology Nursing, vol. 12 , No. 5. Oct. 2008.
Smiths Medical, "Smiths Medical Launches Implantable Ports for Easy Viewing Under CT Scans" Press Release, Jan. 5, 2011.
Soloman, et al., "CIN Strategies: Anticipate, Manage, Prevent." Supplement to Imaging Economics, May 2007.
Statement of Prof. Dr. med. Karl R. Aigner, Oct. 11, 2011.
Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.
Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, filed Feb. 25, 2003 Non-Final Office Action dated Feb. 13, 2006.
U.S. Appl. No. 10/374,000, filed Feb. 25, 2003 Non-Final Office Action dated May 20, 2009.
U.S. Appl. No. 10/374,000, filed Feb. 25, 2003 Non-final Office Action mailed Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action mailed Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 11/320,223, filed Dec. 28, 2005 Advisory Action dated Dec. 1, 2011.
U.S. Appl. No. 11/320,223, filed Dec. 28, 2005 Notice of Allowance dated Jan. 6, 2012.
U.S. Appl. No. 11/320,223, filed Dec. 28, 2005 Final Office Action dated Aug. 3, 2011.
U.S. Appl. No. 11/320,223, filed Dec. 28, 2005 Final Office Action dated Jun. 19, 2009.
U.S. Appl. No. 11/320,223, filed Dec. 28, 2005 Final Office Action dated Jun. 22, 2010.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Mar. 16, 2011.
U.S. Appl. No. 11/320,223, filed Dec. 28, 2005 Non-Final Office Action dated Sep. 18, 2008.
U.S. Appl. No. 11/368,954, filed Mar. 6, 2006 Non-Final Office Action dated Jul. 21, 2009.
U.S. Appl. No. 11/368,954, filed Mar. 6, 2006 Notice of Allowance dated Jun. 24, 2010.
CN 200980153471.3 filed Jun. 30, 2011 Second Office Action dated Sep. 18, 2013.
EP 06751411 filed Apr. 25, 2006 Decision of the Technical Board of Appeal dated Jul. 24, 2013.
JP 2007-558331 filed Mar. 6, 2006 Office Action dated Aug. 20, 2013.
JP 2012-156976 filed Jul. 12, 2012 Notice of Reasons for Refusal dated Aug. 27, 2013.
MX/a/2011/004499 filed Apr. 28, 2011 First Office Action dated Jul. 25, 2013.
U.S. Appl. No. 13/438,586, filed Apr. 3, 2012 Notice of Allowance dated Sep. 16, 2013.
U.S. Appl. No. 13/776,517, filed Feb. 25, 2013 Non-Final Office Action dated Nov. 15, 2013.
Bard Access Systems, BadPort, SlimPort, X-Port Instructions for Use, 24 pages, Oct. 2012.
Bard Access Systems, PowerPort and PowerLoc CT Guide, 11 pages, Dec. 2009.
Bard Access Systems, PowerPort and PowerLoc Product Brochure, 6 pages, © 2007.
Bard Access Systems, PowerPort CT Guide, 16 pages, Mar. 2007.
Bard Access Systems, PowerPort Guidelines for CT Technologists, 1 page, Feb. 2007.
Bard Access Systems, PowerPort Guidelines for CT Technologists, 1 page, Jul. 2006.
Bard Access Systems, PowerPort Guidelines for Nurses, 1 page, Feb. 2007.
Bard Access Systems, PowerPort Guidelines for Physicians, 1 page, Feb. 2007.
Bard Access Systems, PowerPort Prescription Pad, 1 page, © 2007.
Bard Access Systems, PowerPort™ Implantable Port Product Information, © 2007.
Bard Access Systems, When in Doubt, SCOUT!, 1 page, © 2007.
Biotronik, Stratos Cardiac Resynchronization Therapy Pacemakers Technical Manual, 179 pages, © 2008.
Boston Scientific, Xcela™ Power Injectable PICC Directions for Use, 12 pages, © 2007.

(56) References Cited

OTHER PUBLICATIONS

CN 200980153471.3 filed Jun. 30, 2011 Third Office Action dated May 28, 2014.
CN 201080020088.3 filed Nov. 7, 2011 Second Office Action dated Nov. 21, 2013.
CN 201080051911.7 filed May 16, 2012 First Office Action dated Dec. 27, 2013.
CN 201080051911.7 filed May 16, 2012 Second Office Action dated Jul. 16, 2014.
EP 06845998.1 filed Dec. 21, 2006 Summons for Oral Proceedings dated Sep. 30, 2014.
EP 10 831 973.2 filed May 30, 2012 Extended European Search Report dated Jul. 4, 2014.
EP 10183394.5 filed Apr. 25, 2006 Opposition by Smiths Medical ASD, Inc. dated Apr. 25, 2014.
EP 13158343.7 filed Mar. 8, 2013 Summons to Attend Oral Proceedings dated Oct. 20, 2014.
JP 2012-156976 filed Jul. 12, 2012 Notice of Reasons for Refusal dated Apr. 8, 2014.
JP 2012-504826 filed Oct. 6, 2011 First Office Action dated Mar. 4, 2014.
JP 2013-209156 filed Oct. 4, 2013 Non-Final Office Action dated Oct. 7, 2014.
MX/a/2011/004499 filed Apr. 28, 2011 Second Office Action dated May 25, 2014.
PFM Medical, Xcela™ Power Injectable Port Directions for Use, 15 pages, © 2008.
STD Manufacturing, Brochure with a Hickman port, 1 page, date unknown.
U.S. Appl. No. 12/419,854, filed Apr. 7, 2009 Notice of Allowance dated Apr. 7, 2014.
U.S. Appl. No. 12/917,323, filed Nov. 1, 2010 Non-Final Office Action dated Aug. 26, 2014.
U.S. Appl. No. 13/110,734, filed May 18, 2011 Non-Final Office Action dated Jul. 7, 2014.
U.S. Appl. No. 13/776,517, filed Feb. 25, 2013 Final Office Action dated Jun. 30, 2014.
U.S. Appl. No. 13/776,517, filed Feb. 25, 2013 Notice of Allowance dated Sep. 23, 2014.
U.S. Appl. No. 13/853,956, filed Mar. 29, 2013 Non-Final Office Action dated Dec. 3, 2013.
U.S. Appl. No. 13/853,956, filed Mar. 29, 2013 Non-Final Office Action dated Sep. 15, 2014.
U.S. Appl. No. 13/853,961, filed Mar. 29, 2013 Non-Final Office Action dated Dec. 3, 2013.
U.S. Appl. No. 13/853,961, filed Mar. 29, 2013 Non-Final Office Action dated Sep. 12, 2014.
EP 06845998.1 filed Dec. 21, 2006 Examination Report dated Feb. 6, 2014.
EP 10183382.0 filed Apr. 25, 2006 Intent to Grant dated Mar. 7, 2014.
EP 11784194.0 filed Nov. 29, 2012 extended European search report dated Feb. 21, 2014.
EP 13158343.7 filed Mar. 8, 2013 Examination Report dated Feb. 4, 2014.
PCT/US2013/056019 filed Aug. 21, 2013 International Search Report and Written Opinion dated Feb. 28, 2014.
U.S. Appl. No. 13/776,517, filed Feb. 25, 2013 Non-Final Office Action dated Feb. 27, 2014.

* cited by examiner

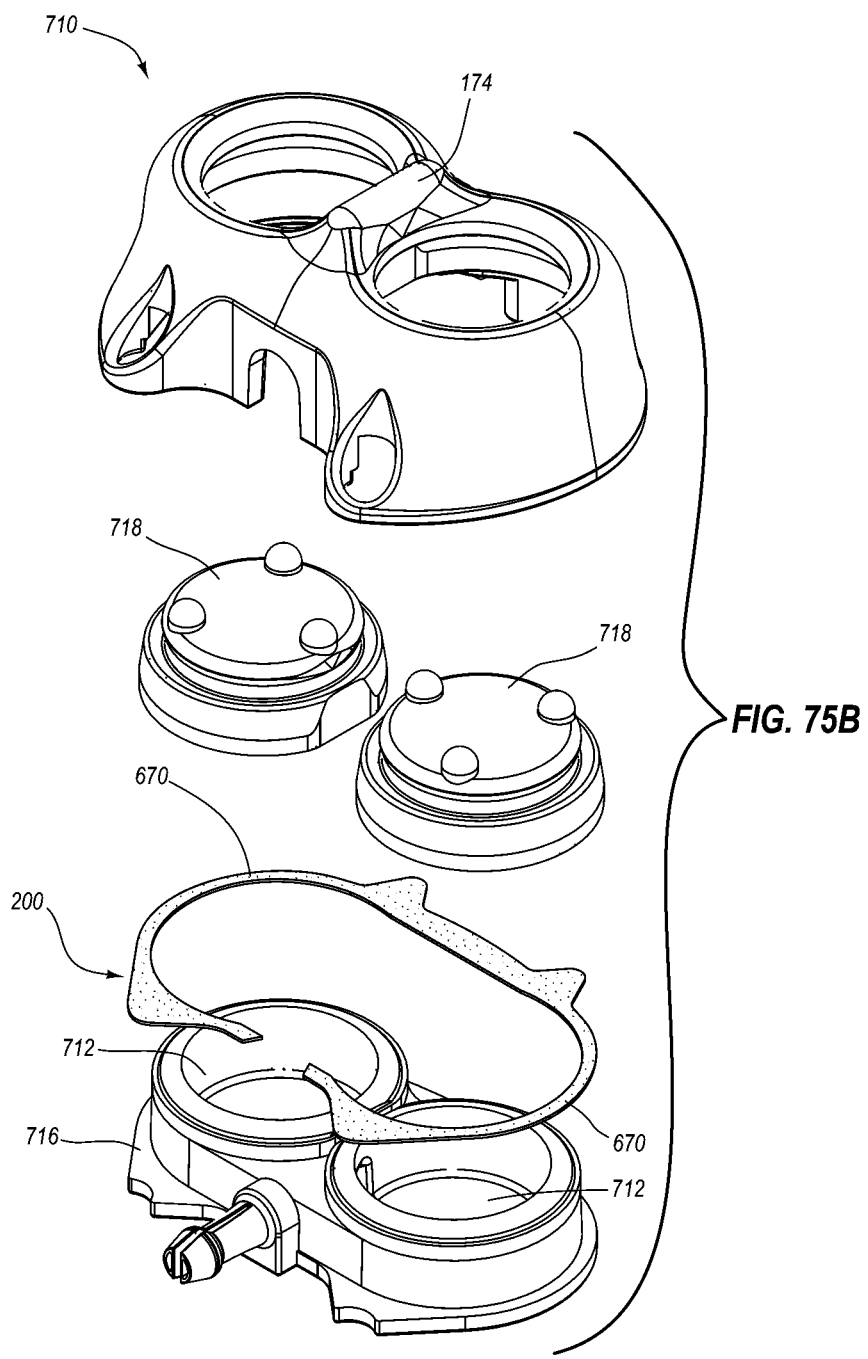

SYSTEMS AND METHODS FOR IDENTIFYING AN ACCESS PORT

RELATED APPLICATIONS

This application is a division of U.S. patent application Ser. No. 12/610,084, filed Oct. 30, 2009, now U.S. Pat. No. 8,202, 259, which claims the benefit of U.S. Patent Application No. 61/110,507, filed Oct. 31, 2008 and which is a continuation-in-part of U.S. patent application Ser. No. 12/420,028, filed Apr. 7, 2009, now U.S. Pat. No. 7,947,022, which is a continuation-in-part of U.S. patent application Ser. No. 11/368, 954, filed Mar. 6, 2006, now U.S. Pat. No. 7,785,302, which claims the benefit of U.S. Patent Application No. 60/658,518, filed Mar. 4, 2005. Each of the afore-referenced applications is incorporated, in its entirety, by this reference.

BRIEF DESCRIPTION OF THE DRAWINGS

FIGS. 75A-75C show various views of an identifier for an access port according to one embodiment.

DETAILED DESCRIPTION

Figure 1A:
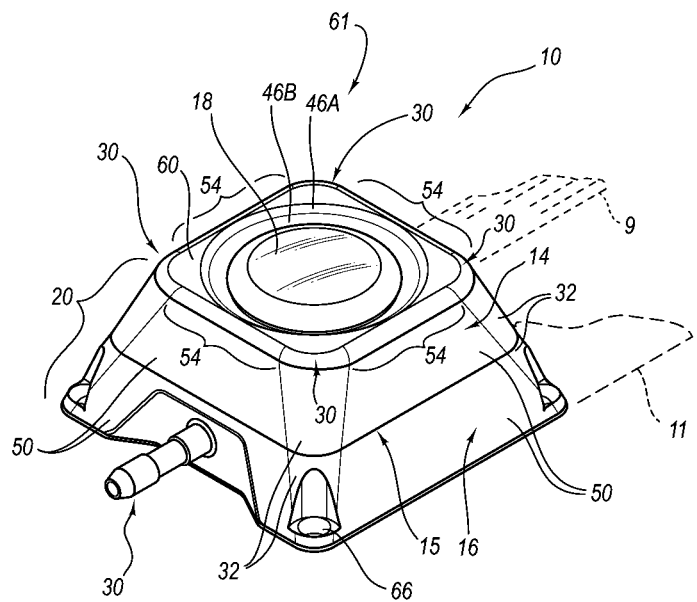
FIG. 1A shows a perspective view of an embodiment of an access port according to the instant disclosure.

The instant disclosure relates generally to percutaneous access and, more specifically, to methods and devices associated with percutaneous access. Generally, the instant disclosure relates to an access port for subcutaneous implantation. In one embodiment, an access port may allow a physician or other medical personnel to obtain long term percutaneous access to the interior of a patient's body. Employing an access port for percutaneous access may reduce the opportunity for infection by inhibiting fluid connections (that extend into the interior of a patient's body) from the patient's skin and from the external environment. The access device allows access to the interior of the patient without requiring a needle to pierce the skin. Further, internal components, such as a catheter or a valve, may be replaced without a surgical procedure. Features or aspects of the instant disclosure may apply to any such access ports for subcutaneous access to a patient, without limitation. The access port may be injected by hand (e.g., via a syringe including a needle) for example, or may be injected and pressurized by mechanical assistance (e.g., a so-called power injectable port).

Power injectable ports may be employed in, among other processes, for example, computed tomography ("CT") scanning processes. More particularly, a so-called "power injector" system may be employed for injecting contrast media into a peripherally inserted intravenous (IV) line. For example, such power injectors or injection systems may be commercially available from Medrad, Inc., a subsidiary of Schering AG, Germany and may be marketed under the trademark STELLANT®. Because fluid infusion procedures are often defined in terms of a desired flow rate of contrast media, such power injection systems are, in general, controllable by selecting a desired flow rate.

More specifically, the instant disclosure relates to an access port having at least one perceivable or identifiable feature for identifying the access port, wherein the identifiable feature is perceivable after the access port is implanted within a patient. For example, at least one or perhaps multiple identifiable feature(s) of an access port contemplated by the instant disclosure may be correlative to information (e.g., a manufacturer's model or design) pertaining to the access port. Thus, an identifiable feature from an access port of a particular model may be unique in relation to most if not all other identifiable features of another access port of a different model or design. Of course, the at least one identifiable feature of an access port contemplated by the instant disclosure may be further correlative with any information of interest, such as type of port, catheter type, date of manufacture, material lots, part numbers, etc. In one example, at least one identifiable feature of an access port may be correlative with the access port being power injectable. In this way, once at least one identifiable feature of an access port is observed or otherwise determined, correlation of such at least one feature of an access port may be accomplished, and information pertaining to the access port may be obtained.

In one embodiment, at least one feature may be perceived by palpation (i.e., to examine by touch), by way of other physical interaction, or by visual observation. Accordingly, a person of interest may touch or feel the access port through the skin to perceive at least one identifying characteristic thereof. In another embodiment, at least one identifiable feature may be perceived via x-ray or ultrasound imaging. In yet a further embodiment, at least one identifiable feature may be perceived through magnetic, light, or radio energy interaction or communication with the access port.

Figure 1B:
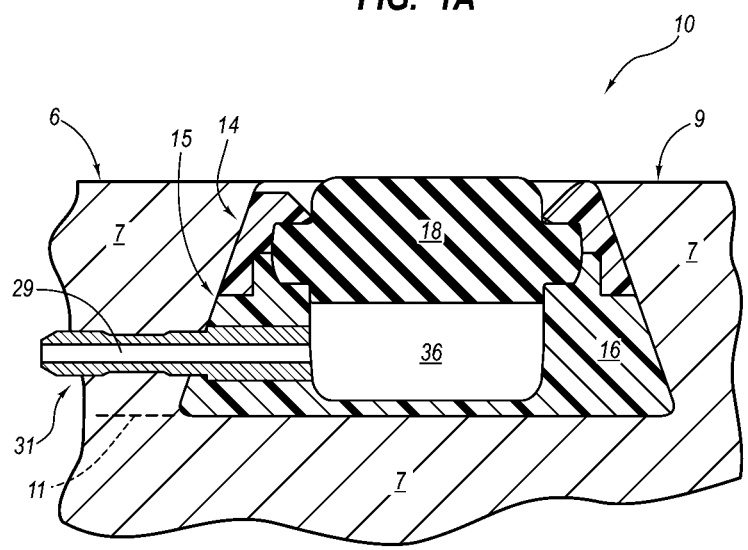
FIG. 1B shows a schematic side cross-sectional view the access port shown in FIG. 1A.

Turning to the embodiment wherein at least one feature may be perceived through palpation, other physical interaction, or visual observation, a topography or exterior surface feature of an access port contemplated by the instant disclosure may be configured for perception. For example, referring to FIGS. 1A and 1B, an exemplary access port 10 contemplated by the instant disclosure is shown. FIGS. 1A and 1B show a perspective view and a schematic side cross-sectional view, respectively, of an access port 10 for allowing percutaneous or otherwise internal access to a patient's body. Access port 10 includes a housing or body 20 defined by a cap 14 and a base 16. Cap 14 and base 16, as known in the art, may be configured for capturing therebetween a septum 18. As shown in FIG. 1A, cap 14 and base 16 may matingly engage one another along a mating line 15. Cap 14 and base 16 may be secured or affixed to one another via mechanical fasteners such as screws or other fastening devices, may be adhesively affixed to one another, or may be affixed to one another as known in the art. Further, cap 14, base 16, and septum 18 may collectively define a cavity 36 in fluid communication with a lumen 29 of outlet stem 31.

The body 20 may be implanted in a patient 7, as shown in FIG. 1B, to dispose the cavity 36 subcutaneously within the patient 7. Also, suture apertures 66 (FIG. 1A) may be used to affix the access port 10 within the patient 7, if desired. After the body 20 is implanted in a patient 7, the upper surface of the septum 18 may be substantially flush with the surface of the skin 6 of the patient 7 and may be repeatedly punctured for creating a percutaneous passageway from the exterior of the skin of the patient into the cavity 36. The outlet stem 31 may create a fluid-communicative passageway from the cavity 36 through the outlet stem 31 and into the interior of the patient 7. A catheter may be coupled to the outlet stem 31 for fluid communication with the cavity 36 and for transferring fluid from the cavity 36 to a desired remote location from the cavity 36 and within a patient 7.

Body 20 of access port 10 may comprise a bio-compatible material such as polysulfone, titanium, or any other suitably bio-compatible material as known in the art. Accordingly, the body 20 may be formed from a bio-compatible plastic material. If desired, the body 20 may comprise a penetrable material for penetration by sutures or needles. In another embodiment, and as discussed further hereinbelow, body 20 may comprise an impenetrable material such as, for instance, a metal if desired. Body 20 may include a concave bottom or, in another embodiment, may include a flat bottom, without limitation.

According to the instant disclosure, access port 10 may comprise a body 20 exhibiting at least one identifiable feature. More particularly, as shown in FIG. 1A, body 20 may exhibit a partial generally pyramidal shape (i.e., a polygonal base having surfaces for each side of the polygon extending toward a common vertex otherwise known as a frustum). Generally, a body 20 of an access port 10 may exhibit a partial pyramidal shape extending between a generally quadrilateral shaped base positioned at reference plane 11 and a generally quadrilateral shaped upper base positioned at reference plane 9. Reference planes 9 and 11 will not be shown in FIGS. 2-21, for clarity; however, reference to planes 9 or 11 with respect to FIGS. 2-21, as used herein, will refer to corresponding reference planes analogous to reference planes 9 and 11 as shown in FIGS. 1A and 1B.

As shown in FIG. 1A, the exterior of access port 10 is substantially defined by four substantially planar side surfaces 50 connected to one another by radiuses 32. In addition, the upper topography 61 of access port 10 is defined by upper surface 60 in combination with chamfers 46A and 46B and may be further defined by the upper surface of septum 18. Explaining further, the outer periphery of upper topography 61 may be described as a generally quadrilateral exterior formed by side regions 54 and having rounded corner regions 30 adjacent side regions 54. Such a configuration may provide an access port having at least one feature that may be perceived by palpation.

It may be appreciated that there are many variations to the geometry of access port 10 as shown in FIG. 1A. For instance, while the body 20 of access port 10 may be described as a partially pyramidal shape or frustum, the instant disclosure is not so limited. Rather, one or more of side surfaces 50 may be oriented at as may be desired, without reference to any other side surfaces 50. Accordingly, for example, one of surfaces 50 may be substantially vertical while the remaining surfaces 50 may be oriented at respective, selected angles. Furthermore, it should be understood that FIG. 1A is merely exemplary and that the dimensions and shape as shown in FIG. 1A may vary substantially while still being encompassed by the instant disclosure.

Figure 2:
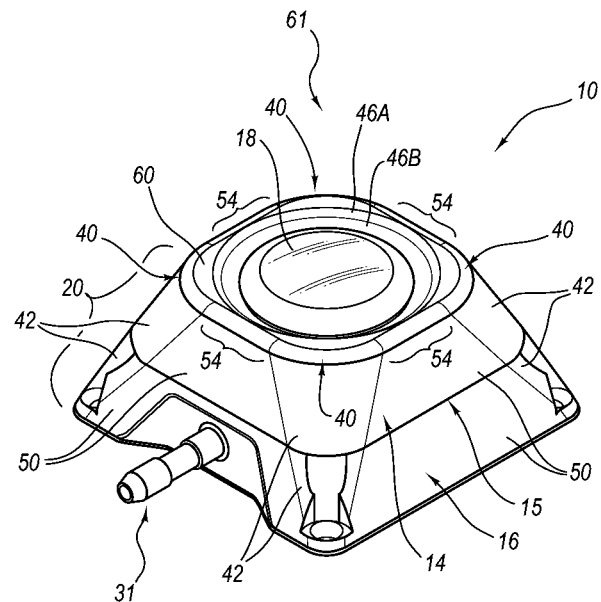
FIG. 2 shows a perspective view of an embodiment of an access port according to the instant disclosure.

FIG. 2 shows a perspective view of another embodiment of access port 10 according to the instant disclosure. As shown in FIG. 2, the exterior of access port 10 is substantially defined by a generally parallelogram-shaped base (positioned at reference plane 11 as shown in FIGS. 1A and 1B) extending generally pyramidally to a generally parallelogram-shaped upper surface (positioned at reference plane 9 as shown in FIGS. 1A and 1B). As shown in FIG. 2, radiuses 42 may be larger than radiuses 32 as shown in FIG. 1A. Furthermore, the upper topography 61 of access port 10 as shown in FIG. 2 may include rounded corner regions 40 which are larger than rounded corner regions 30 as shown in FIG. 1A. Thus, FIG. 2 shows an exemplary embodiment of an access port 10 that may be perceivably distinguishable from access port 10 as shown in FIGS. 1A and 1B. For example, a difference between one exterior of an access port contemplated by the instant disclosure and another exterior of a different access port contemplated by the instant disclosure may be determined by way of palpation.

In another embodiment, in another aspect contemplated by the instant disclosure, a template may be employed for perceiving at least one feature of an access port. For instance, a complementarily-shaped template may be positioned over and abutted against an access port contemplated by the instant disclosure so as to determine if the access port matches or substantially corresponds to the shape of the template. Such a process may reliably indicate or perceive at least one feature of an access port contemplated by the instant disclosure. Of course, a plurality of templates corresponding to different models of access ports may be serially engaged with an unknown access port so as to perceive at least one feature thereof. Such a process may allow for identification (e.g., of a model or manufacturer) of an access port contemplated by the instant disclosure.

Figure 3:
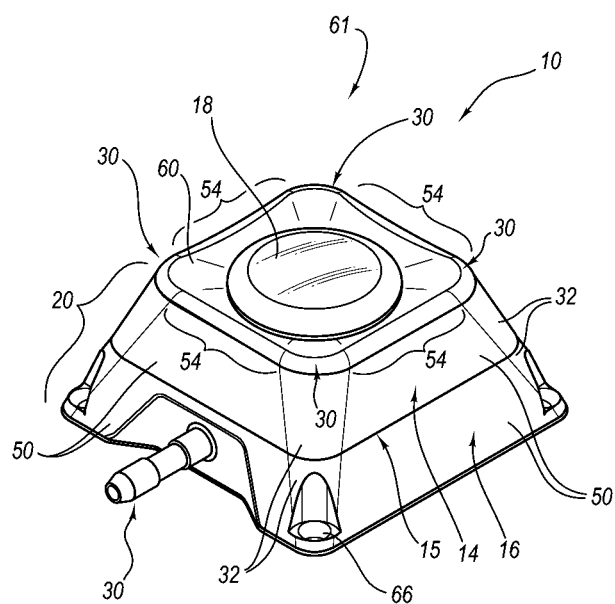
FIG. 3 shows a perspective view of an access port according to the instant disclosure.

In another aspect contemplated by the instant disclosure, an upper topography of an access port may include at least one feature for identifying the access port. For example, as shown in FIG. 3, upper surface 60 of access port 10 may be nonplanar. More specifically, upper surface 60 may be tapered or may arcuately extend downwardly (i.e., toward reference plane 11 as shown in FIGS. 1A and 1B) as it extends radially inwardly toward septum 18. Otherwise, access port 10, as shown in FIG. 3, may be configured substantially as described hereinabove with reference to FIGS. 1A and 1B. Thus, upper surface 60 is one exemplary example of at least one perceivable feature for identification of an access port contemplated by the instant disclosure.

Figure 4:
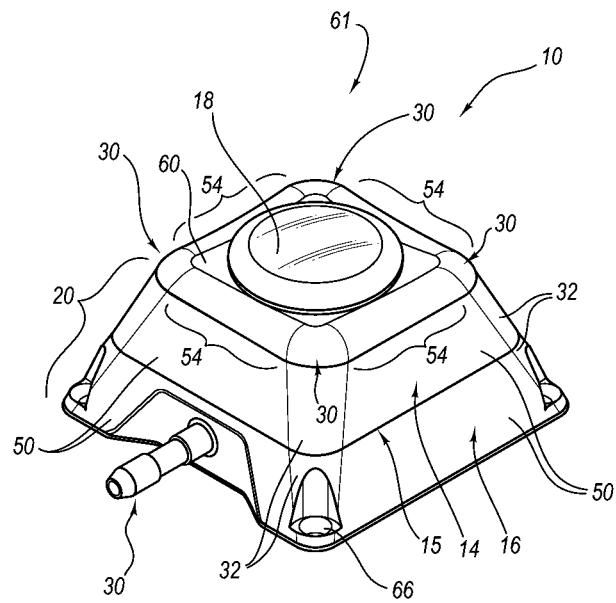
FIG. 4 shows a perspective view of an access port according to the instant disclosure.

In yet a further embodiment of an access port contemplated by the instant disclosure, side regions 54 extending between rounded corner regions 30 may exhibit at least one perceivable feature. For example, as shown in FIG. 4, access port 10 may include one or more side regions 54 that extend arcuately between adjacent rounded corner regions 30. Otherwise, access port 10, as shown in FIG. 4, may be configured substantially as described hereinabove with reference to FIGS. 1A and 1B. Side regions 54 may be congruent or symmetric with respect to one another or, in another embodiment, may be configured differently with respect to one another, without limitation.

Figure 5:
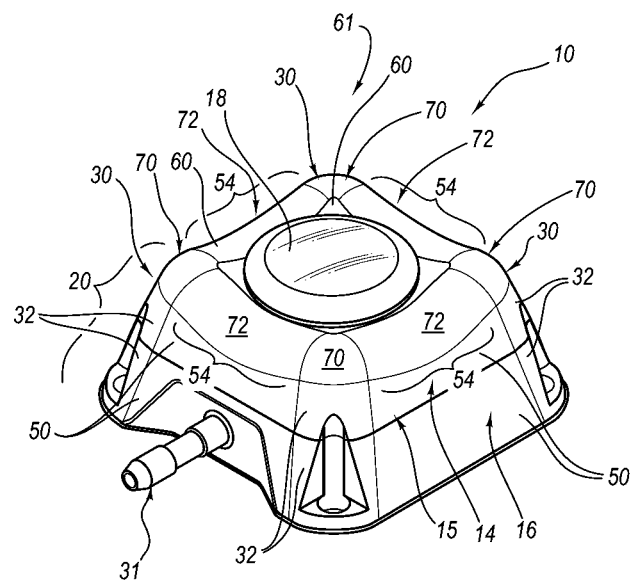
FIG. 5 shows a perspective view of an access port according to the instant disclosure.

FIG. 5 shows a further exemplary embodiment of an access port contemplated by the instant disclosure. More specifically, access port 10, as shown in FIG. 5, includes side regions 54 that form recessed regions 72 between adjacent rounded corner regions 30. Put another way, the upper topography 61 may include alternating recessed regions 72 and protruding regions 70 positioned generally about a periphery of septum 18. Otherwise, access port 10, as shown in FIG. 5, may be configured substantially as described hereinabove with reference to FIGS. 1A and 1B. Such a configuration may provide an access port having at least one identifiable feature.

Figure 6A:
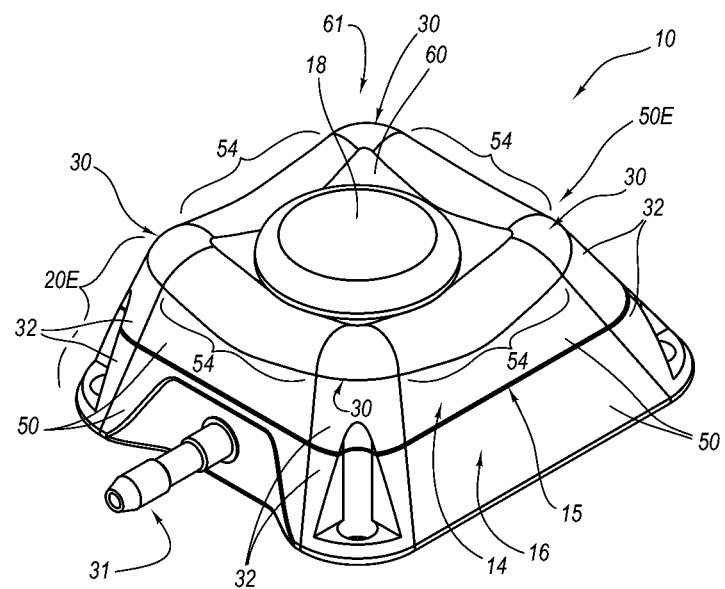
FIG. 6A shows a perspective view of an access port according to the instant disclosure.
Figure 6B:
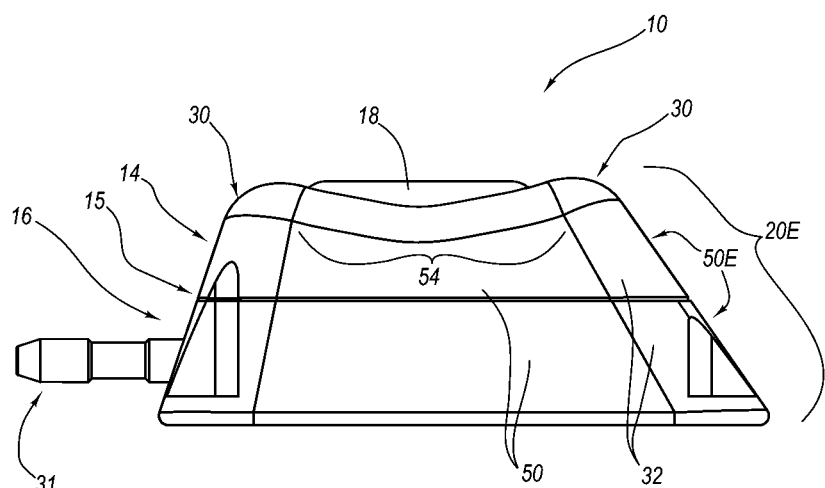
FIG. 6B shows a side view of the access port shown in FIG. 6A.

In a further embodiment of an access port contemplated by the instant disclosure, FIGS. 6A and 6B show a perspective view and a side view, respectively, of an access port 10 generally configured as is described with reference to FIG. 5 but having an elongated body 20E. More specifically, elongated body 20E of access port 10, as shown in FIGS. 6A and 6B, includes a side surface 50E that extends generally from upper topography 61 downwardly (i.e., toward reference plane 11 as shown in FIGS. 1A and 1B) and having a slope (e.g., an angle with respect to a vertical axis normal to an upper surface of septum 18) which is different from the other side surfaces 50. Otherwise, access port 10, as shown in FIG. 6, may be configured substantially as described hereinabove with reference to FIGS. 1A and 1B. Such a configuration may provide an elongated body 20E of an access port 10 having an elongated side portion.

Of course, one or more side surfaces of an access port according to the instant disclosure may be configured for forming a body exhibiting a selected shape as may be desired. An elongated body portion of an access port contemplated by the instant disclosure may form, in combination with other features as described hereinabove or, in another embodiment, taken alone, at least one perceivable feature for identification of an access port according to the instant disclosure.

Figure 7:
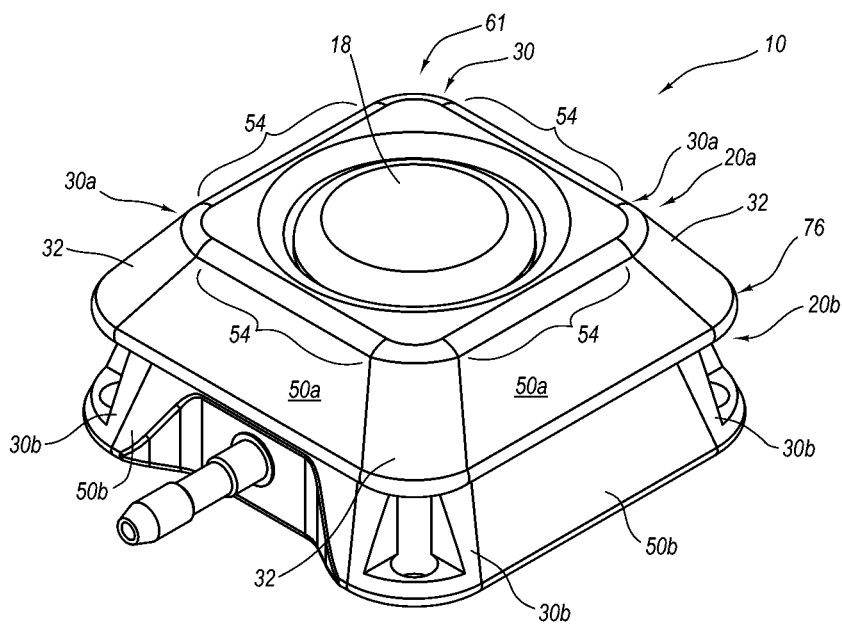
FIG. 7 shows a perspective view of an access port according to the instant disclosure.

FIG. 7 shows a further embodiment of an access port encompassed by the instant disclosure. Particularly, as shown in FIG. 7, access port 10 may include an upper body portion 20a and a lower body portion 20b. Furthermore, each of upper body portion 20a and lower body portion 20b may exhibit a partial pyramidal shape (i.e., a frustum), wherein the body portions 20a and 20b are stacked vertically with respect to one another. Accordingly, upper body portion 20a may form an overhanging rim feature 76 extending along a periphery of access port 10. Explaining further, lower body portion 20b may have an exterior substantially defined by side surfaces 50b and rounded corner regions 30b, while upper body portion 20a may have an exterior substantially defined by side surfaces 50a, rounded corner regions 30a, and upper topography 61. It may be appreciated that overhanging rim feature 76 may be sized and configured for perception via palpation. Such a configuration may provide a suitable access port for delivery of a beneficial or medicinal substance, the access port being identifiable (e.g., by model number, manufacturer, etc.) after implantation.

Figure 8:
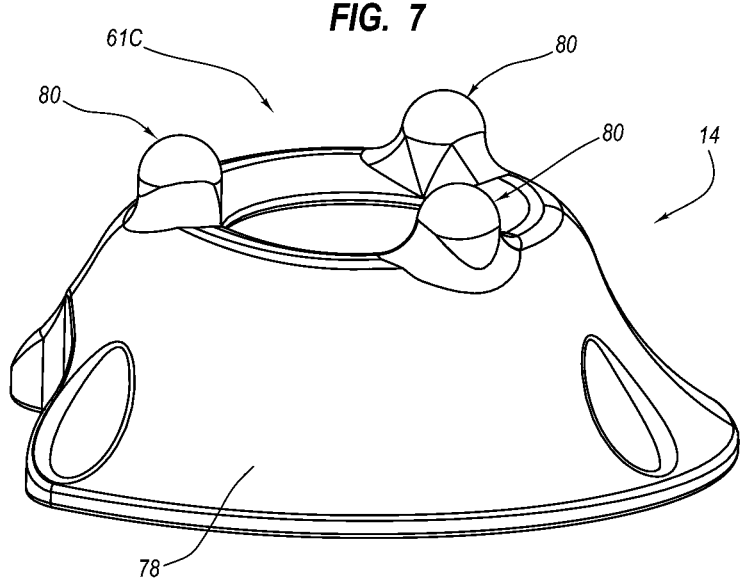
FIG. 8 shows a simplified perspective view of a cap for forming an access port according to the instant disclosure.

It should be understood that the instant disclosure contemplates access ports having an exterior geometry that is not quadrilateral in nature. Rather, the instant disclosure contemplates that an access port may have an exterior which is generally cylindrical, generally conical, generally elliptical, generally oval, or an exterior that is otherwise arcuate in nature. Specifically, the instant disclosure contemplates that an access port having a substantially rounded or arcuate exterior may include at least one feature configured for identification of the access port after implantation. For example, as shown in FIG. 8, shows a cap 14 that exhibits an exterior surface 78 that is substantially conical. Cap 14 may be assembled to a suitable base (not shown) for capturing a septum (not shown) as described hereinabove to form an access port 10 as generally described with reference to FIGS. 1-7.

The instant disclosure further contemplates that at least one protrusion, protruding region, recess, recessed region, undulation, or adjacent features of different elevation may comprise a feature for identifying an access port contemplated by the instant disclosure. More specifically, upper topography 61C, as shown in FIG. 8, may include a plurality of protrusions 80. Protrusions 80 may exhibit partially spherical upper surfaces that transition into a lower portion of cap 14. In further detail, protrusions 80 may be circumferentially spaced about the periphery of septum (not shown) as may be desired. In one embodiment, a plurality of protrusions 80 may be symmetrically circumferentially spaced about the periphery of septum (not shown). More generally, at least one protrusion 80 may be sized, configured, and positioned for forming at least one identifiable feature of an access port. Of course, at least one protrusion 80 may be structured for facilitating comfort of a patient within which the access port is implanted. As may be appreciated, at least one protrusion 80 or more than one protrusion 80 may be included in an upper topography 61C of an access port (not shown) contemplated by the instant disclosure.

Figure 9:
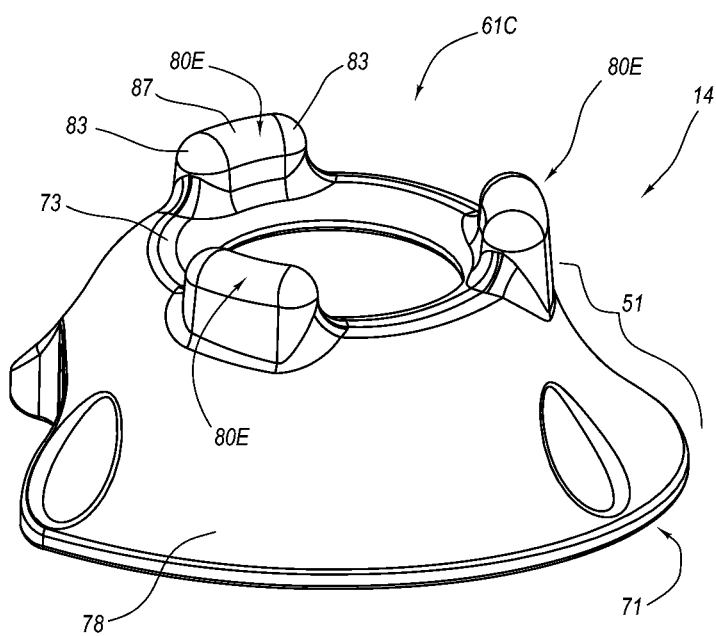
FIG. 9 shows a simplified perspective view of a cap for forming an access port according to the instant disclosure.

FIG. 9 shows another embodiment of a cap 14 including at least one protrusion 80E for forming and identifying an access port contemplated by the instant disclosure after implantation thereof within a patient. Protrusions 80E may extend circumferentially about a center of revolution. Thus, protrusions 80E may exhibit a body 87 portion circumferentially extending between rounded ends 83. Further, cap 14 may have an exterior surface 78 that is substantially symmetric about an axis of revolution. More generally, body 20 may extend from a generally circular, generally elliptical, or generally oval base positioned at a lower extent 71 of the cap 14 to an upper generally circular, generally elliptical, or generally oval cross section that is smaller than a cross section of the base and is positioned at an upper extent 73 (without considering protrusions 80E) of the cap 14. In addition, side surface 51, as shown in FIG. 9, extends arcuately between the base and the upper topography 61 of cap 14. Side surface 51 may extend in a generally tapered or conical fashion, may exhibit a radius or other arcuate shape, or may otherwise transition between a cross section of the base of the access port to a cross section proximate the upper topography 61C thereof.

Figure 10:
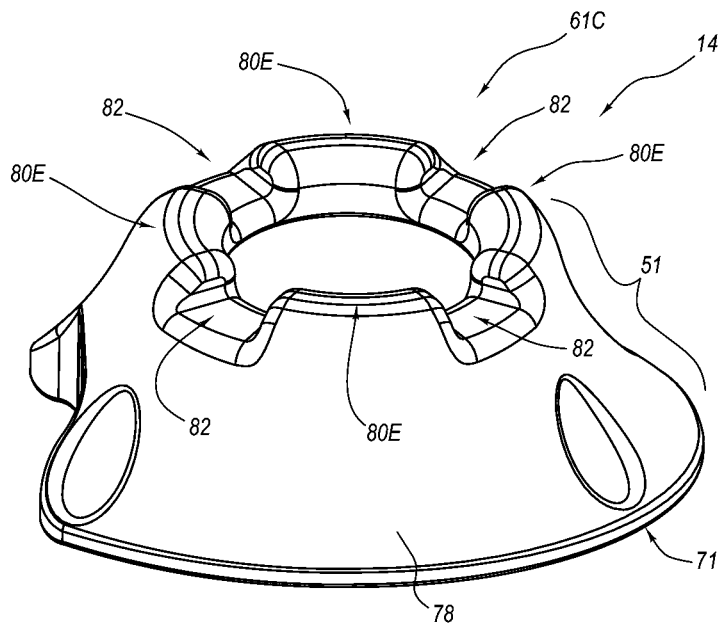
FIG. 10 shows a simplified perspective view of a cap for forming an access port according to the instant disclosure.
Figure 11:
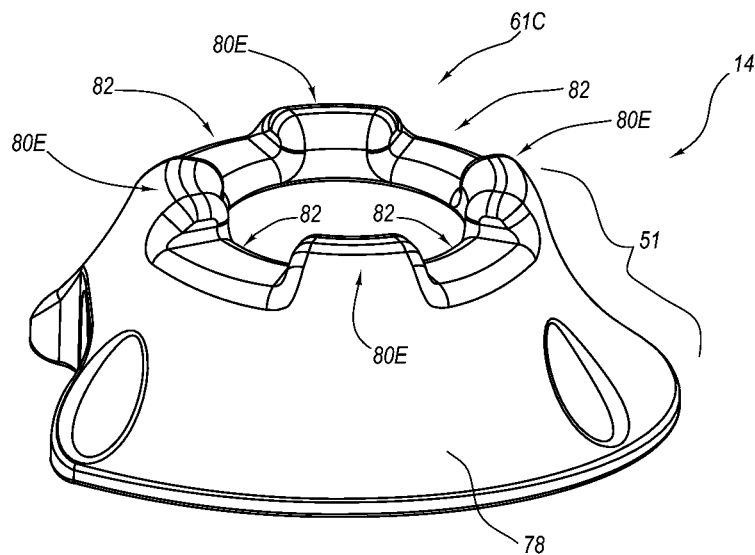
FIG. 11 shows a simplified perspective view of a cap for forming an access port according to the instant disclosure.
Figure 12:
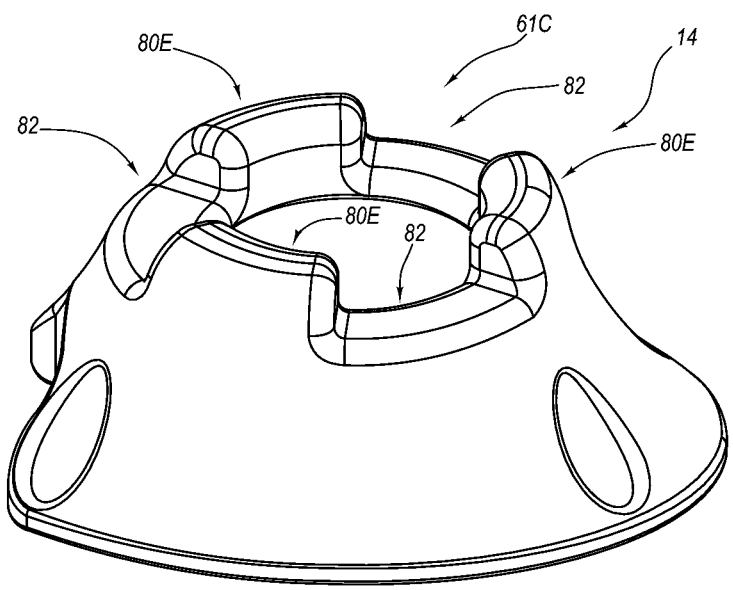
FIG. 12 shows a simplified perspective view of a cap for forming an access port according to the instant disclosure.

Further, FIG. 10 shows an embodiment of a cap 14 for forming an access port contemplated by the instant disclosure having an upper topography 61C thereof comprising alternating circumferentially extending protrusions 80E and circumferentially extending recesses 82, wherein the circumferentially extending protrusions 80E are circumferentially larger than the circumferentially extending recesses 80E. In another embodiment of an access port contemplated by the instant disclosure, FIG. 11 shows a perspective view of a cap 14 having an upper topography 61C thereof comprising alternating circumferentially extending protrusions 80E and circumferentially extending recesses 82, wherein the circumferentially extending protrusions 80E and the circumferentially extending recesses 82 are substantially equal in (circumferential) sized or extension. In yet a further embodiment of a cap 14 for forming an access port contemplated by the instant disclosure, FIG. 12 shows a perspective view of a cap 14 having an upper topography 61C thereof comprising three circumferentially extending protrusions 80E and three circumferentially extending recesses 82, arranged so as to alternate circumferentially, wherein the circumferentially extending protrusions 80E and the circumferentially extending recesses 82 are substantially equal in (circumferential) size.

Figure 13:
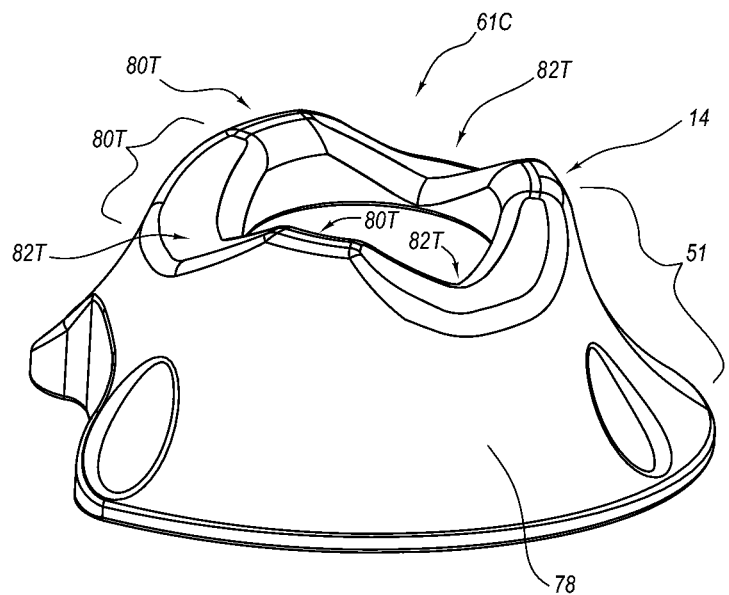
FIG. 13 shows a simplified perspective view of a cap for forming an access port according to the instant disclosure.
Figure 14:
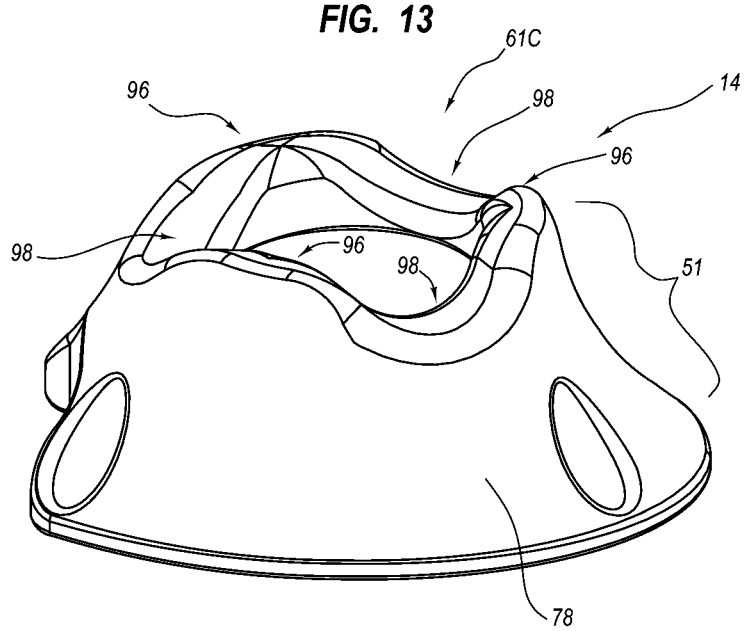
FIG. 14 shows a simplified perspective view of a cap for forming an access port according to the instant disclosure.

FIG. 13 shows a perspective view of an additional embodiment of an cap 14 for forming an access port contemplated by the instant disclosure including an upper topography 61C including circumferentially extending protrusions 80T and circumferentially extending recesses 82T, wherein transition regions 81 are provided between circumferentially extending protrusions 80T and circumferentially extending recesses 82T. Such transition regions 81, as shown in FIG. 13, may taper or generally smoothly transition between a circumferentially extending protrusion 80T and a circumferentially extending recess 82T. Also, FIG. 14 shows a perspective view of an additional embodiment of a cap 14 for forming an access port contemplated by the instant disclosure including an upper topography 61C including protrusion regions 96 and recessed regions 98 that transition between one another and alternate circumferentially so as to form an undulating topography comprising upper topography 61C. Such an undulating topography, as shown in FIG. 14, generally smoothly transitions between circumferentially adjacent protrusion regions 96 and recessed regions 98.

Figure 15A:
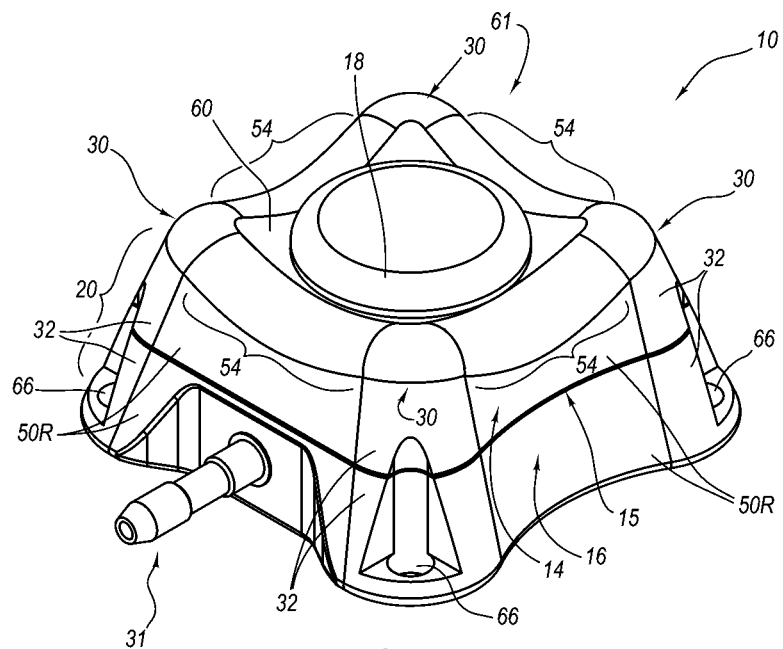
FIG. 15A shows a perspective view of an embodiment of an access port according to the instant disclosure.
Figure 15B:
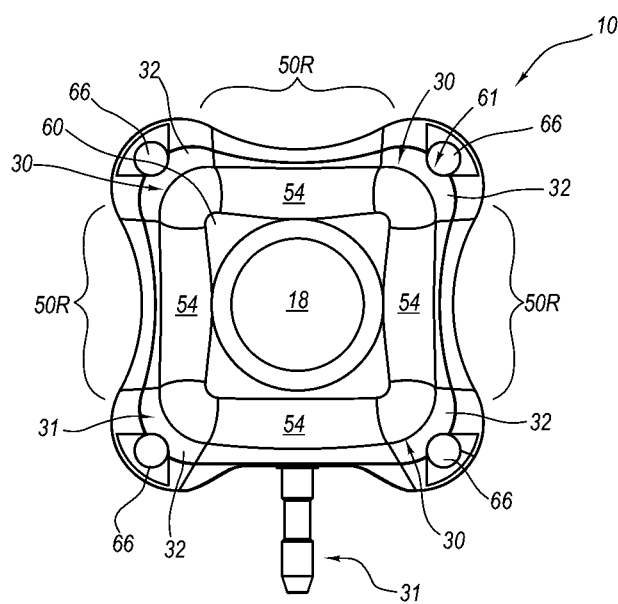
FIG. 15B shows a top elevation view of the access port shown in FIG. 15A.

In a further embodiment of an access port contemplated by the instant disclosure, FIGS. 15A and 15B show a perspective view and a top elevation view, respectively, of an access port 10 generally configured as is described with reference to FIG. 5 but may include at least one nonplanar side surface. In another embodiment, access port 10 as shown in FIG. 15 may be configured as shown in FIGS. 1-4 or FIGS. 6-7, or any embodiments described hereinbelow, without limitation.

Figure 16:
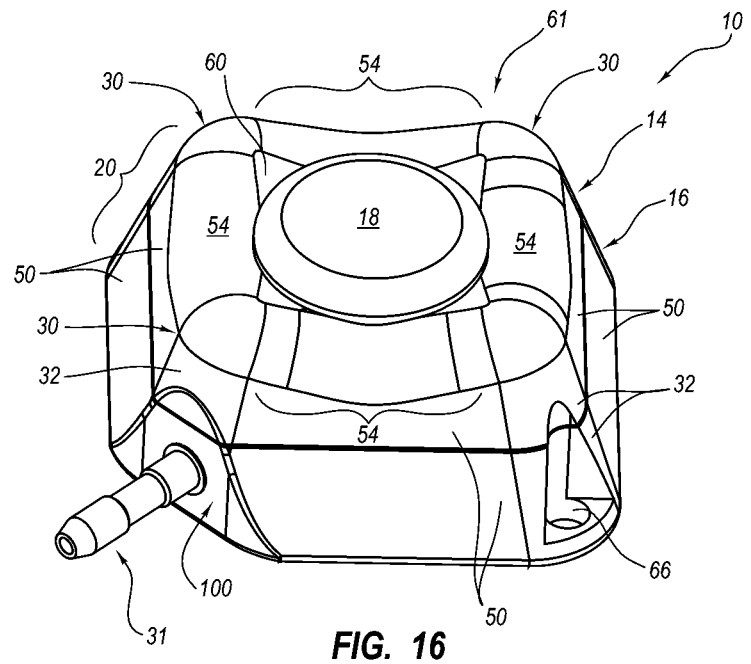
FIG. 16 shows a perspective view of an access port according to the instant disclosure.

More specifically, elongated body 20 of access port 10, as shown in FIGS. 15A and 15B, includes three side surfaces 50R that extend arcuately (as shown in FIG. 15B). Such a configuration may provide an access port 10 that is identifiable subsequent to implantation. In yet another embodiment of an access port contemplated by the instant disclosure, FIG. 16 shows a perspective view of an access port 10 including a side wall 100 that truncates a portion of a radius 32 formed between side surfaces 50 of access port 10. It may also be noted that such an access port 10 may include three suture apertures 66, which may, taken alone or in combination with at least one other feature, comprise at least one identifiable feature of an access port contemplated by the instant disclosure. In addition, as shown in FIG. 16, outlet stem 31 may extend from side wall 100.

Figure 17:
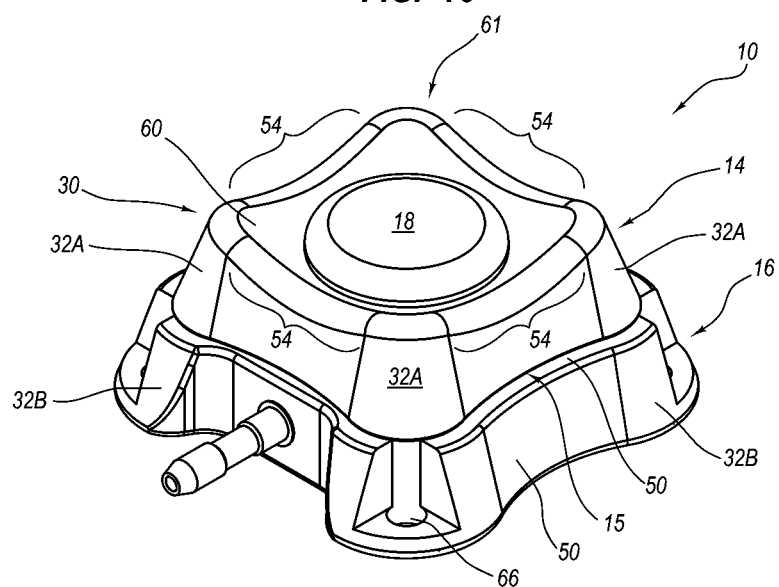
FIG. 17 shows a perspective view of an access port according to the instant disclosure.

In a further embodiment of an access port contemplated by the instant disclosure, FIG. 17 shows a perspective view of an access port 10 wherein cap 14 and base 16, when assembled to one another along mating line 15, form a flange feature or lip feature 102 that extends about at least a portion of the periphery of the access port 10. As shown in FIG. 17, lip feature 102 extends substantially about the periphery of the access port 10, proximate to the mating line 15 between cap 14 and base 16. Such a feature may comprise at least one identifiable feature of an access port contemplated by the instant disclosure. Thus, it may be appreciated that a peripheral discontinuity between the cap 14 and base 16 may be formed generally along the mating line 15 therebetween. In the embodiment of an access port as shown in FIG. 7, an overhanging rim feature 76 may comprise a peripheral discontinuity or, in the embodiment of an access port as shown in FIG. 17, a lip feature 102 may comprise a peripheral discontinuity.

Figure 18:
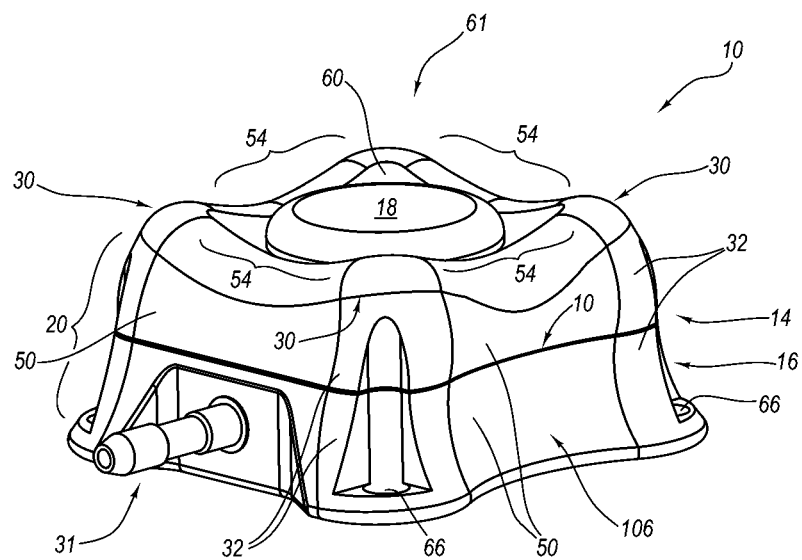
FIG. 18 shows a perspective view of an access port according to the instant disclosure.

In a further embodiment of an access port contemplated by the instant disclosure, FIG. 18 shows a perspective view of an access port 10 wherein at least a portion of at least one side surface 50 is concave. As shown in FIG. 18, concave region 106 of side surface 50 is concave. Concavity (i.e., a concave region 106) may be exhibited over at least a portion of a side surface of an access port of any of the embodiments as shown herein, without limitation. Thus, at least one side surface 50 of an access port contemplated by the instant disclosure having at least at least a portion thereof that is concave is one exemplary example of at least one perceivable feature for identification of an access port contemplated by the instant disclosure.

In a further embodiment of an access port contemplated by the instant disclosure, FIG. 18 shows a perspective view of an access port 10 wherein at least a portion of at least one side surface 50 is concave. As shown in FIG. 18, region 106 of side surface 50 is concave. Concavity may be exhibited over at least a portion of a side surface of an access port of any of the embodiments as shown herein, without limitation. Thus, at least one side surface 50 of an access port contemplated by the instant disclosure having at least at least a portion thereof that is concave is one exemplary example of at least one perceivable feature for identification of an access port contemplated by the instant disclosure.

Figure 19:
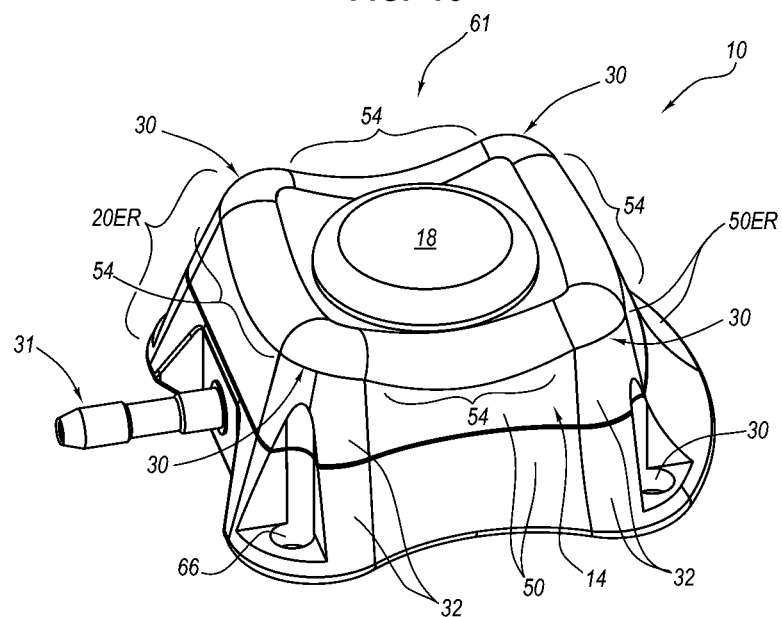
FIG. 19 shows a perspective view of an access port according to the instant disclosure.

In a further embodiment of an access port contemplated by the instant disclosure, FIG. 19 shows a perspective view of an access port 10 generally configured as is described with reference to FIGS. 6A and 6B. More specifically, elongated body 20ER, as shown in FIG. 19 includes a side surface 50ER that extends arcuately from upper topography 61 of access port 10 downwardly (i.e., toward reference plane 11 as shown in FIGS. 1A and 1B). Such a configuration may provide an elongated body 20E of an access port 10 having an elongated side portion.

It should be understood from the above-described various embodiments of an access port contemplated by the instant disclosure that many variations, additions, or different features may be encompassed by the instant disclosure. Thus, the instant disclosure is not limited to the several above-described exemplary embodiments.

Figure 20:
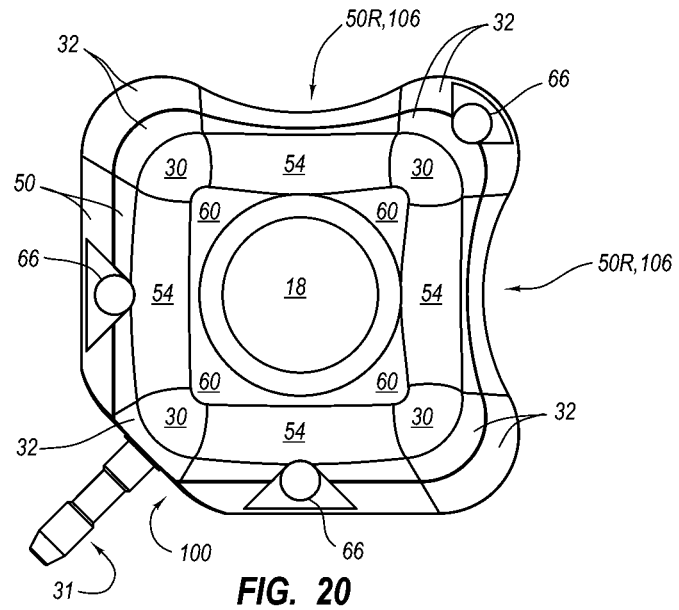
FIG. 20 shows a perspective view of an access port according to the instant disclosure.

For example, as shown in FIG. 20, which shows a top elevation view of an access port 10 contemplated by the instant disclosure, an access port 10 may include a side wall 100 that at least partially truncates a radius 32 between side surfaces 50, outlet stem 31 extending from side wall 100, and at least one of a concave region 106 and an arcuate surface 50R. Further, as shown in FIG. 20, suture apertures 66 may be positioned so as to identify the access port 10 after subcutaneous implantation.

Figure 21:
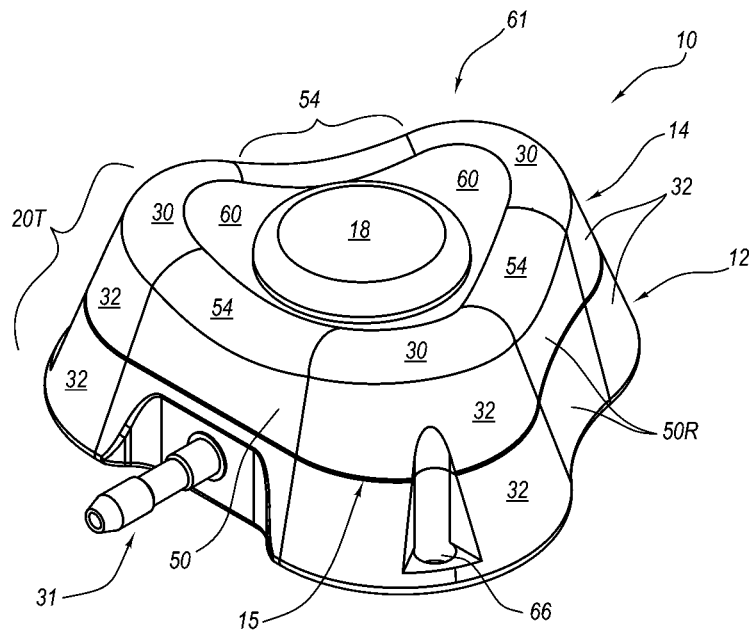
FIG. 21 shows a perspective view of an access port according to the instant disclosure.

Additionally, the instant disclosure contemplates access ports having an exterior geometry that is polygonal in nature. Specifically, the instant disclosure contemplates that an access port contemplated by the instant disclosure may exhibit a generally triangular exterior. Thus, as shown in FIG. 21, body 20 may exhibit a generally pyramidal or tapered shape (i.e., a polygonal base having surfaces for each side of the polygon extending toward a common vertex). Generally, a body 20T of an access port 10 may extend between a generally triangularly-shaped base and a relatively smaller, generally triangularly-shaped upper base. Accordingly, the exterior of access port 10 may be substantially defined by three side surfaces (e.g., 50, 50R, 102, 50E) having radiuses 32 extending therebetween. In addition, the upper topography 61 of access port 10 may be defined by upper surface 60 in combination with side regions 54 and rounded corner regions 30. Such a configuration may provide an access port having at least one feature that may be perceived by palpation.

Figure 22:
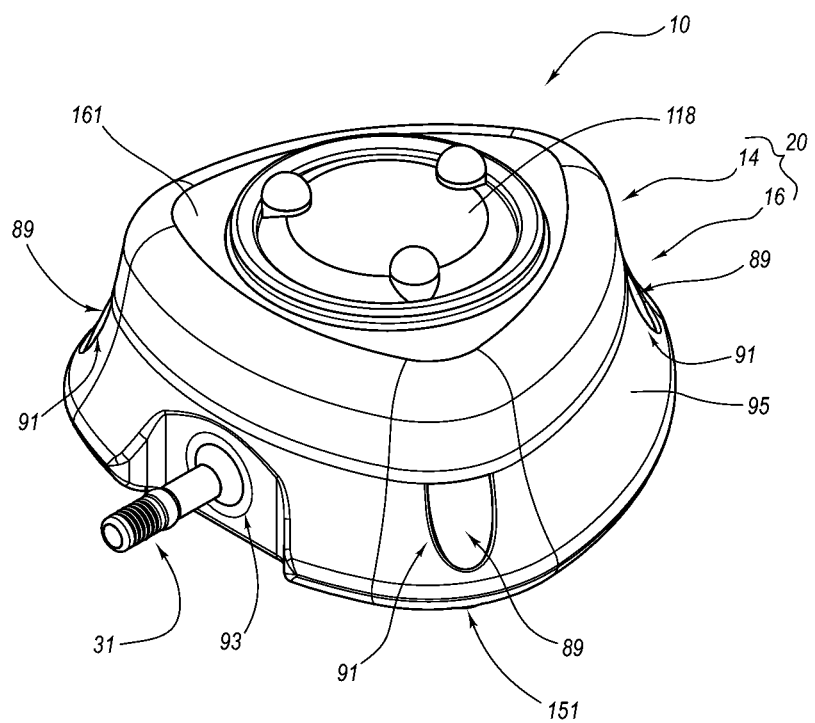
FIG. 22 shows a perspective view of another embodiment of an access port according to the instant disclosure.
Figure 23:
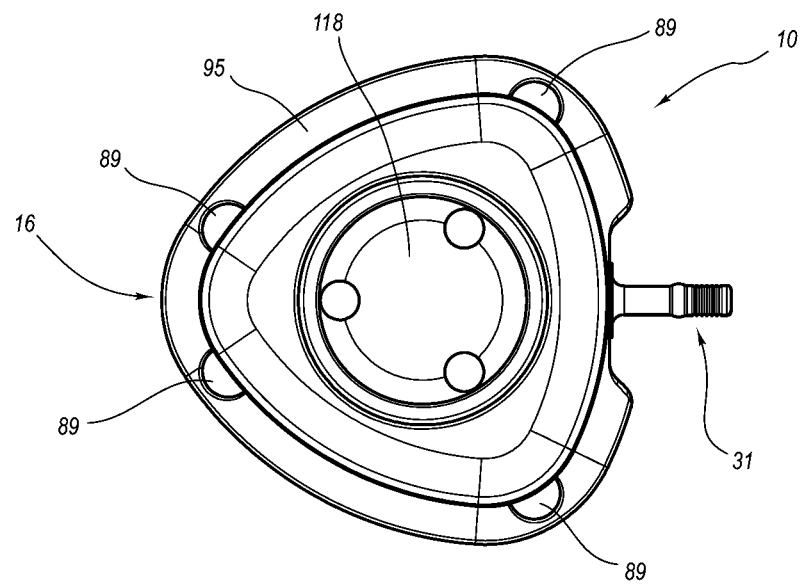
FIG. 23 shows a top elevation view of the assembled access port shown in FIG. 22.

FIGS. 22 and 23 show a perspective view and a top elevation view of another embodiment of an access port including a generally triangular exterior geometry. More particularly, as shown in FIGS. 22 and 23, a cap 14 and base 16 (collectively forming a housing) may capture a septum 118 to form an access port 10. Further, outlet stem 31 may include a stem base that may be positioned within and sealed to an outlet recess 93 formed within base 16. The outlet stem 31 may be in fluid communication with a cavity formed within the access port 10. Optionally, suture plugs 89 may be positioned within suture cavities 91 formed in base 16. Suture plugs 89 may comprise a pliant material (e.g., silicone, rubber, etc.) that may provide some resilience between sutures coupling the access port 10 (i.e., the base 16) to a patient. In further detail, a side periphery 95 (e.g., one or more side walls) of access port 10 may be generally triangular. Thus, cap 14 and base 16 may collectively form a generally triangular housing or body of access port 10. Also, the instant disclosure contemplates that side periphery 95 may increase or decrease in cross-sectional size (e.g., by tapering or arcuately transforming) between upper surface 161 of cap 14 and lower surface 151 of base 16. As shown in FIGS. 22 and 23, a transverse cross section (taken in a selected plane substantially parallel to lower surface 151 of base 16) of access port 10 may be larger proximate to lower surface 151 of base 16 and may be relatively smaller proximate upper surface 161 of cap 14.

Figure 24:
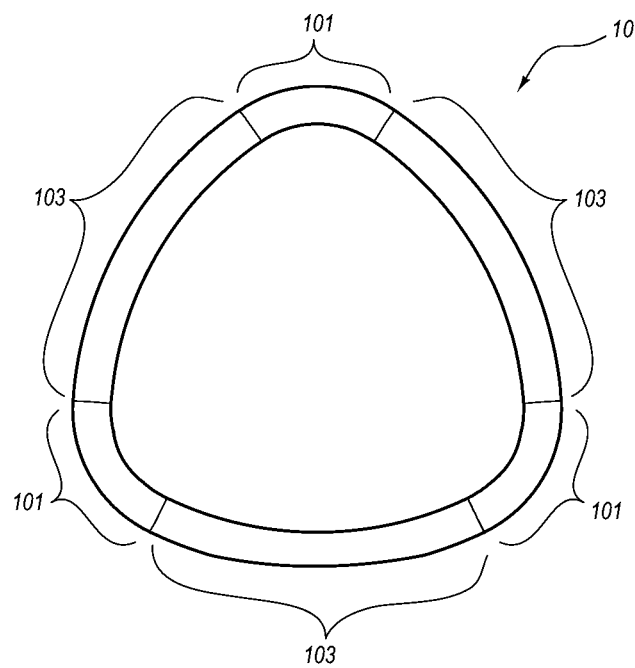
FIG. 24 shows a simplified representation of a transverse cross section of the access port shown in FIGS. 22 and 23.
Figure 25:
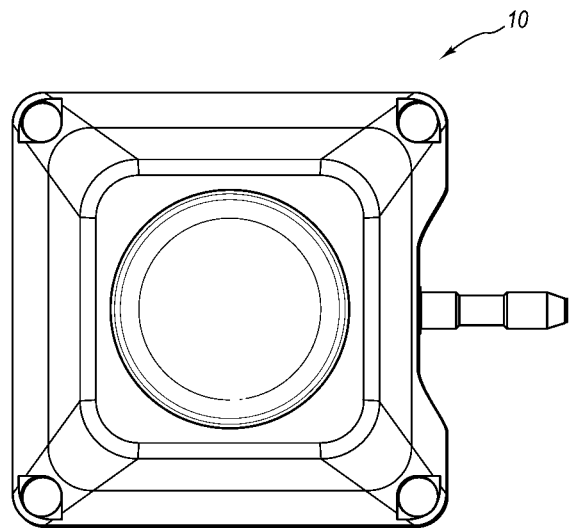
FIGS. 25-51 show perspective views of additional embodiments of an access port.
Figure 26:
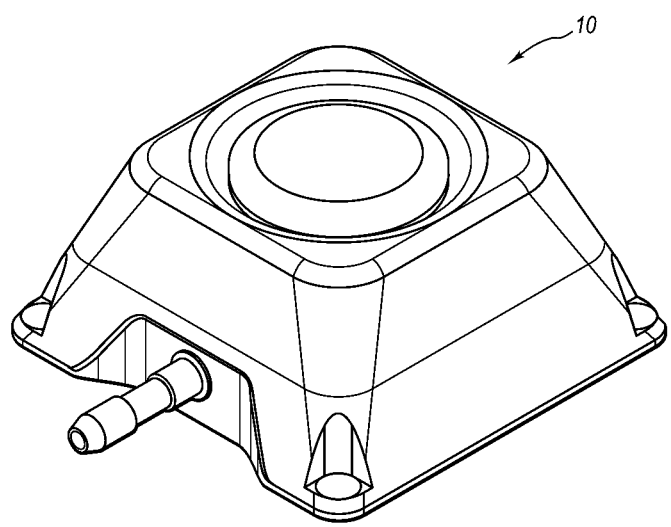
Figure 27:
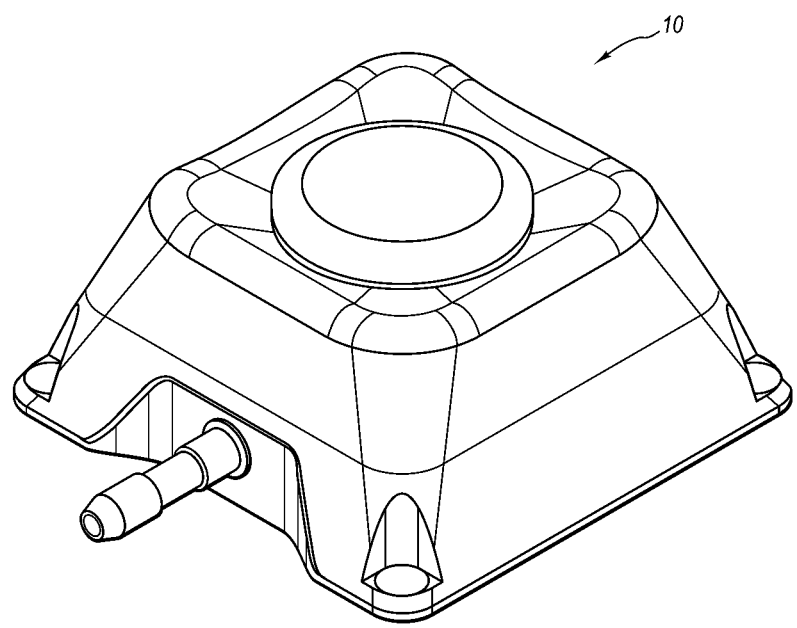
Figure 28:
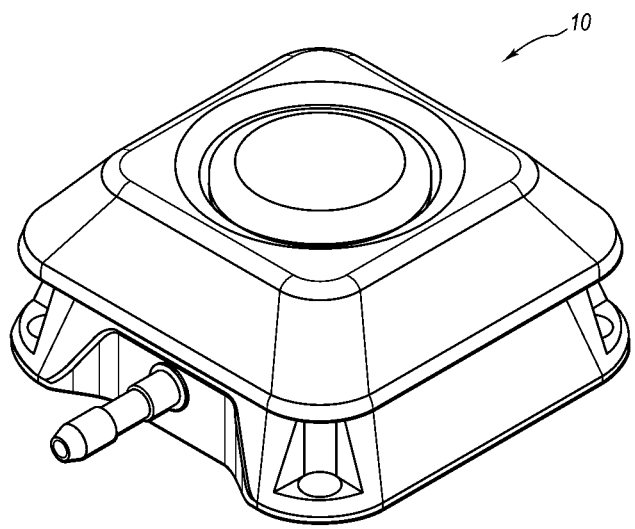
Figure 29:
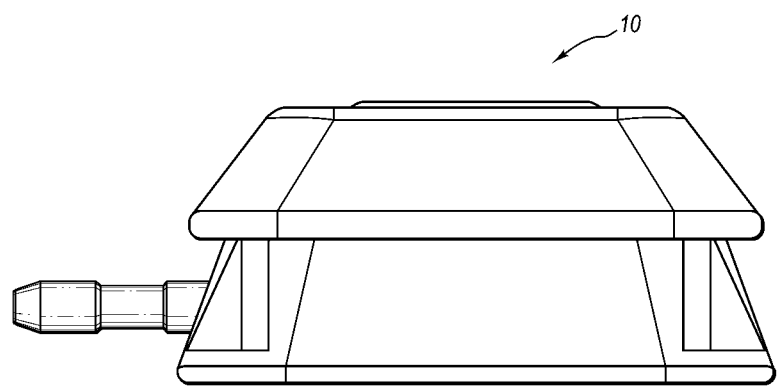
Figure 30:
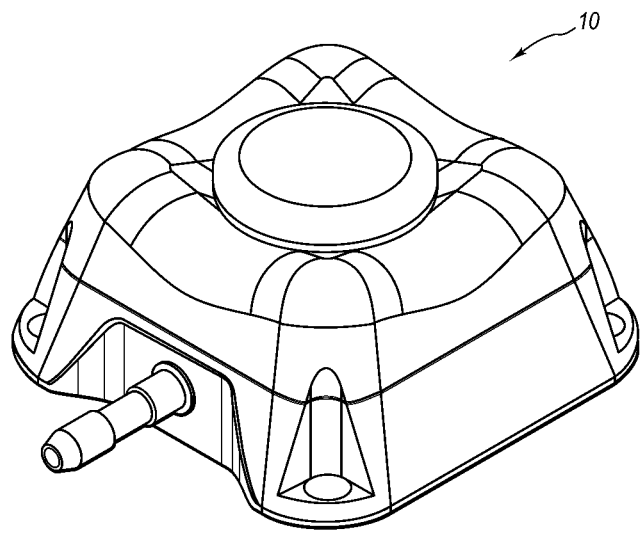
Figure 31:
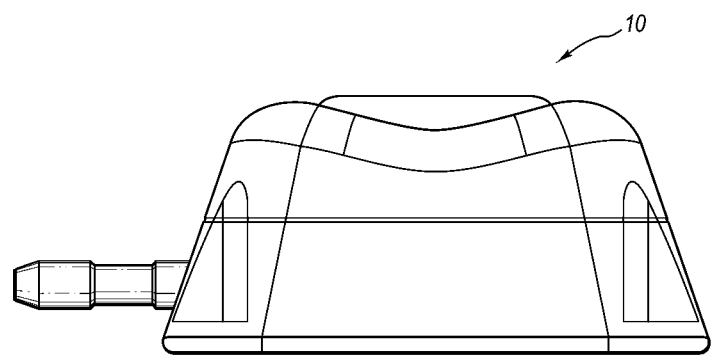
Figure 32:
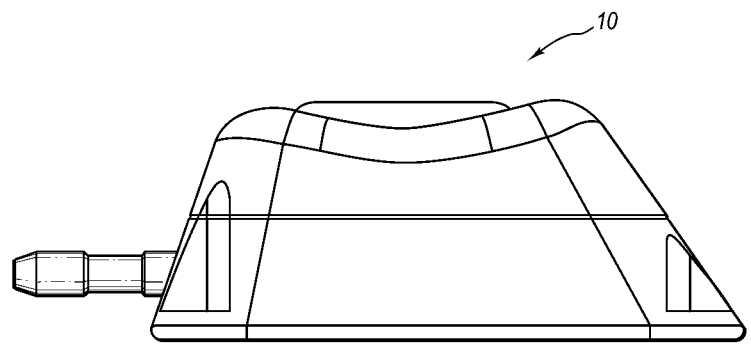
Figure 33:
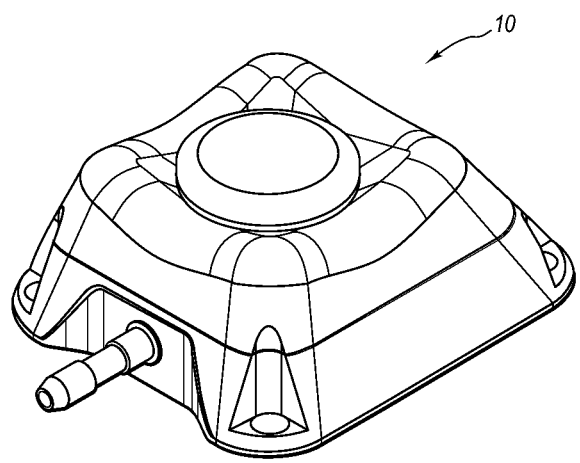
Figure 34:
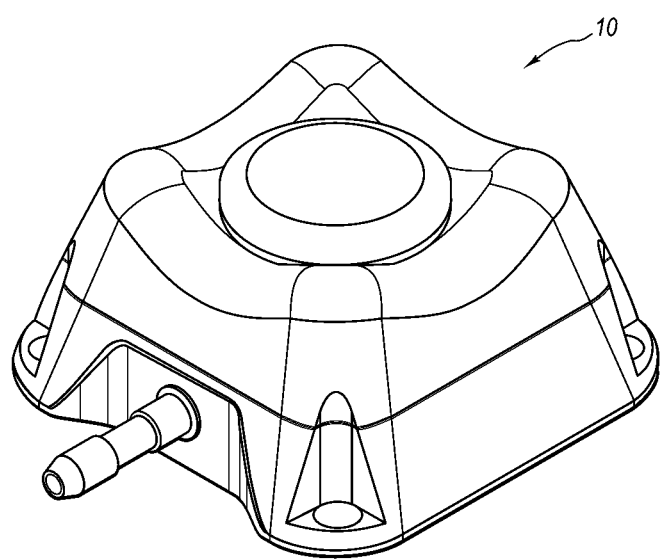
Figure 35:
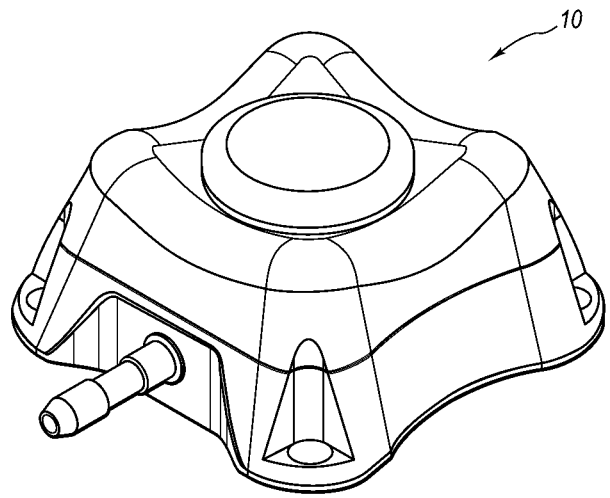
Figure 36:
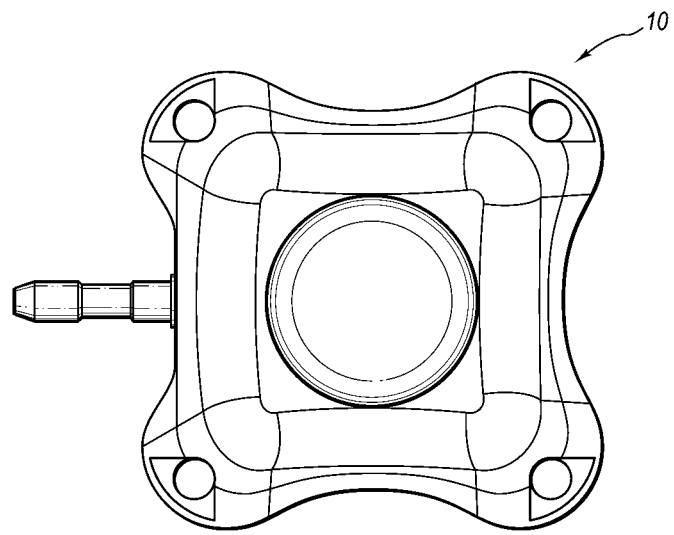
Figure 37:
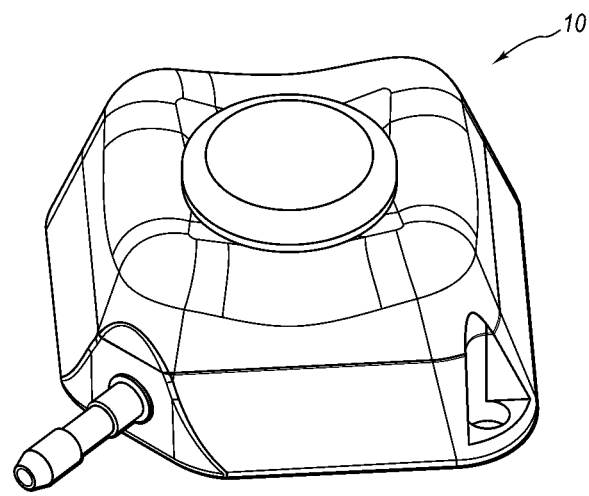
Figure 38:
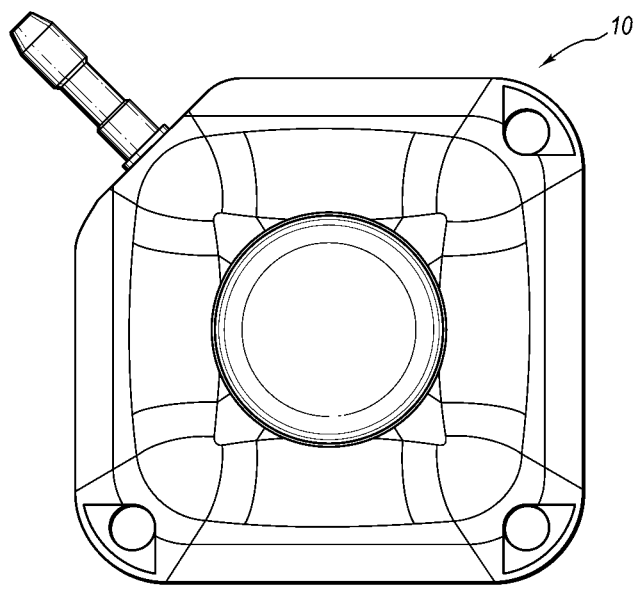
Figure 39:
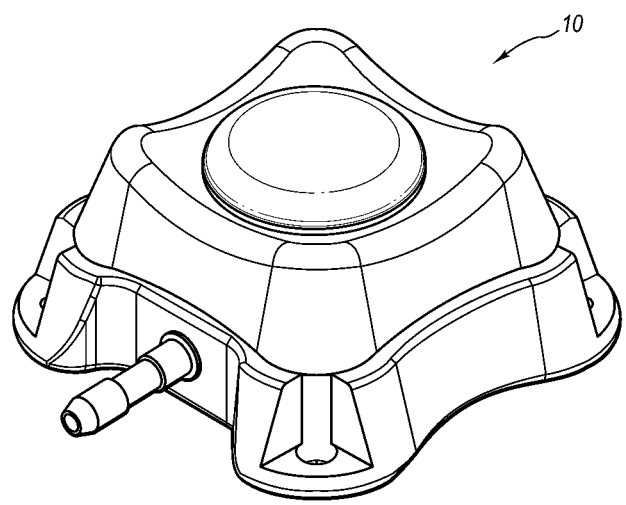
Figure 40:
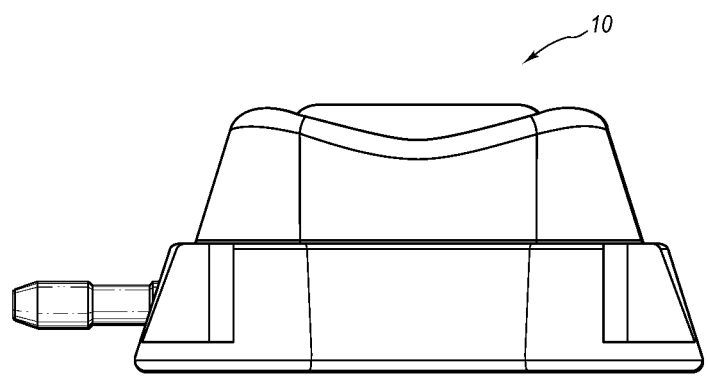
Figure 41:
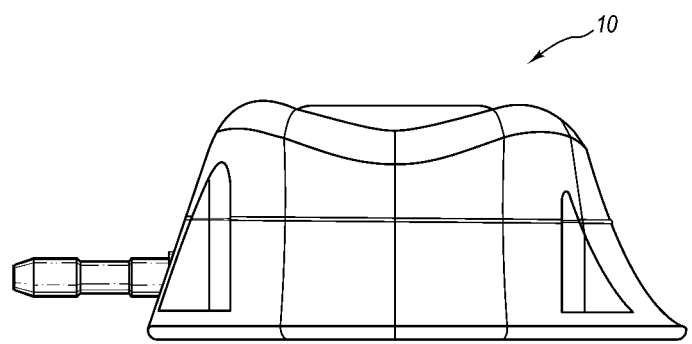
Figure 42:
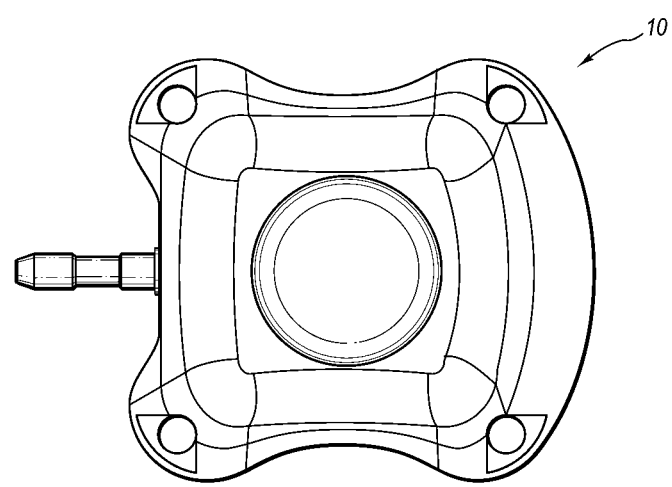
Figure 43:
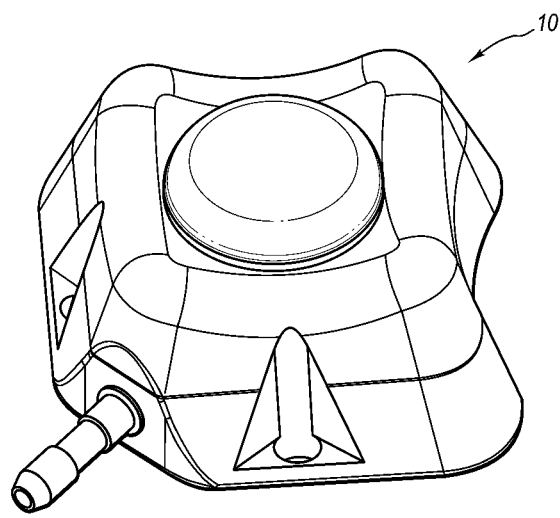
Figure 44:
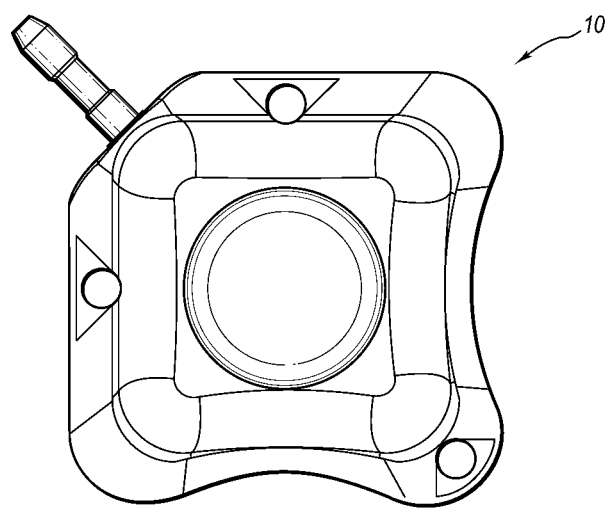
Figure 45:
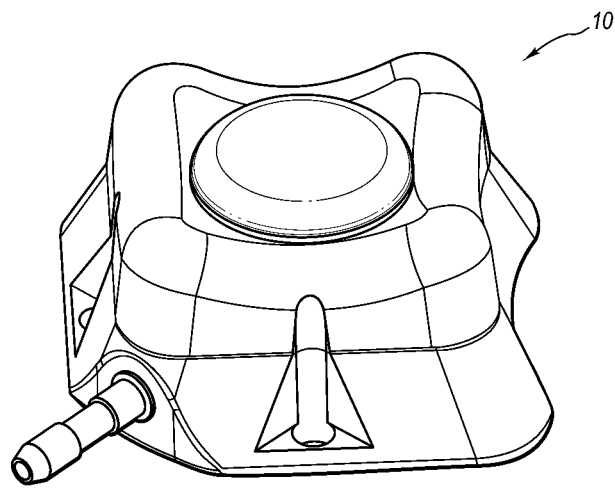
Figure 46:
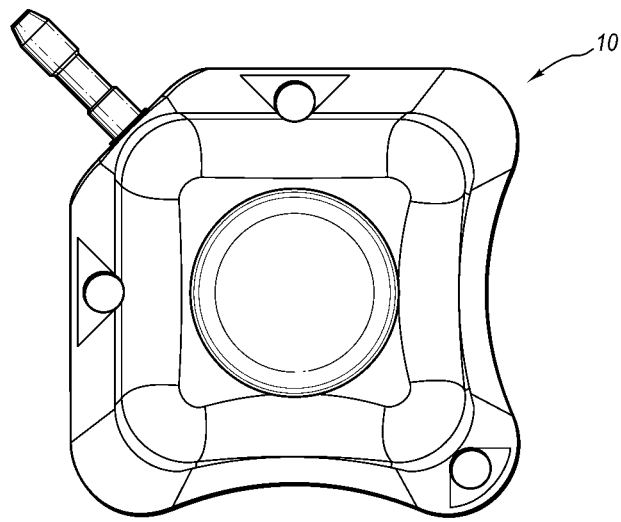
Figure 47:
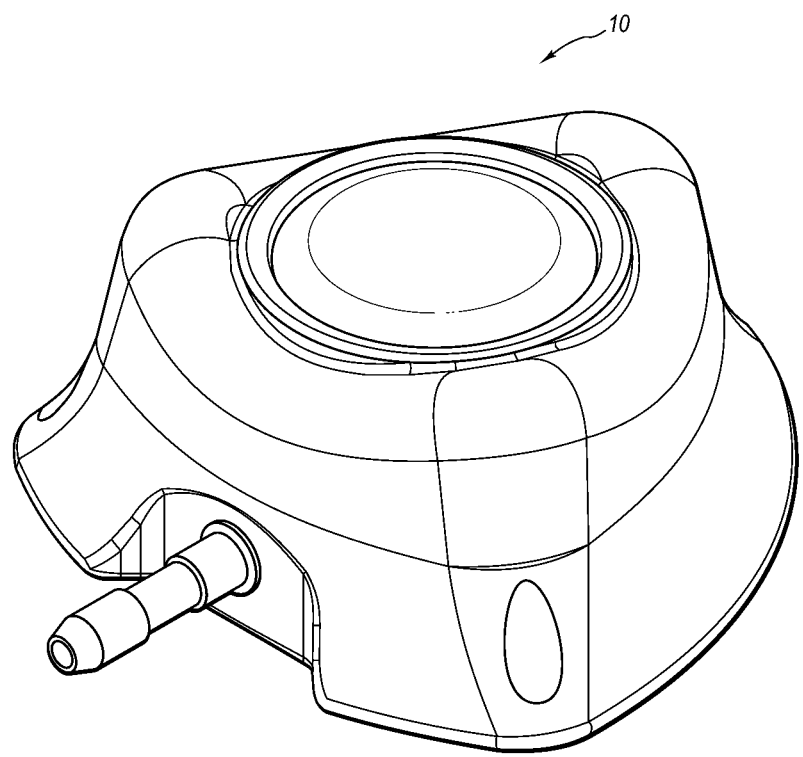
Figure 48:
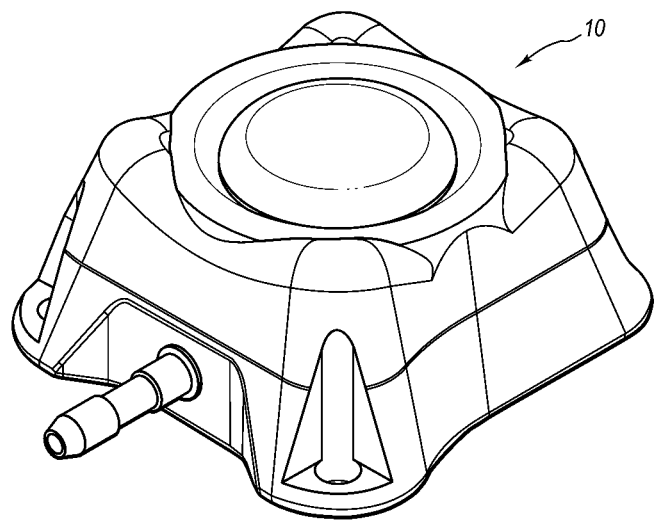
Figure 49:
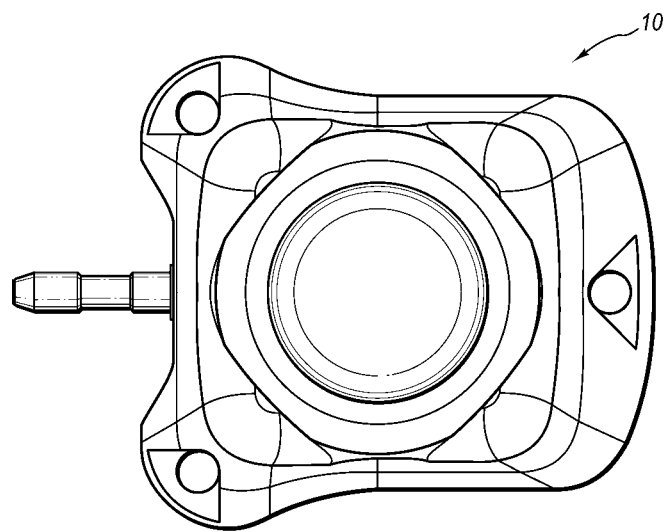
Figure 50:
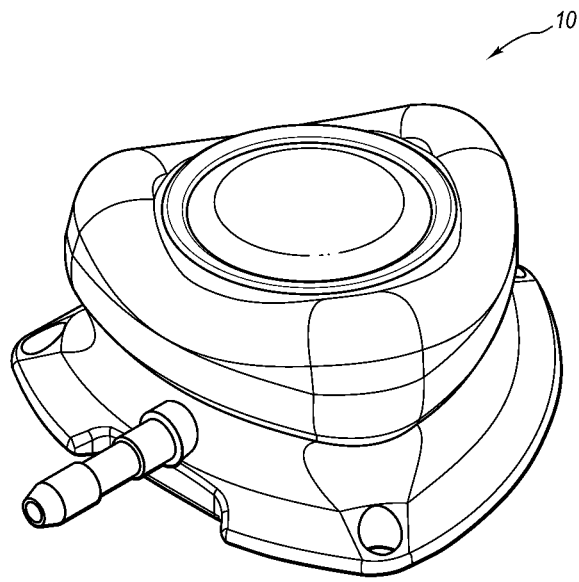
Figure 51:
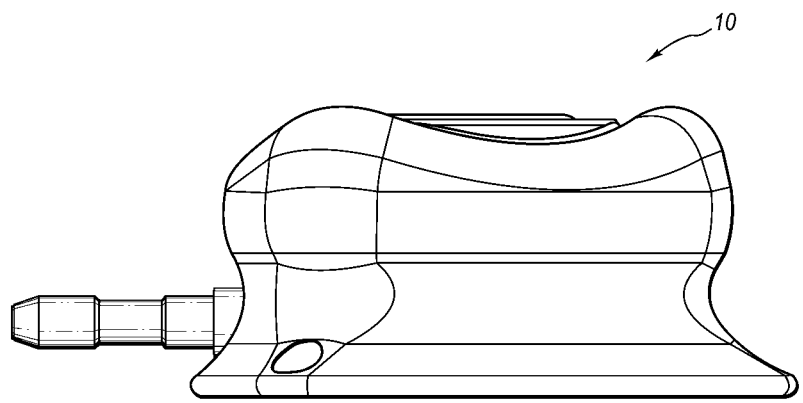

Additionally, FIG. 24 shows a simplified representation of a transverse cross section of access port 10. As shown in FIG. 24, side periphery 95 of access port 10 may define three side regions 103 that extend between associated vertex regions 101. In addition, in one embodiment and as shown in FIG. 24, side periphery 95 may define a substantially equilateral generally triangular shape. As one of ordinary skill in the art will appreciate, side regions 103 may arcuately extend between associated vertex regions 101; thus, side regions 103 may form "sides" of a generally triangular shape. Further, although vertex regions 101 are rounded, it may be appreciated that such vertex regions 101 form an intersection between adjacent side regions 103. Accordingly, one of ordinary skill in the art will appreciate that the phrase "generally triangular," as used herein, encompasses any generally three-sided geometry wherein adjacent sides intersect, without limitation. For example, the phrase "generally triangular" encompasses three sided polygons, circular triangles, equilateral triangles, etc., without limitation.

The instant disclosure also contemplates that at least one feature of an access port contemplated by the instant disclosure may not be observable visually or by palpation but, rather, may be otherwise observable. For example, the instant disclosure contemplates that at least one feature of an access port may be observable through interaction with an imaging technology such as x-ray or ultrasound. For example, in one embodiment, a metal feature (e.g., a plate or other metal geometry) may be included by an access port contemplated by the instant disclosure. As may be appreciated, such a metal feature may be represented on an x-ray generated by exposure of the access port to x-ray energy while simultaneously exposing x-ray sensitive film to x-ray energy passing through the access port. Further, the instant disclosure contemplates that a size, shape, or both size and shape of a metal feature of an access port may be configured for enhancing identification of an access port. For example, assuming that a metal feature comprises a metal plate, a size, shape, or both may be selectively tailored for identification of an access port. Similarly, a feature of an access port contemplated by the instant disclosure may be tailored for detection via ultrasound interaction. Such a feature may comprise an exterior topographical feature. In another embodiment, such a feature may comprise a composite structure including two or more materials that form an interface surface that may be identified by ultrasound imaging.

Figure 52:
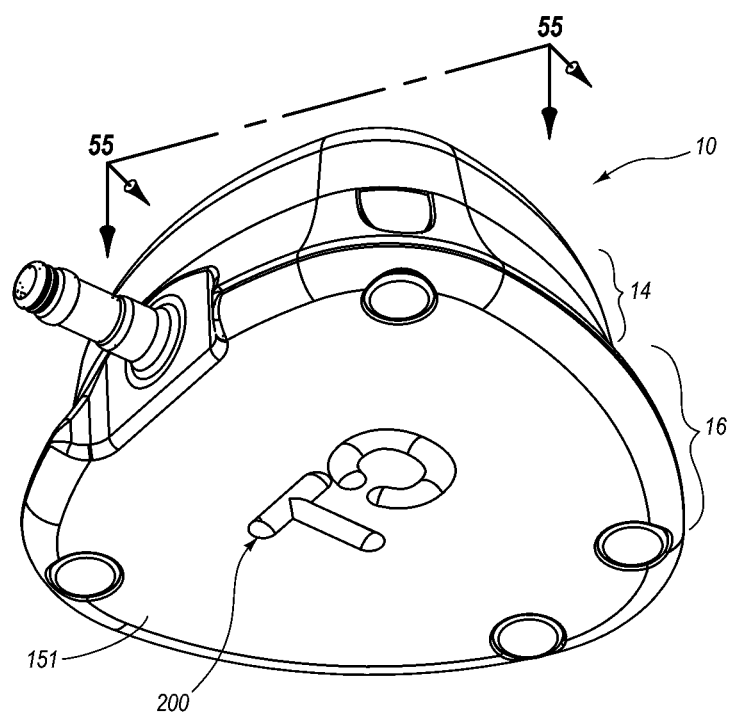
FIG. 52 shows a bottom perspective view of an access port according to one embodiment.
Figure 53A:
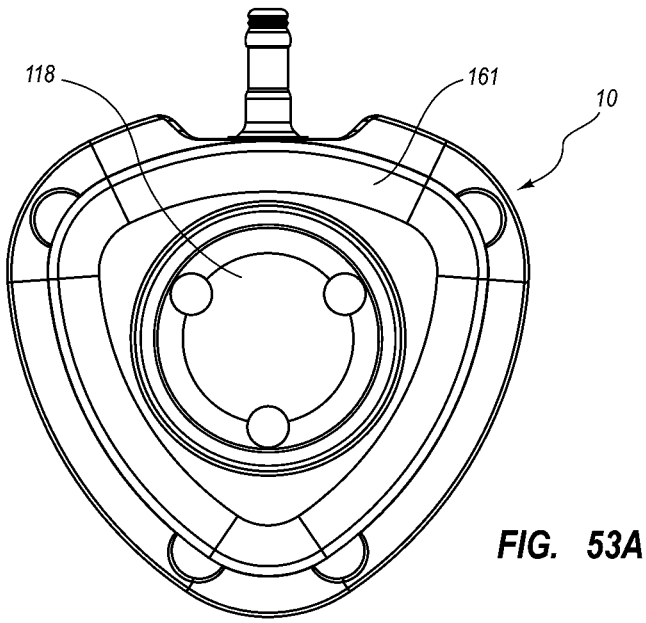
FIG. 53A shows a top view of the access port shown in FIG. 52.
Figure 53B:
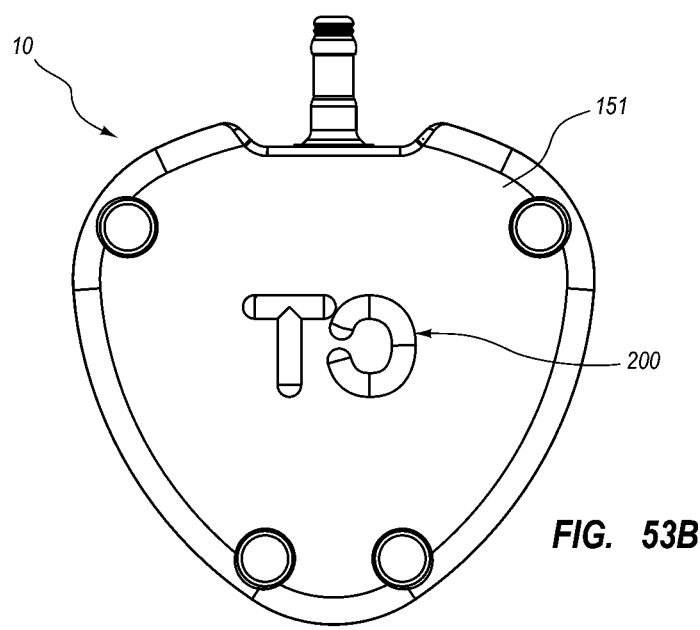
FIG. 53B shows a bottom view of the access port shown in FIG. 52.

One example embodiment of a feature observable through interaction with imaging technology contemplated by the instant disclosure is shown in FIGS. 52, 53A, and 53B. FIG. 52 depicts a bottom perspective view of an access port 10. FIG. 53A shows a top view of the access port 10, while FIG. 53B shows a bottom view of the access port. The access port 10 of FIGS. 52, 53A, and 53B is similar in some respects to the access port 10 as seen in FIGS. 22 and 23, including a cap 14 and a base 16 that cooperate to define a body. In the present example embodiment, however, the lower surface 151 of the base 16 includes an identification feature 200, as seen in FIGS. 52 and 53B. It is contemplated that the identification feature 200 can be one or more alphanumeric characters, such as the "CT" depicted. Additionally, the instant disclosure contemplates the use of other markings, such as one or more symbols, patterns, characters, designs, a combination thereof, etc. The identification feature 200 can be of any size, shape, or both in order to tailor the identification feature for the specific identification of one or more of a variety of characteristics of the access port. Specifically, in one embodiment the identification feature 200 can convey information to a practitioner regarding the power-injectability of the implanted access port. Note that in the present embodiment, the identification feature 200 is defined as a recessed feature, whereas in other embodiments the identification feature may be defined in other ways, as discussed hereafter.

As mentioned above, FIG. 53A depicts a top view of the access port 10. Note that the identification feature 200 is not observable through the upper surface 161 of the cap 14 or through the septum 118 without the interaction of imaging technology. As seen in FIG. 53B, the alphanumeric characters of the identification feature 200, "CT," are engraved mirror-reversed on the lower surface 151 of the base 16. The "CT" is engraved mirror-reversed so that when imaging technology, such as x-ray imaging, is used to identify a subcutaneously implanted access port, the "CT" will be visible in the proper orientation. By engraving a desired identification feature mirror-reversed on the bottom surface of an access port, a practitioner will be able to determine if there is a problem with the port after implantation, such as if the access port has flipped or otherwise become mis-oriented while in the body of the patient. Thus, if the identification feature is seen mirror-reversed or askew in an x-ray image, the practitioner can correct the problem before attempts are made to use the access port.

Figure 54A:
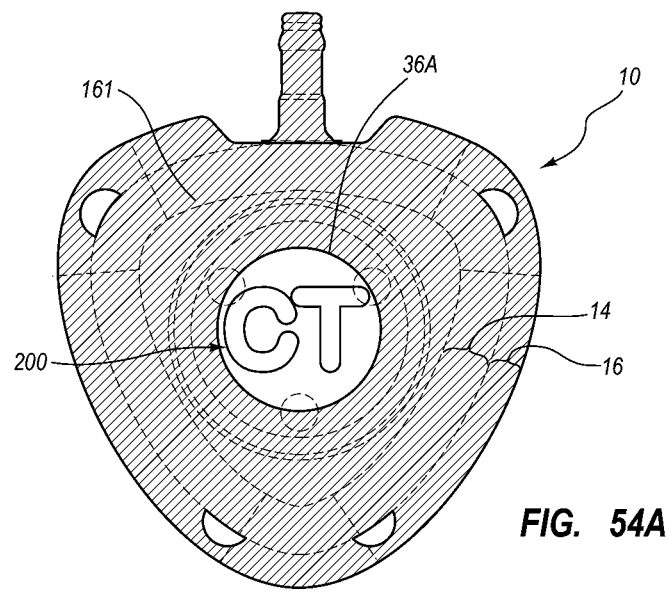
FIG. 54A represents a radiographic image of the access port shown in FIG. 52 when viewed from above the access port.
Figure 54B:
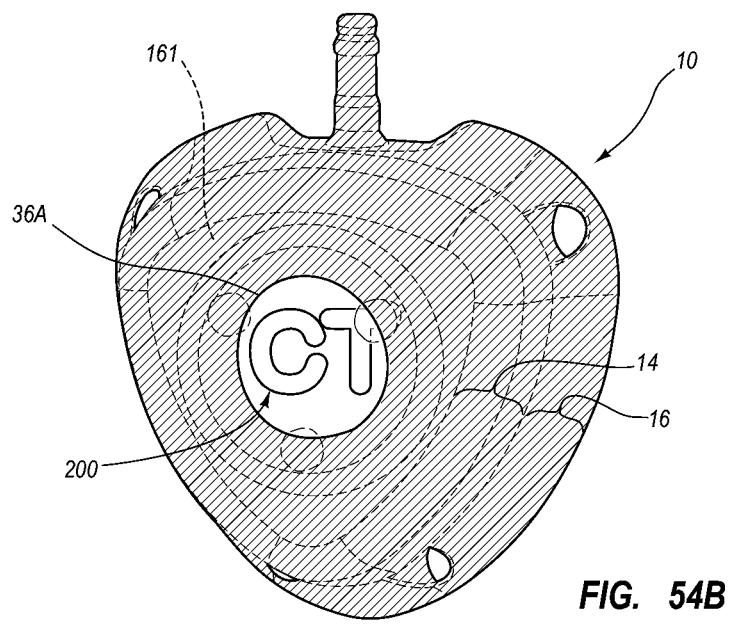
FIG. 54B represents a radiographic image of the access port shown in FIG. 52 when viewed at an angle of approximately 20 degrees.
Figure 54C:
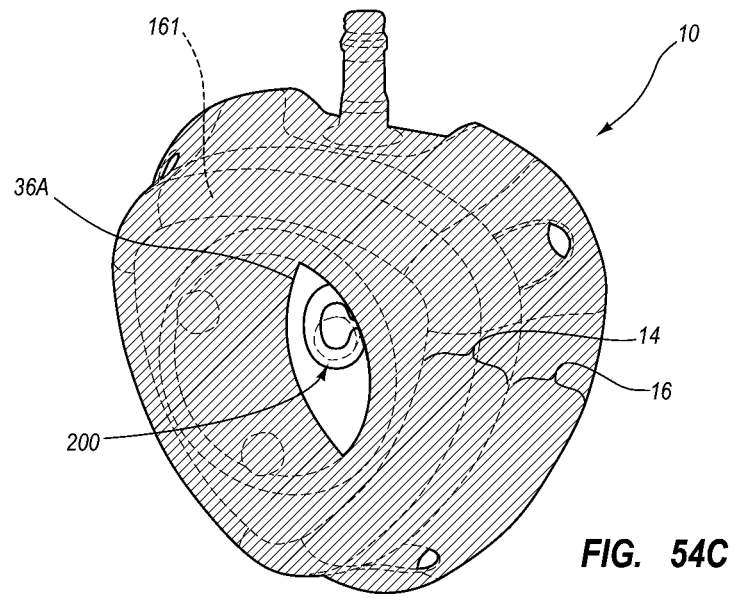
FIG. 54C represents a radiographic image of the access port shown in FIG. 52 when viewed at an angle of approximately 50 degrees.
Figure 55:
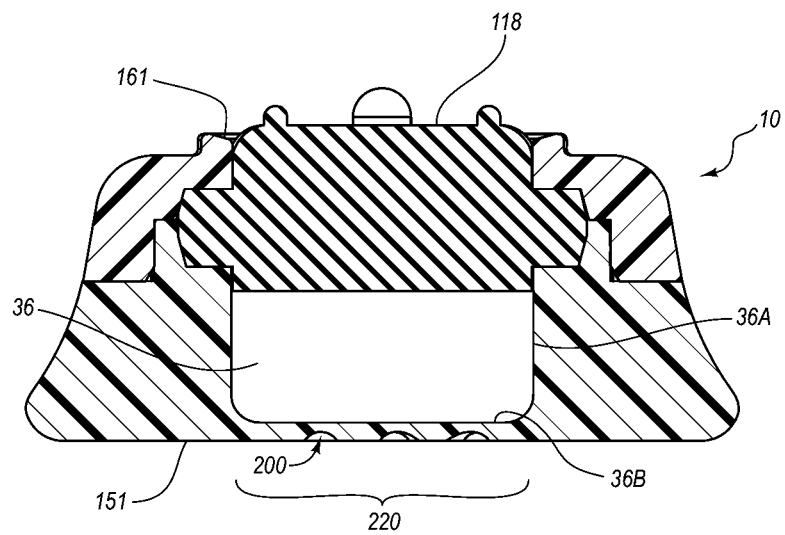
FIG. 55 shows a cross-sectional view of the access port shown in FIG. 52.

Although also useful in access ports where only a portion of a port includes a metallic material, e.g., a metal plate, the engraving technique is well-suited in one embodiment for access ports that are composed of solid metal, such as titanium, stainless steel, or other materials that are typically radiopaque, i.e., non-transmissive to x-rays in sufficient thickness. FIGS. 54A-54C are representative images of the access port 10 of FIG. 52, which includes titanium or other metallic material, as seen via x-ray imaging after implantation into the patient. The access port 10 includes the identification feature 200 as seen in FIGS. 52 and 53B. Due to the relative thickness of the access port 10, the material of the base 16 and cap 14 surrounding a cavity periphery 36A of the cavity 36, which is a fluid cavity, is substantially non-transmissive to x-rays and therefore appears relatively dark in the x-ray image of FIG. 54A. However, the material of the access port 10 within the cavity periphery 36A is relatively thinner through a cavity base 220 (as seen in FIG. 55) than through the material of the cap 14 and base 16. Thus, additional thinning of the material when creating the identification feature 200 enables the identification feature to appear relatively more radiographically transmissive than the surrounding material of the cavity base under x-ray imaging. Note that the identification feature 200 in FIG. 54A is visible in the proper orientation, indicating that the access port is not flipped.

FIGS. 54B and 54C are additional representative x-ray images of the identification feature 200 of the access port 10, wherein the access port is tilted at angles of approximately 20 and 50 degrees, respectively. Thus, the identification feature 200 is also useful for determining relative orientation of the access port 10 after implantation.

Figure 56A:
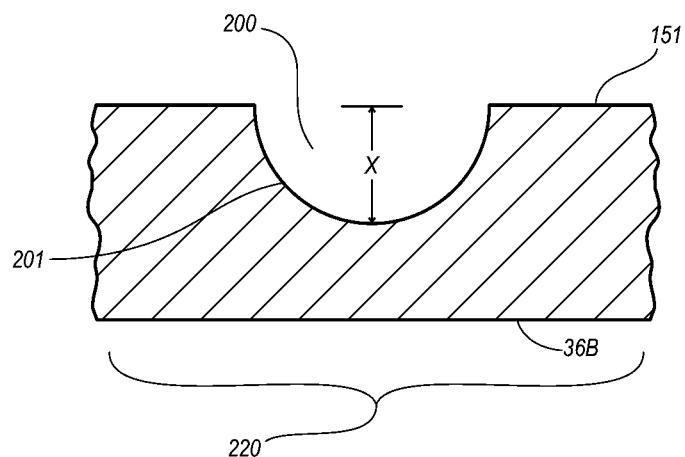
FIGS. 56A and 56B show cross-sectional views of example embodiments of engraved features on an access port surface.
Figure 56B:
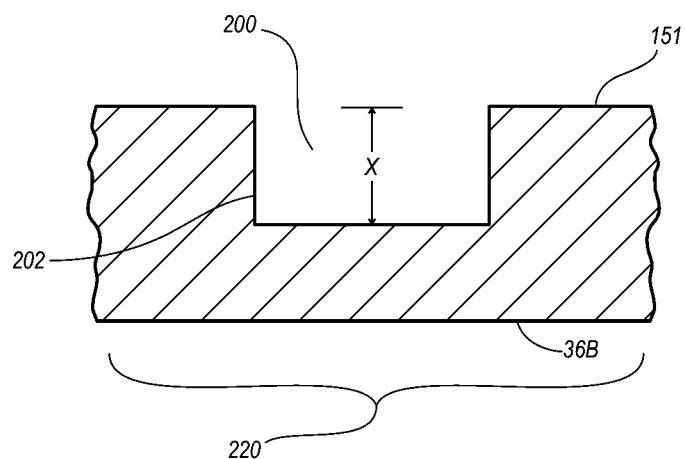

FIG. 55 shows a cross-sectional view taken at line 55-55 of the access port 10 in FIG. 52. In this example embodiment, the identification feature 200 is disposed beneath the septum 118 and the cavity 36. FIGS. 56A and 56B further depict enlarged cross-sectional views of potential cut profiles of the recessed identification feature 200. FIG. 56A shows a rounded engraving profile 201, engraved on the lower surface 151 of the base 16 and used for purposes of aesthetics and ease of manufacturing. For a relatively more defined contrast under imaging technology, however, a sharp-edged engraving profile 202 may be used, as seen in FIG. 56B. Note that a variety of cross-sectional recessed profiles may be employed. This disclosure further contemplates that although engraving is discussed here, other methods of marking the identification feature may be used, such as milling, machining, chemical or laser etching, molding, stamping, etc.

Regardless of the cut profile used, better contrast is achieved generally with greater engraving depth X. The optimal engraving depth X will depend, however, on the thickness of the overall cavity base 220, which is the portion of the base directly below the cavity 36, as shown in FIG. 55. For example, in an embodiment of an access port including titanium, if the overall thickness of the cavity base 220 is approximately 0.020" then sufficient contrast for x-ray imaging purposes can be obtained in one embodiment by engraving the identification feature 200 to a depth X (FIGS. 56A, 56B) of between about 0.009" and about 0.011". In another example embodiment of an access port including titanium, where the overall thickness of the cavity base 220 is approximately 0.030", sufficient contrast can be obtained by engraving the identification feature 200 to a depth X of between about 0.015" and about 0.021". One of ordinary skill in the art will appreciate that the depth of an engraved identification feature can be varied substantially in order to comply with a product's safety requirements and still remain within the scope contemplated by this disclosure. In addition, the depth X of the identification feature can vary according to the position of the feature on the access port, the thickness of material to be penetrated by the imaging technology, the type of material included in the access port, etc.

Figure 57A:
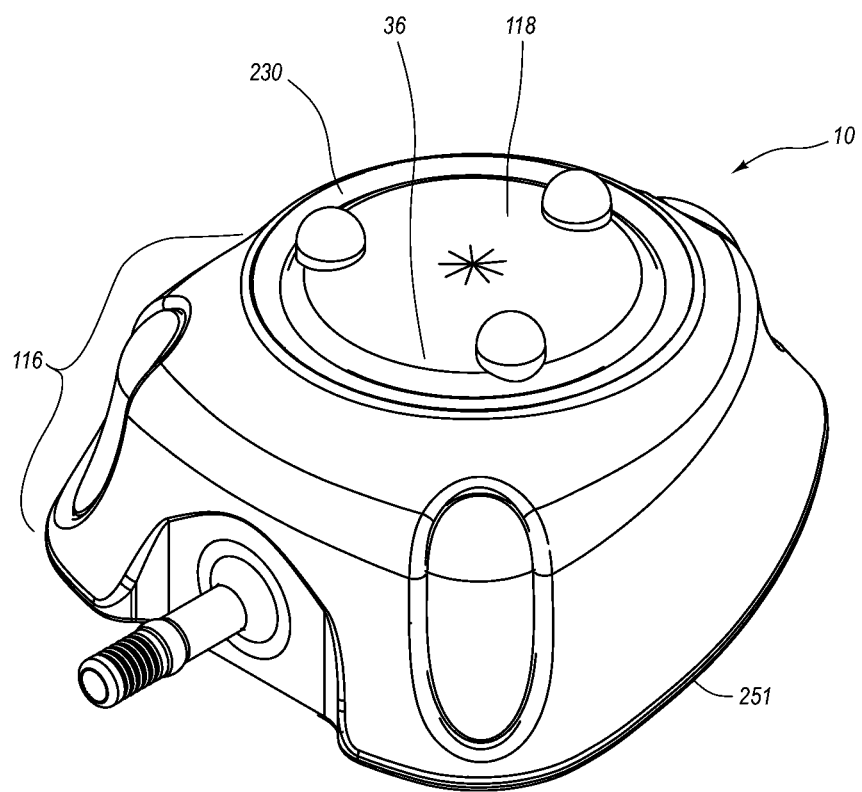
FIG. 57A shows a top perspective view of an access port according to one embodiment.
Figure 57B:
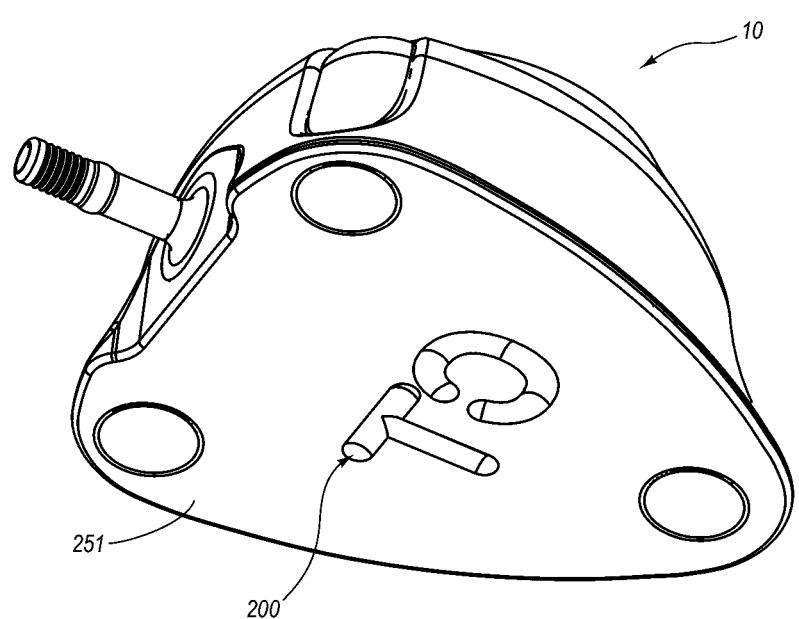
FIG. 57B shows a bottom perspective view of the access port shown in FIG. 57A.
Figure 57C:
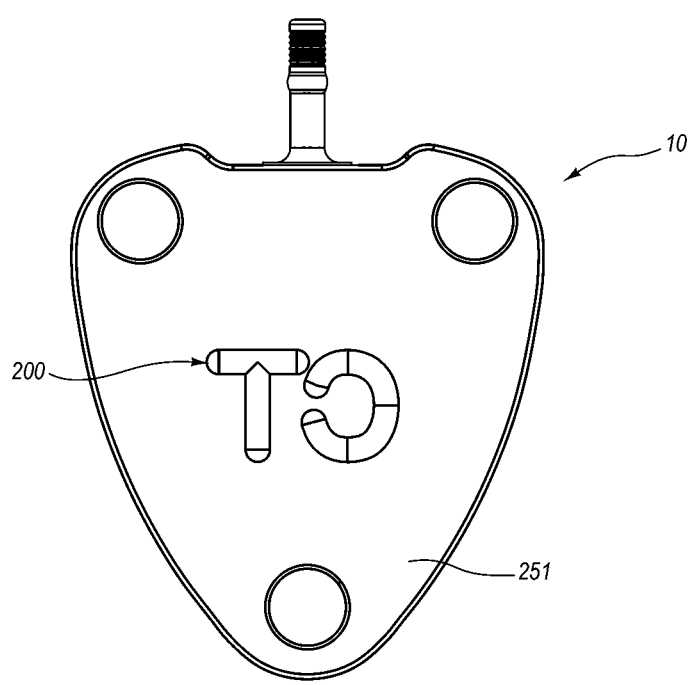
FIG. 57C shows a bottom view of the access port shown in FIG. 57A.
Figure 58A:
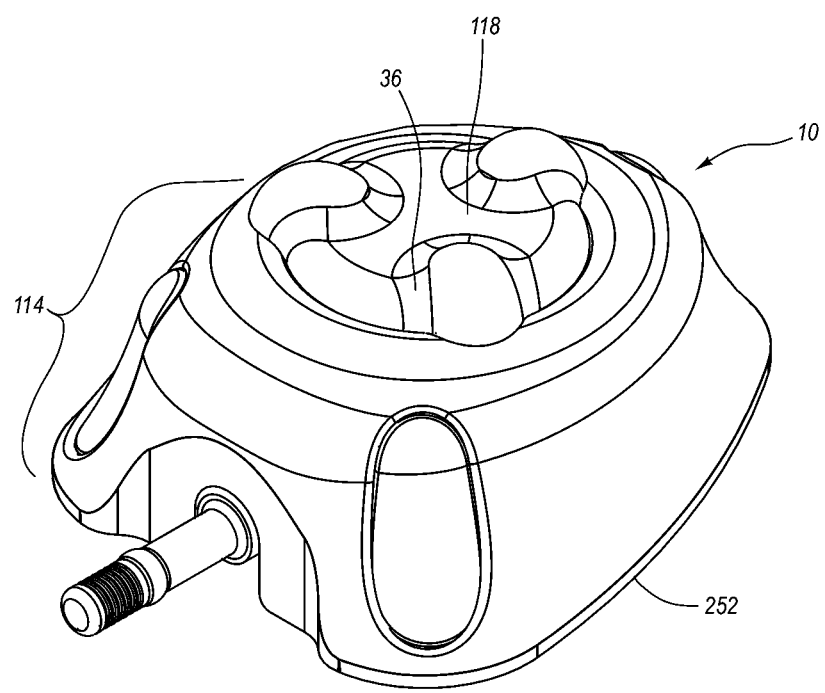
FIG. 58A shows a top perspective view of another embodiment of an access port.
Figure 58B:
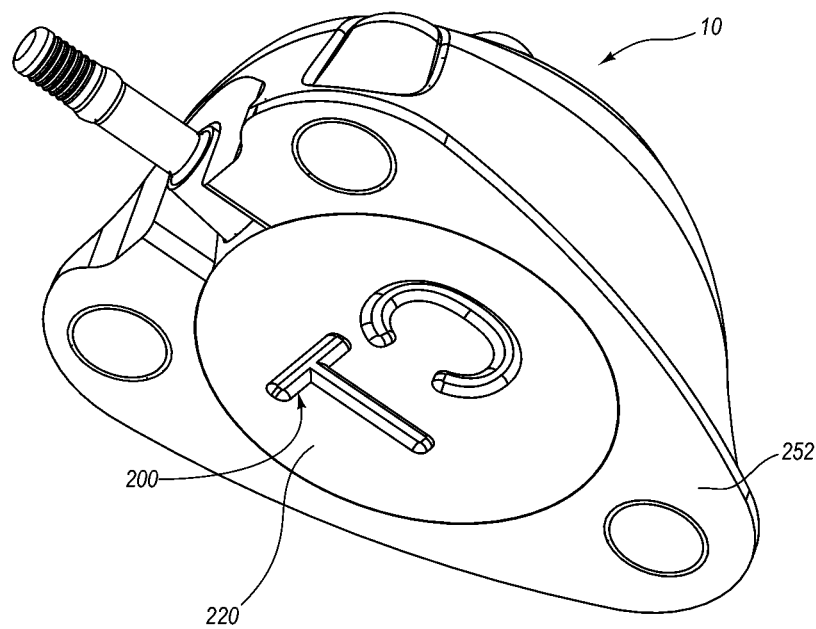
FIG. 58B shows a bottom perspective view of the access port shown in FIG. 58A.
Figure 58C:
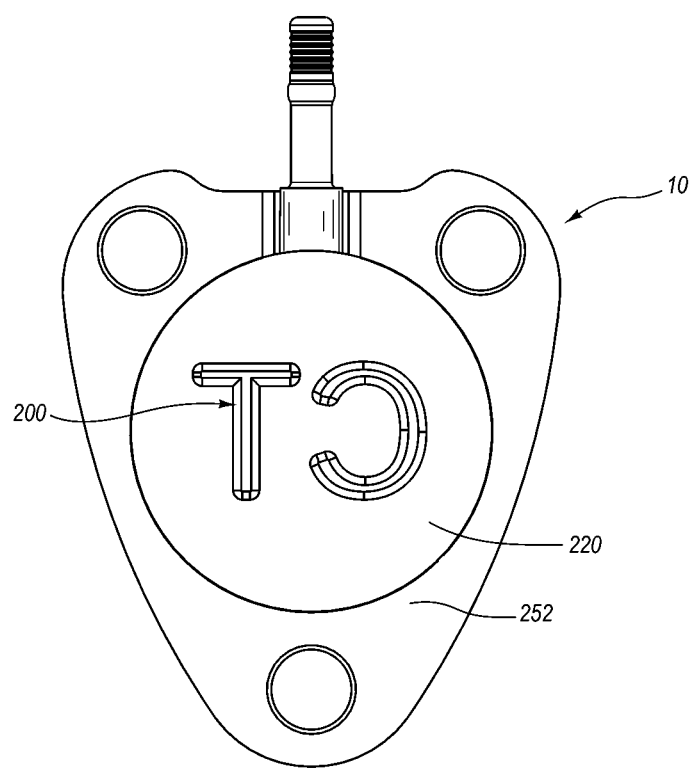
FIG. 58C shows a bottom view of the access port shown in FIG. 58A.

It is also contemplated by this disclosure that the use of an identification feature in a metallic or other radiopaque access port can be applied to access ports having a variety of possible configurations, such as is seen in FIGS. 57A-58C, for example. FIGS. 57A-57C depict one embodiment, wherein the access port 10 includes an identification feature 200 on a lower surface 251 of a base or body 116. The access port 10 in FIGS. 57A-57C includes a retaining ring 230, which seals the septum 118 to the base or body 116, over the cavity 36. In one embodiment, the retaining ring 230 is press fit into the base or body 116 to hold the septum 118 in place. FIGS. 58A-58C show yet another embodiment, wherein the access port 10 includes an identification feature 200 on the cavity base 220 and wherein the cavity base is mated to and flush with a lower surface 252 of a cap 114 to define a body. In a particular embodiment, the cavity base 220 is press fit into the cap 114, though other mating configurations can also be employed.

Figure 59A:
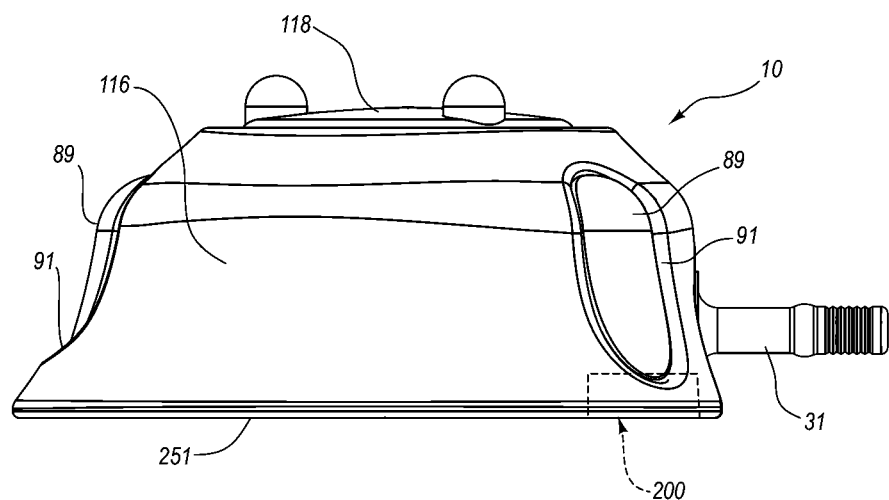
FIG. 59A shows a side view of an embodiment of an access port.
Figure 59B:
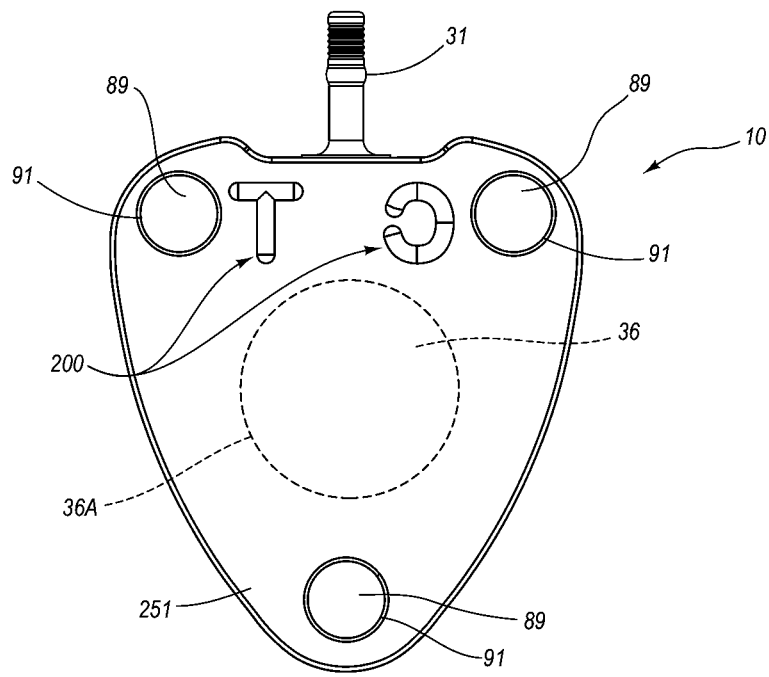
FIG. 59B shows a bottom view of the access port shown in FIG. 59A.

In another embodiment contemplated by the instant disclosure, FIGS. 59A and 59B show that the location of the identification feature 200 can vary as well. Rather than placing the identification feature 200 under the cavity 36, it is possible to place the identification feature under another portion of the access port 10, such as under the outlet stem 31 and between the septum plugs 89, i.e., proximate the outer periphery of the access port bottom surface. Though the overall thickness of the access port structure above the identification feature 200 is greater in this location than if engraved under the cavity 36, the change in location allows for a relatively deeper engraving, which will increase contrast without risk of excessive thinning of the cavity base 220. Additionally, in one embodiment, it is possible to define the identification feature compositely by engraving into both the bottom and top surfaces, such that the engravings are vertically aligned. This enables the remaining material thickness to be substantially reduced in order to provide relatively greater radiographic transmission through the identification feature.

Figure 60A:
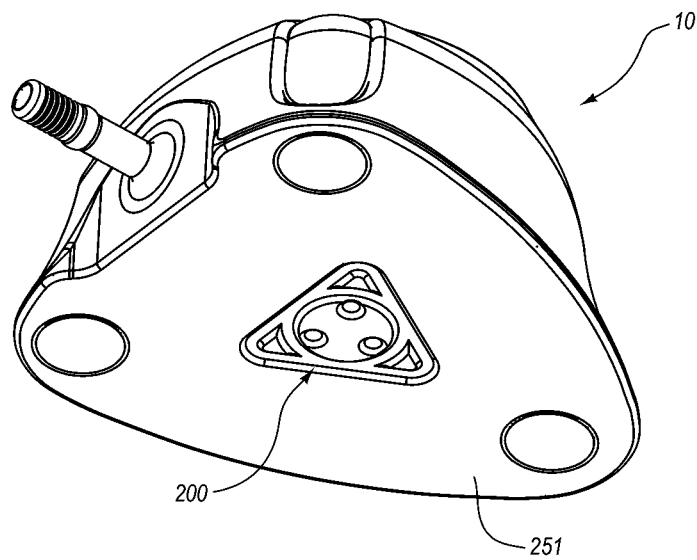
FIG. 60A shows a bottom perspective view of an additional embodiment of an access port.
Figure 60B:
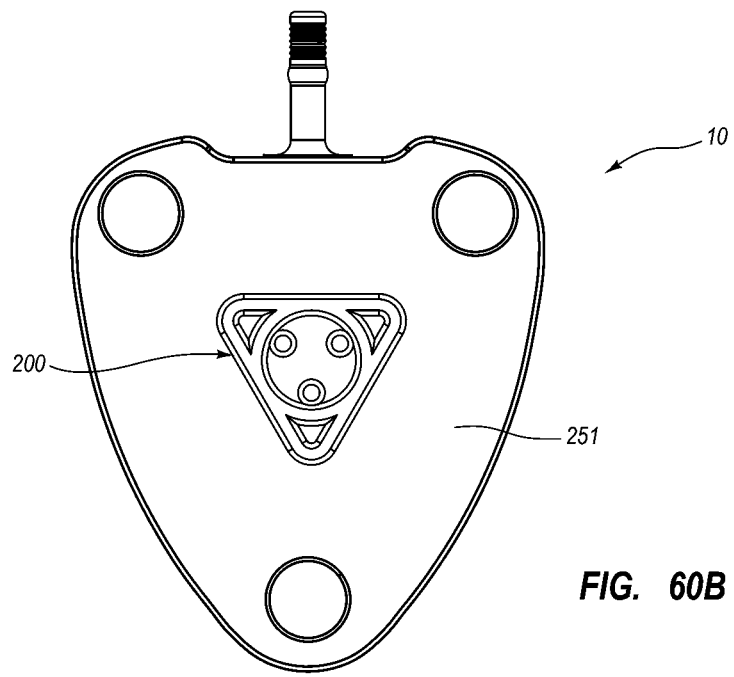
FIG. 60B shows a bottom view of the access port shown in FIG. 60A.
Figure 61A:
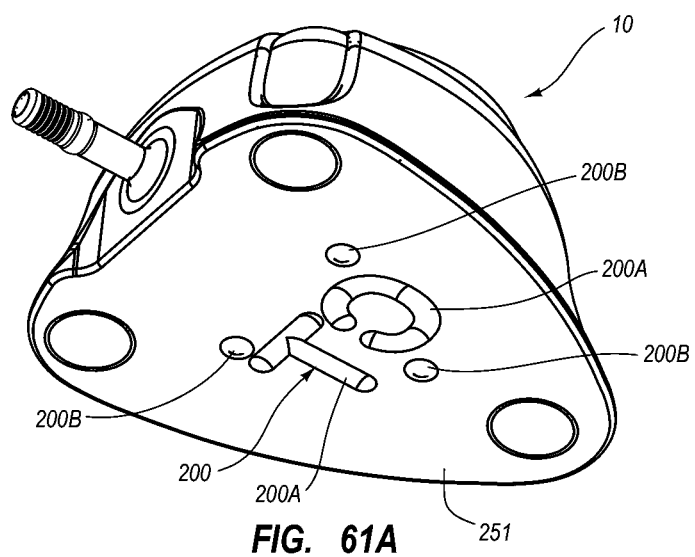
FIG. 61A shows a bottom perspective view of an additional embodiment of an access port.
Figure 61B:
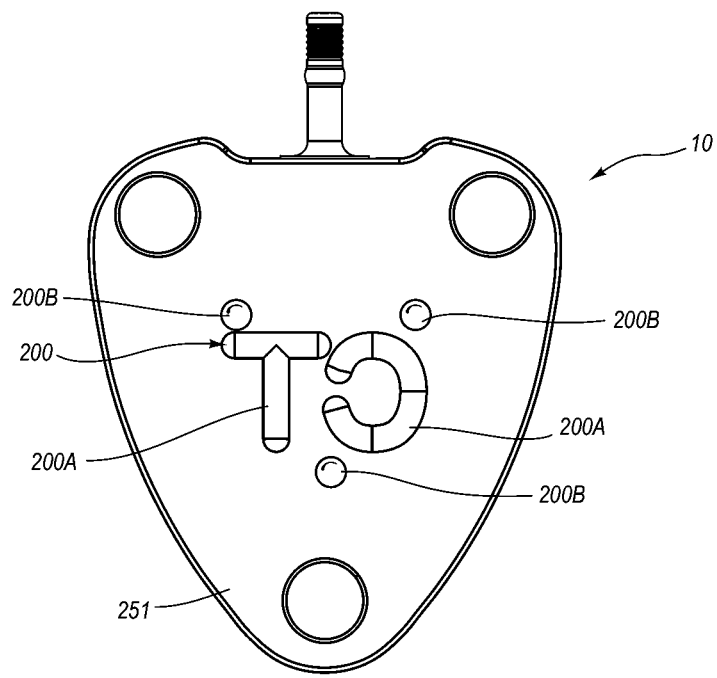
FIG. 61B shows a bottom view of the access port shown in FIG. 61A.
Figure 62A:
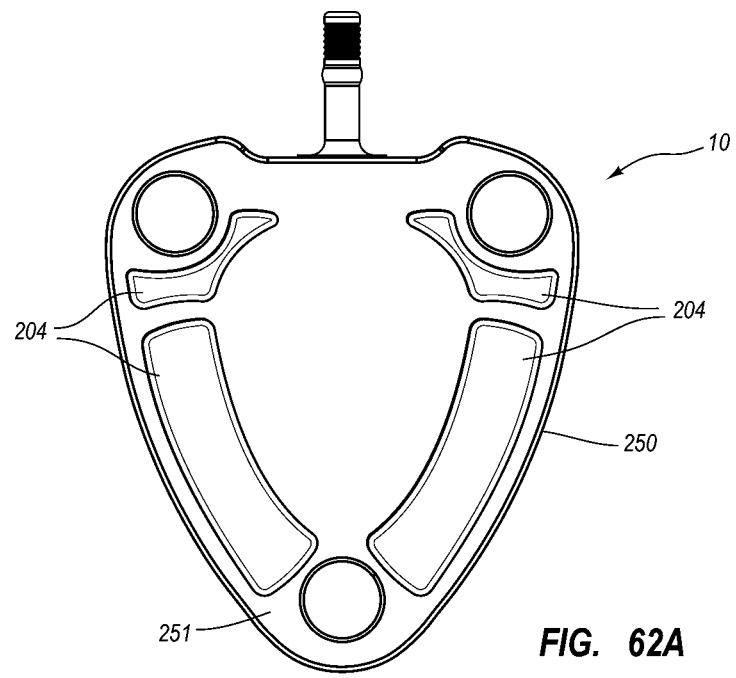
FIG. 62A shows a bottom view of an additional embodiment of an access port.
Figure 62B:
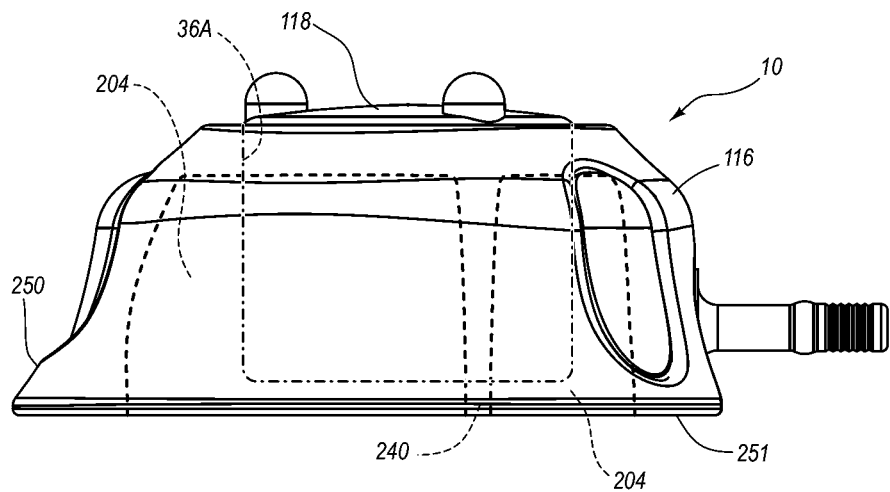
FIG. 62B shows a side view of the access port shown in FIG. 62A.
Figure 62C:
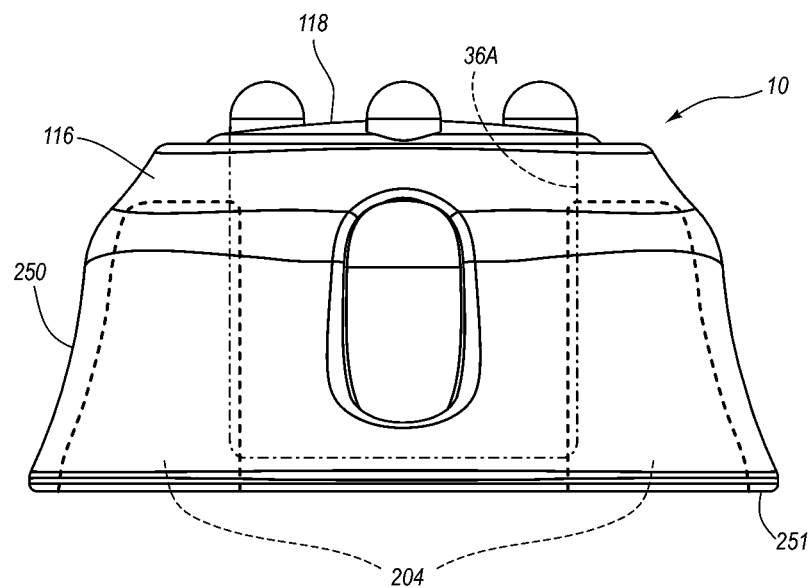
FIG. 62C shows an end view of the access port shown in FIG. 62A.
Figure 63A:
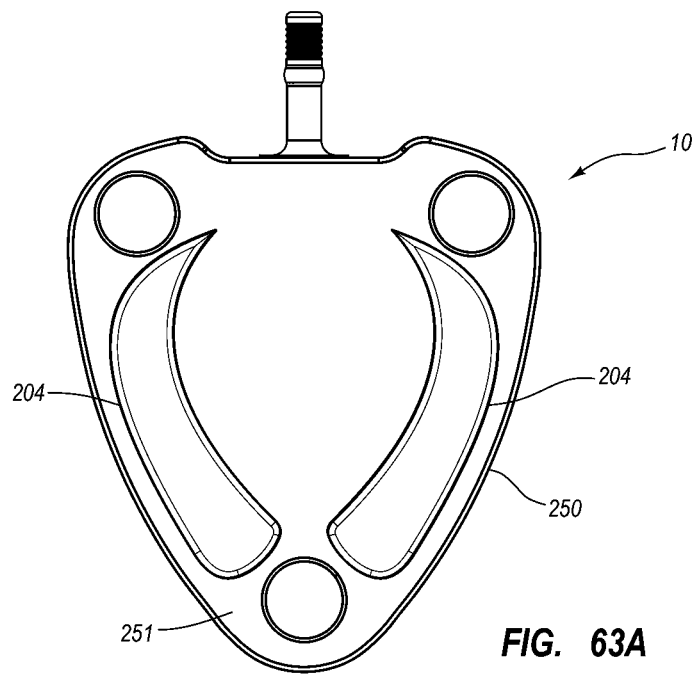
FIG. 63A shows a bottom view of another embodiment of an access port.
Figure 63B:
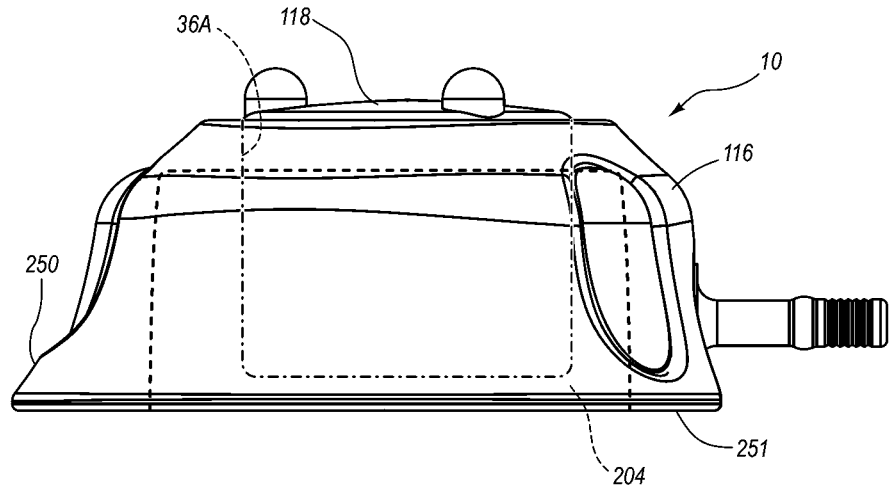
FIG. 63B shows a side view of the access port shown in FIG. 63A.
Figure 63C:
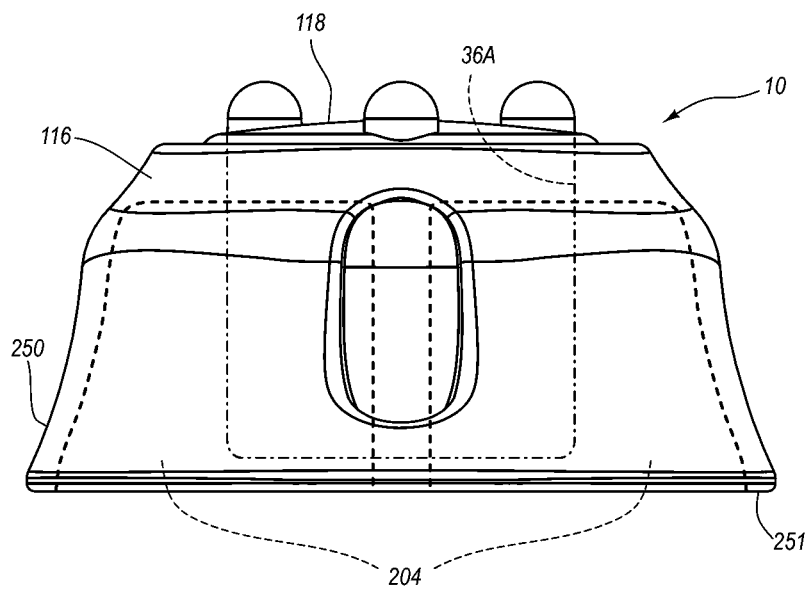
FIG. 63C shows an end view of the access port shown in FIG. 63A.

Additionally, the instant disclosure contemplates access ports having any variety or combination of desired identification features for indicating power-injectability or other aspect or characteristic of an access port. Specifically, FIGS. 60A-61B depict different types of identification features 200, according to example embodiments. FIGS. 60A-60B depict a symbolic identification feature 200. FIGS. 61A-61B depict an exemplary embodiment of an access port 10 including a combination of identification features 200, namely an alphanumeric identification feature 200A and a patterned identification feature 200B. A patterned or symbolic identification feature can also be used to help indicate the orientation of the port or for any other desired reason. It is understood by the instant disclosure that other symbols, patterns, marks, and alphanumeric characters can be used both alone and in any combination with each other on a variety of access port configurations.

In additional embodiments, the identification feature can be defined on an inside bottom surface 36B of the cavity 36 of an access port 10, or in addition to the identification feature 200 provided on the bottom surface 251. In another embodiment, the material surrounding the defining edges of the desired radiopaque alphanumeric character, symbol, pattern, etc., can be removed instead of removing the desired feature shape itself so as to define a "positive" relief image of the identification feature. Such a positive relief identification feature can be defined on a lower surface of an access port body or on the inside bottom surface of the cavity, for example.

In addition to the various types of symbols, patterns, marks, and alphanumeric characters that are contemplated by the instant disclosure, FIGS. 62A-63C disclose additional example embodiments of identifying features on access ports that are observable via x-ray or other suitable imaging technology. Specifically, the instant disclosure contemplates the use of shelled-out cavities 204, wherein portions of the access port 10 are hollowed out. This results in shelled-out cavities 204 extending inward from the lower surface 251 of the base or body 116 or corresponding port lower surfaces of the other embodiments described herein, including the lower surface 151 of the base 16, as in FIG. 151, and the lower surface 252 of a cap 114, as in FIGS. 58A-58C. This is done by removing the material surrounding the cavity 36 without disrupting the cavity periphery 36A or the outer side surfaces 250 of the access port 10. As seen in FIG. 62B, ribs 240 may be left to support the remaining "shelled" frame of the access port 10. The definition of such cavities 204 provides a relative difference in radiopacity of the access port 10 that can be identified via x-ray imaging. As such, the cavities 204 can be arranged to define a pattern or to form an indicia for identification of an aspect or characteristic of the access port 10. Note that in other embodiments, the cavities can be defined so as to extend from other surfaces of the access port, including the top and sides thereof.

In a further aspect contemplated by the instant disclosure, it is contemplated that a communicative technology may be utilized wherein information is encompassed by an access port contemplated by the instant disclosure. Generally, a communication device (e.g., a radio beacon, a light-emitting element, an ultrasound emitting transducer, etc.), may be imbedded or otherwise affixed to an access port contemplated by the instant disclosure. Such a communication device may be configured for transmitting information in response to a given impetus. More specifically, the instant disclosure contemplates that an access port contemplated by the instant disclosure may be exposed to a request signal (e.g., a sound, an impact or an acceleration, light, radio waves, etc.). Such a request signal may cause the communication device to transmit information therefrom via sound, light, radio waves, or as otherwise known in the art. Such information may be employed for identifying an access port contemplated by the instant disclosure.

In one exemplary example, it is contemplated that radio frequency identification technology may be employed for identification of an access port contemplated by the instant disclosure. Particularly, so-called active RFID tags are powered by an internal battery and are typically read/write devices. Currently, a suitable cell coupled to suitable low power circuitry can ensure functionality for as long as ten or more years, depending upon the operating temperatures and read/write cycles and usage. So-called passive RFID tags operate without a separate external power source and obtain operating power generated from the reader. Passive RFID tags are typically programmed with a unique set of data (usually 32 to 128 bits) that cannot be modified. Read-only tags may operate as an identifier comparable to linear barcodes which may contain selected product-specific information. Thus, passive RFID tags may be much lighter than active RFID tags, less expensive, and may offer a virtually unlimited operational lifetime. The tradeoff is that they have shorter read ranges than active tags and require a higher-powered reader.

One advantage of RFID approach is the noncontact, non-line-of-sight nature of the technology. Tags can be read through a variety of substances such as snow, fog, ice, paint, crusted grime, and other visually and environmentally challenging conditions, where other optically read technologies may be less effective. RFID tags can also be read in challenging circumstances at rapid speeds, in most cases responding in less than about 100 milliseconds.

Reference is now generally made to FIGS. 64-75C in describing additional embodiments wherein an access port includes at least one identification feature observable through interaction with an imaging technology, such as x-ray and fluoroscopy, for instance, in order to facilitate identification of at least one attribute, or characteristic, of an access port subsequent to implantation within the body of a patient. It is appreciated that the embodiments to be described can be included alone or together with other identification features described herein and may be employed with access ports having a variety of sizes, shapes, and other variations in configuration. As such, the embodiments described herein are merely examples of the principles of the present disclosure.

Figure 64:
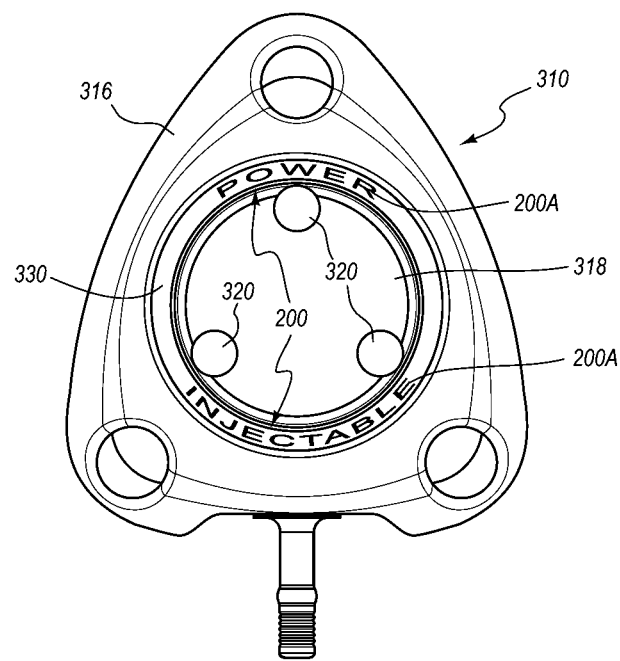
FIG. 64 shows a top view of an access port according to one embodiment.

FIG. 64 shows an access port 310 including a base 316 and a septum 318 covering a reservoir defined by the base. The septum 318 includes a plurality of palpation bumps 320 for enabling external digital palpation and location of the septum by a clinician after the access port 310 has been subcutaneously implanted. The port 310 includes a retaining ring 330 for capturing and retaining the septum 318 in place atop the port reservoir. In the present embodiment, both the port base 316 and the retaining ring are metallic substance, including titanium for instance, though in other embodiments other suitable materials may be used.

In the present embodiment the retaining ring 330 includes an identification feature 200 for identifying a predetermined attribute or characteristic of the port 310 after implantation thereof. Specifically, the retaining ring 330 includes alphanumeric character identification features 200A spelling "POWER INJECTABLE," which indicates that the port 310 is capable of power injection. The alphanumeric characters in one embodiment are inset via etching or otherwise suitably defined in the retaining ring 330 so as to provide a relative thickness difference between the characters and surrounding metallic retaining ring material, thus providing a corresponding radiographic contrast when the port 310 is imaged with x-ray imaging technology. This contrast enables the alphanumeric characters to become visible in an x-ray and therefore discernible by a clinician viewing the x-ray, thus enabling the port attribute or characteristic relating to the identification feature 200 to be ascertained.

Note that the alphanumeric identification features 200A can be defined on the retaining ring 330 in any number of suitable ways, including etching, engraving, etc., and the characters can be defined partially or completely through the retaining ring. Also, the particular characters or words used can vary from what is described here. Indeed, other characters, patterns, symbols, etc. can be employed in the identification feature 200. Optionally, the identification features can be defined in negative relief, as shown in FIG. 64, or in positive relief, if desired.

Additionally, in other embodiments the identification feature of the retaining ring can be configured in other ways according to the configuration of the port. For instance, in embodiments where the port body includes a non-metallic material, the identification feature can include radiopaque ink that is applied to a surface of the retaining ring so as to form the alphanumeric or other characters or features. In yet other embodiments, the identification feature can be included on portions or surfaces of the port in addition to the retaining ring. These and other modifications are therefore contemplated.

Figure 65:
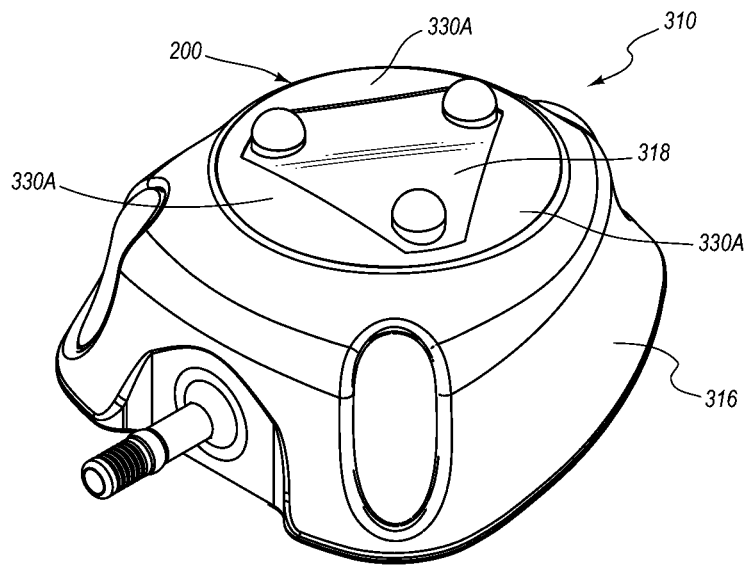
FIG. 65 shows a perspective view of an access port according to one embodiment.

FIG. 65 includes the metallic retaining ring 330 of the metallic port 310 configured in accordance with another embodiment, wherein the retaining ring defines the identification feature 200, including a plurality of overlapping portions 330A that each overlap a portion of the septum 318 retained by the retaining ring. In FIG. 65, the overlapping portions 330A of the retaining ring 330 cooperate to generally define a triangular shape, which provides a radiographic contrast relative to portions of the metallic port 310 below the retaining ring. As before, this provides a corresponding radiographic contrast when the port 310 is imaged with x-ray imaging technology, enabling the triangular shape to be discernible as a radiopaque outline by a clinician viewing the x-ray in order to ascertain the predetermined port attribute or characteristic relating to the identification feature 200 to be ascertained. In other embodiments, the retaining ring can define other shapes in addition to the triangular shape shown here. Additionally, characters, symbols, or other patterns can be defined in or included on the overlapping portions of the retaining ring if desired.

Figure 66A:
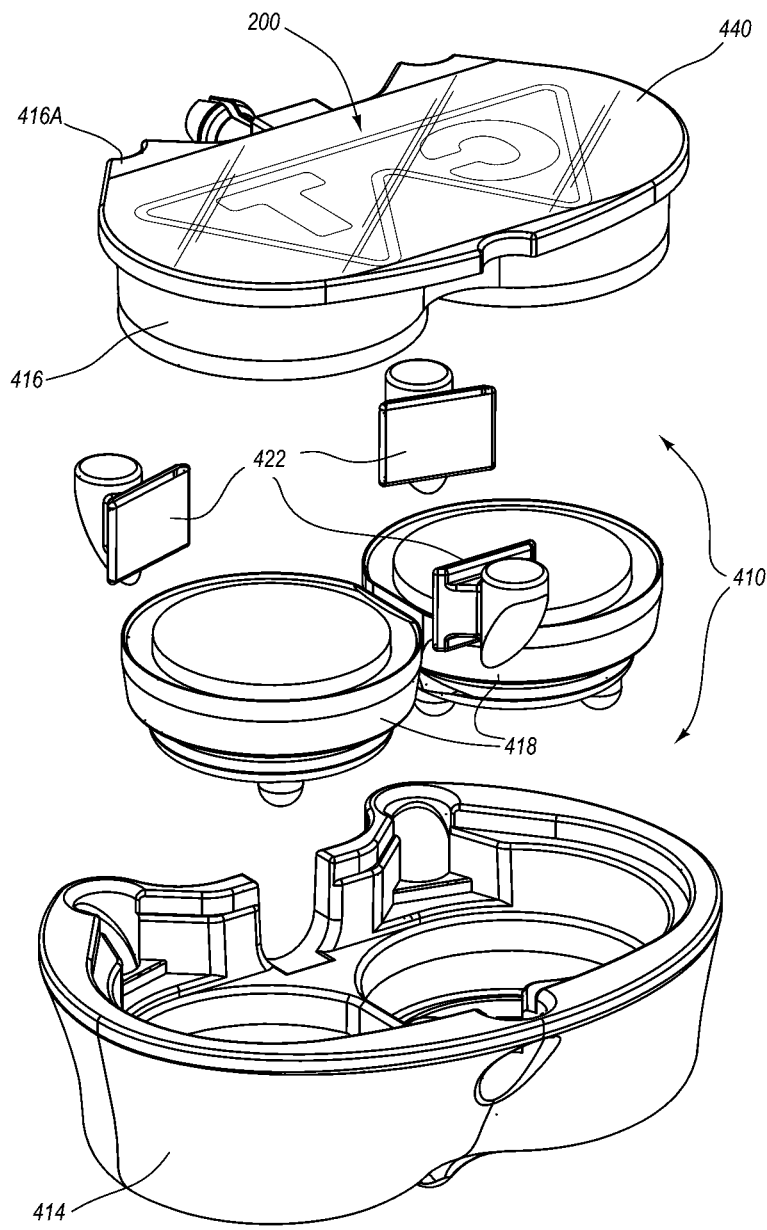
FIGS. 66A-66D show various views of an access port according to one embodiment.
Figure 66B:
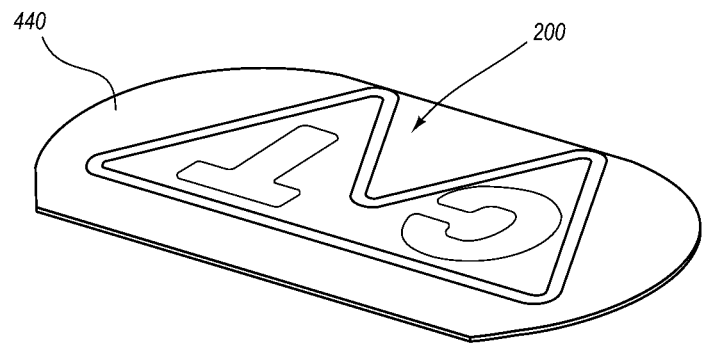

FIGS. 66A-66D depict various details regarding the inclusion of an identification feature for identifying a predetermined attribute or characteristic of an access port after implantation into a patient. Specifically, these figures depict a dual reservoir access port 410, including a cap 414 matable to a base 416 and two septa 418 interposed between the cap and base. Suture plugs 422 are included with the port 410. In accordance with the present embodiment, a bottom surface 416A of the port base 416 includes the identification feature 200 for identification of the subcutaneously implanted port. As best seen in FIG. 66B, the identification feature 200 in the present embodiment includes a radiopaque marking including the letters "C" and "T" outlined by a double-triangle border, though many different character, pattern, and/or combination configurations are possible. For instance, in addition to identifying the access port as power injectable, this and other identification features described herein can be used to designate lot numbers, hospital identification, port brand, etc.

The radiopaque marking of the identification feature 200 can include a metallic powder intermixed with an ink-based marking. Specifically, in one embodiment, the radiopaque marking includes tungsten powder intermixed with 1020 black wire marking ink manufactured by Gem Gravure, Inc. of West Hanover, Mass., in a ratio of three parts tungsten powder to one part ink. Mixing of the two components can include ball mixing to ensure good component integration in one embodiment. Also, additives can be added to the mixture to attain a proper mixture viscosity.

In other embodiments, the powder-to-ink ratio can be modified from that described above, including 2:1, 4:1, and 5:1 ratios, for instance. The ideal ratio will vary according to the type of materials employed in the mixture, the density of the desired image, powder particle size, amount of mixture applied to the port, etc. In yet other embodiments, other medical grade inks or suitable liquids, as well as other biocompatible metallic powders or suitable radiopaque materials, could be used. In one embodiment, a ceramic, such as zirconium oxide powder, can be intermixed with a marking ink to provide the radiopaque marking. Ink thinners can also be added to the mixture, along with other suitable substances as appreciated by those skilled in the art.

As shown in FIG. 66B, the ink-based radiopaque marking that forms the identification feature 200 in the present embodiment is included on a substrate 440. In one embodiment, the substrate 440 includes a material substantially identical to the material included in the port 410. Specifically, in one embodiment, both the port 410 and the substrate 440 include an acetyl resin sold under the brand DELRIN®, though it is appreciated that other suitable materials could be used for the substrate and port.

The substrate 440 is employed as a base on which the radiopaque marking can be deposited in preparation for integration of the substrate and marking into the port 410 during an injection molding process so as to encapsulate the radiopaque marking within the molded port. In detail, in one embodiment, the radiopaque marking, including the above-described ink/powder mixture or other suitable substance, is first deposited on a surface of the substrate 440 via any acceptable process, including pad printing, manual or automatic painting, silk screening, use of a template, etc. To improve adhesion of the ink/powder mixture, the substrate can be plasma treated or corona treated in one embodiment.

Figure 66C:
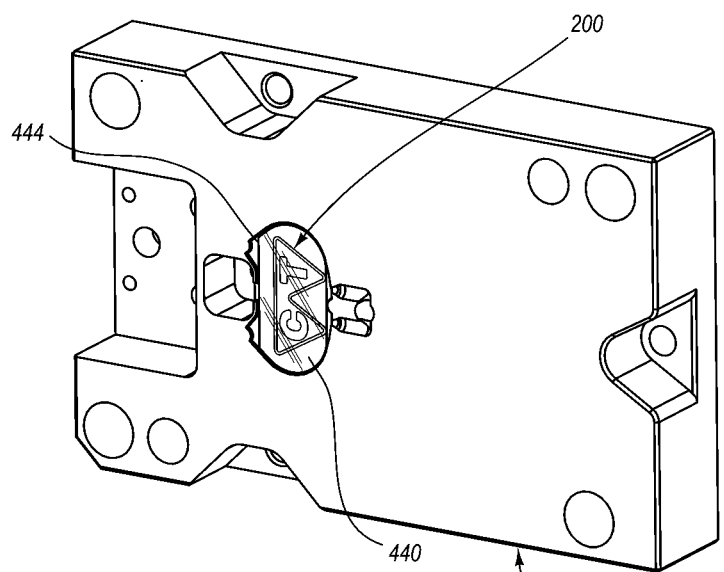

Once the radiopaque marking has been applied to the substrate 440, the substrate is loaded into a mold, such as that shown in FIG. 66C, which depicts the substrate positioned within a cavity 444 of a portion of a mold 442. The substrate 440 is positioned within the mold cavity 446 such that the radiopaque marking is facing in toward what will become the center of the port 410. In one embodiment, the substrate 440 is held in place within the mold cavity 444 via a vacuum assist system; in other embodiments, temporary mechanical fixation can be employed, if necessary. A template including a hole sized to enable the substrate to pass therethrough can be used in one embodiment to assist the technician in placing the substrate 440 with the proper orientation within the mold cavity 444.

Figure 66D:
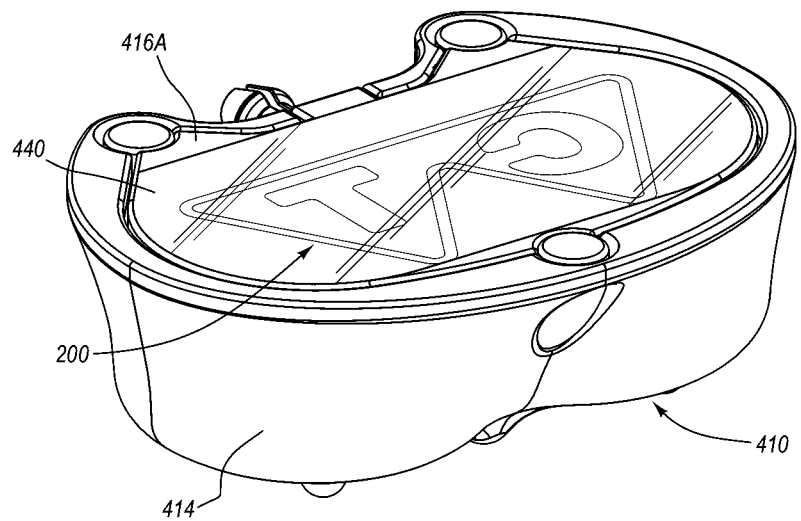

The port 410 is then fabricated by an injection molding process. The substrate 440 is thus insert-molded into the port 410 via the injection molding process, which bonds the substrate 440 to the molded body of the port 410, thus encapsulating the radiopaque marking of the identification feature 200 within the port and preventing its inadvertent removal. Additionally, due to the relative thinness of the substrate 440, the identification feature remains visible through the substrate from outside of the port 410, as seen in FIG. 66D, before implantation. In one embodiment, the thickness of the substrate 440 ranges from about 0.002 inch to about 0.015 inch, though other thicknesses can be acceptably used. Later, when the port 410 is implanted and imaged under x-ray, the identification feature 200 will be visible in the x-ray image and useful to identify an attribute or characteristic of the implanted port.

It is appreciated that in other embodiments, the substrate can be configured to be positioned in other regions of the port.

In yet other embodiments, other substrate materials can be used. For instance, in one embodiment the substrate can include woven high-density polyethylene sold under the brand TYVEK®. In this case, the substrate 440 does not permanently adhere to the port 410 as a result of the insert molding process, but is removed after molding process is complete. The radiopaque marking ink/powder mixture initially included on the woven substrate 440, however, is integrated into the port body and remains with the port 410 after molding and substrate removal to serve as the identification feature 200. Flaps or flanges can be included on the substrate to facilitate its separation from the substrate from the port after molding, in one embodiment. In another embodiment, the ink/powder radiopaque marker mixture is allowed to dry on the substrate 440 after application thereon to improve adhesion to the port 410 during the insert molding process. In addition to those explicitly described here, other suitable materials can be used as the substrate. In yet another embodiment, no substrate is used and the ink/powder radiopaque marker mixture is applied directly to the mold surface before the port 410 is molded therein.

Figure 74A:
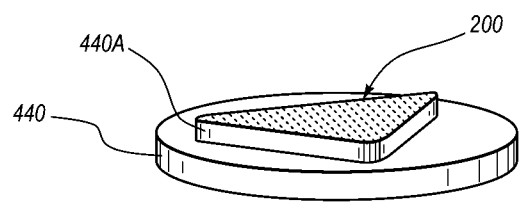
FIGS. 74A and 74B show views of an identifier for an access port according to one embodiment.
Figure 74B:
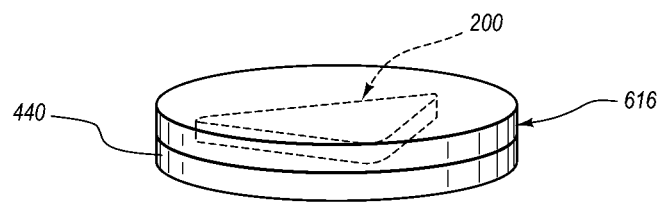

FIGS. 74A and 74B depict details of the substrate 440 and identification feature 200 configured in accordance with another embodiment, wherein the substrate forms a portion of the port base. A raised surface 440A is included on the substrate, and a radiopaque marking, such as the intermixed marking ink and radiopaque powder, is included on the raised surface to define the identification feature 200. Application of the radiopaque marking can occur in any one of a number of suitable ways, including contact application by a stamp or tamp pad, ink jet printing, physical or chemical deposition, etc.

The substrate 440 with the included identification feature 200 can then be inserted into a mold and insert-molded to form part of a base 616 of an access port. The radiopaque identification feature 200, now encapsulated within the base, provides the desired identification of a predetermined attribute or characteristic of the port once manufacture of the port is complete.

Figure 67:
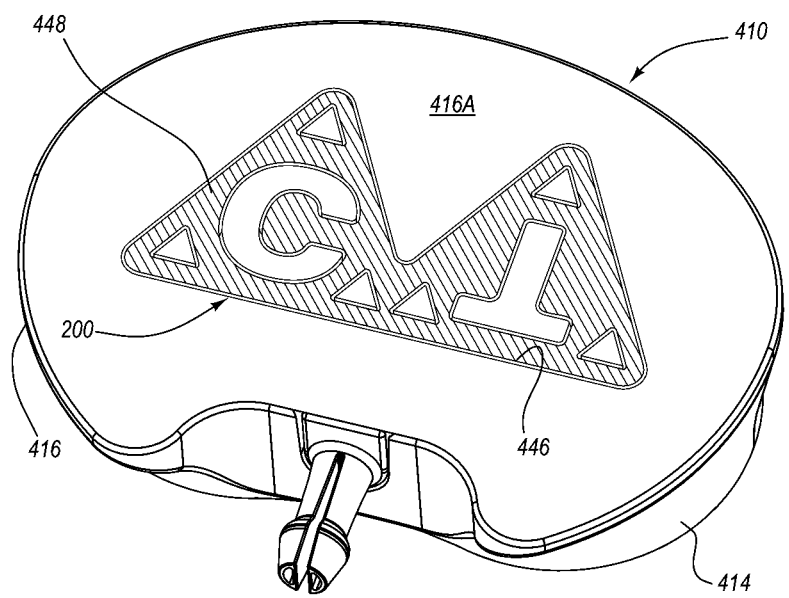
FIG. 67 shows a bottom perspective view of an access port according to one embodiment.

Reference is now made to FIG. 67, which depicts another identification feature for an access port, such as a plastic port for instance, according to one embodiment. In particular, the port 410 of FIG. 67 includes a cavity 446 defined on a bottom surface 416A of the port base 416. In one embodiment, the cavity 446 is defined to a depth of about 0.010 inch, though other depths can also be used according to desire and port configuration. The cavity 446 is filled with a radiopaque fill material 448. The cavity 446 is shaped with a predetermined design or configuration so as to form the identification feature 200 when filled with the radiopaque fill material 448, thus enabling a predetermined attribute or characteristic of the port 410 to be identified via x-ray imaging subsequent to implantation. In the present embodiment, the fill material 448 includes tungsten powder intermixed with a two-part silicone sold under the brand SILASTIC® Q7-4840, available from Dow Corning Corporation, Midland, Mich. in equal quantities, i.e., equal parts of part A silicone, part B silicone, and tungsten powder. Of course, other suitable materials could also be employed. For instance, titanium can be used in place of tungsten, and biocompatible urethane adhesives can be used in place of silicone.

In one embodiment, the fill material 448 is injected into the cavity 446 by a pressurized syringe, such as an electronic fluid dispenser, though other suitable techniques can also be employed, including manual filling by syringe. Any excess fill material 448 can be removed from the port base bottom surface 416A after filling, and the fill material can be allowed to cure. Note that in other embodiments the bottom surface of the port can include other portions of the port in addition or instead of the base, as shown in FIG. 67.

Figure 68A:
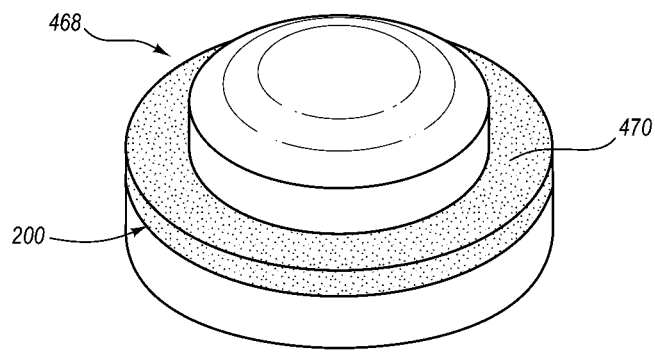
FIGS. 68A-68C show various views of a septum of an access port according to one embodiment.
Figure 68B:
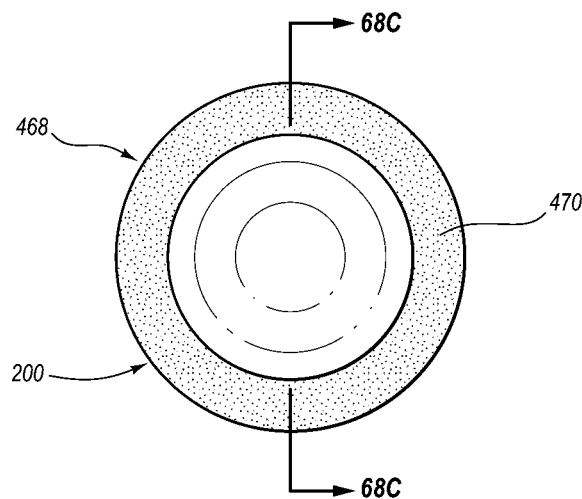
Figure 68C:

FIGS. 68A-68C show details of one embodiment for providing the identification feature 200 on a resilient septum 468 of an implantable access port, such as a plastic port for instance, wherein the septum includes a radiopaque portion visible under x-ray imaging to provide information relating to an attribute or characteristic of the septum itself and/or the access port in which the septum is disposed. In the illustrated embodiment, the radiopaque portion is defined as an annular portion 470 disposed about the upper outer periphery of the septum 468 so as not to interfere with puncturing of the septum by needles during port use. As best seen in FIG. 68C, the annular portion does not extend in depth through the thickness of the septum outer portion, but in other embodiments the thickness, size, and position of the radiopaque portion can vary on the septum.

In the present embodiment, the radiopaque annular portion 470 includes barium sulfate-loaded silicone, while the remainder of the septum 468 is unloaded silicone. In other embodiments, other suitable radiopaque materials can be employed with silicone or other septum materials. In one embodiment, the septum 468 of FIGS. 68A-68C can be formed by a two-part molding process, wherein the annular portion 470 is manufactured separately from the rest of the septum 468, then the two parts are adhered together by a suitable adhesive, mechanical fixation, etc., to form the structure shown in FIGS. 68A-68C.

In another embodiment, the present septum 468 is manufactured integrally via a co-molding process, wherein separate injection heads are employed in a mold cavity in order to injection mold the annular portion 470 with one or more heads and the rest of the septum 468 with separate heads. These and other manufacturing methods are therefore considered within the spirit of the present disclosure.

Figure 69:
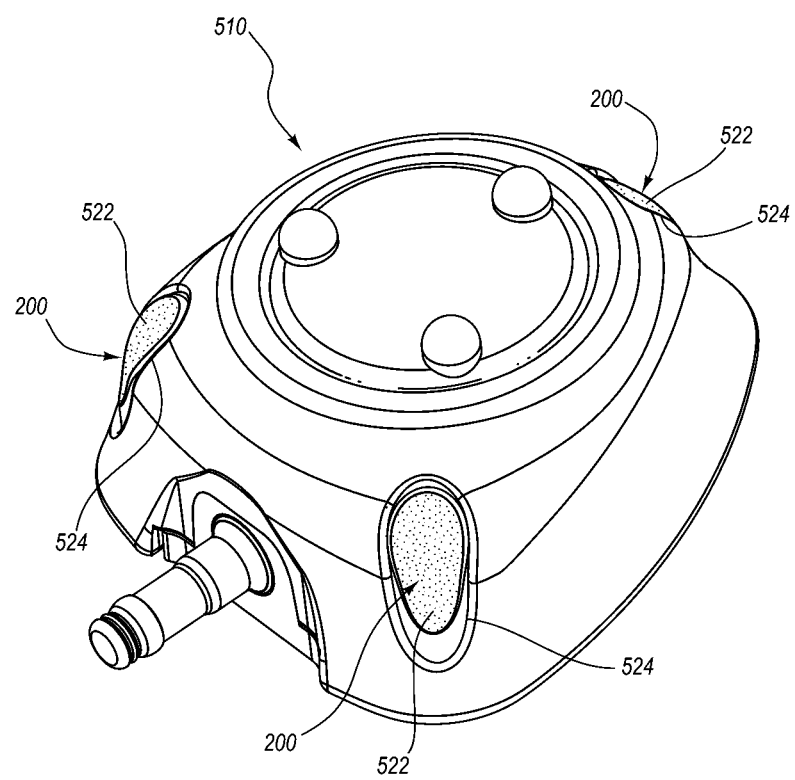
FIG. 69 shows a perspective view of an access port according to one embodiment.

The principles discussed in connection with FIGS. 68A-68C can be expanded in one embodiment shown in FIG. 69, wherein a port 510 including resilient suture plugs 522 disposed in corresponding suture plug holes 524 is configured such that the suture plugs include a radiopaque material, such as the barium sulfate-loaded silicone employed in the septum 468 of FIGS. 68A-68C or other suitable radiopaque material. So configured, the suture plugs provide the identification feature 200 that is visible under x-ray imaging to provide information relating to an attribute or characteristic of the port 510. In one embodiment, the port 510 can include both the radiopaque suture plugs 522 and the septum 468 including the radiopaque portion 470 in order to provide additional identification ability and/or to provide information relating to the orientation of the port within the body of the patient. In addition to barium sulfate, the suture plugs can include tungsten, tantalum, or other suitable radiopaque materials. In yet another embodiment, one or more radiopaque beads can be disposed in the port body to provide similar port visibility under x-ray.

In one embodiment, the septum, suture plugs, or other portion of the port can include an ultraviolet light-sensitive material. The ultraviolet light-sensitive material can be applied to the surface of the port component or can impregnated into the component. After implantation of the port, ultraviolet light is directed through the skin of the patient to be incident on the ultraviolet light-sensitive material of the port, which causes the material to fluoresce with visible light that is observable through the skin of the patient, thus identifying the port and/or its predetermined attribute or characteristic.

Figure 70:
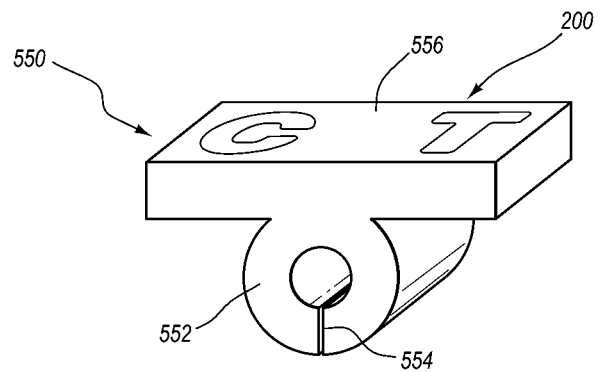
FIG. 70 shows a perspective view of an identifier for an access port according to one embodiment.

It is appreciated that a radiopaque identification feature can be included or associated with a port in other ways in addition to those embodiments already described. Examples of this can be found in the embodiments depicted in FIGS. 70-72. In FIG. 70, for example, an identifier tag 550 is shown, including a ring portion 552 with a slit 554 for enabling the identifier ring to be attached to a catheter that is operably attached to the stem of a port. The identifier tag 550 further includes a face portion 556 on which a radiopaque identification feature 200 can be placed for visibility via x-ray imaging to identify a predetermined attribute or characteristic of the port. The tag can be designed in various different shapes and configurations. For instance, the tag can be included as part of a catheter securement device for locking an end of a catheter to the stem of the port.

Figure 71:
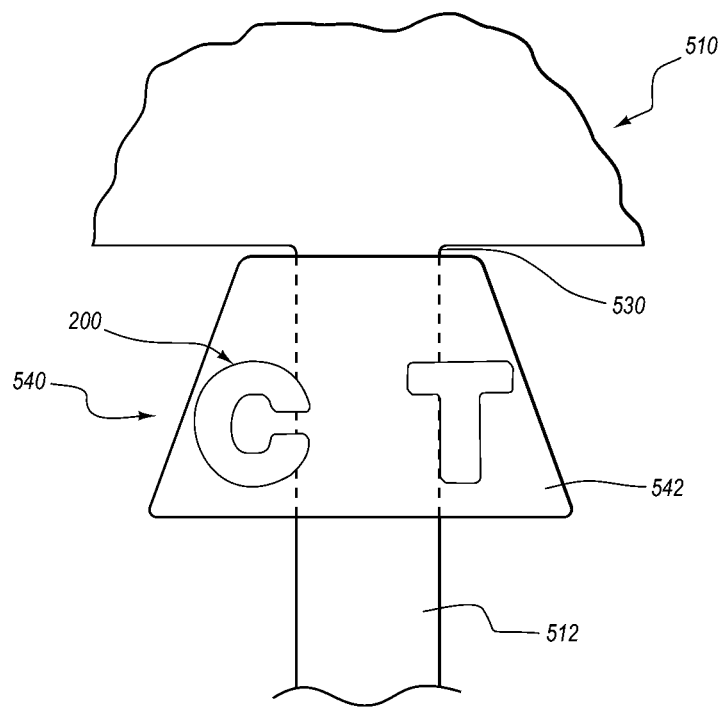
FIG. 71 shows a top view of an identifier for an access port according to one embodiment.

In FIG. 71, the port 510 is shown with a catheter securement device 540 that is used to secure the connection between an end of a catheter 512 and a stem 530 of the port. A body 542 of the catheter securement device 540 is configured to include the identification feature 200 for visibility via x-ray imaging to identify a predetermined attribute or characteristic of the port to which the device is attached. Again, the shape, size, and particular configuration of the catheter securement device and identification feature can vary from what is shown and described herein.

Figure 72:
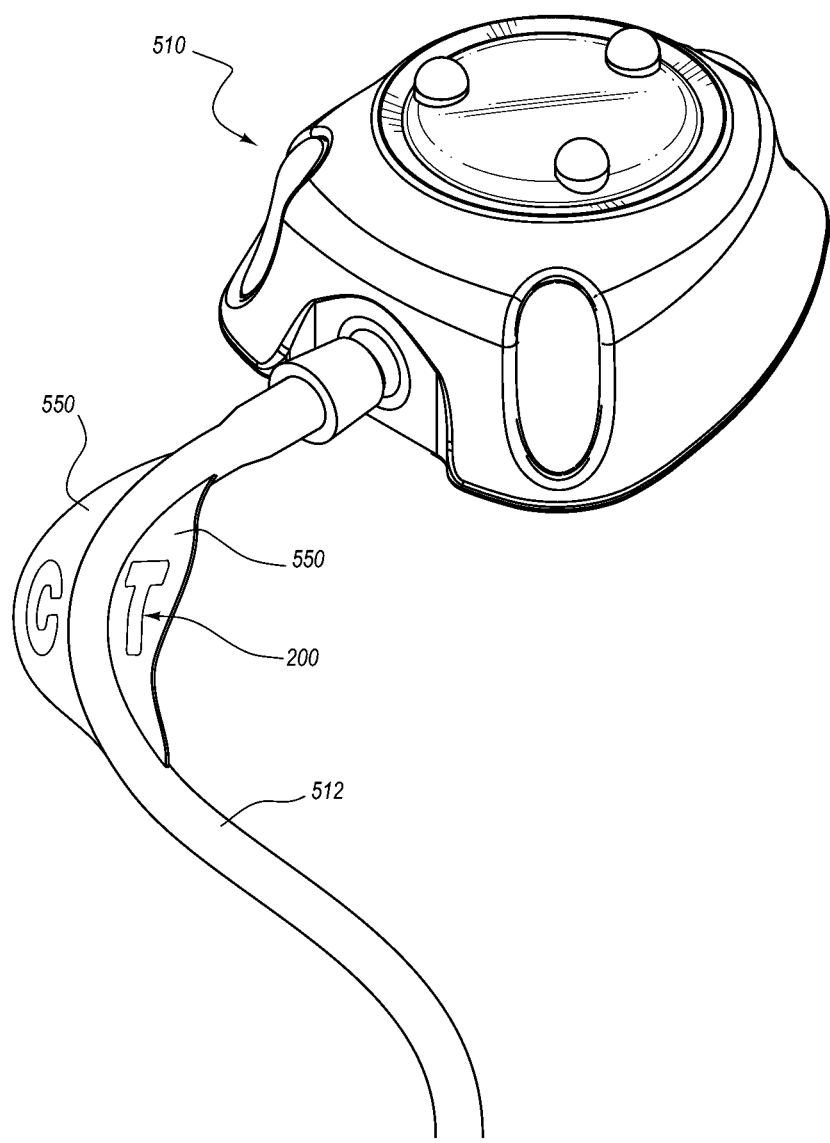
FIG. 72 shows a perspective view of a port and a catheter including an identifier according to one embodiment.

In FIG. 72, the port 510 is shown with the catheter 512 operably attached thereto. The catheter 512 includes two flaps 550 that extend from the body thereof, on which the identification feature 200 is included in order to provide a visible identification of a predetermined attribute or characteristic of the catheter and/or port when imaged under x-ray. Of course, the particular identification feature, as well as the number and size/configuration of the catheter flaps can vary from what is described herein.

Figure 73A:
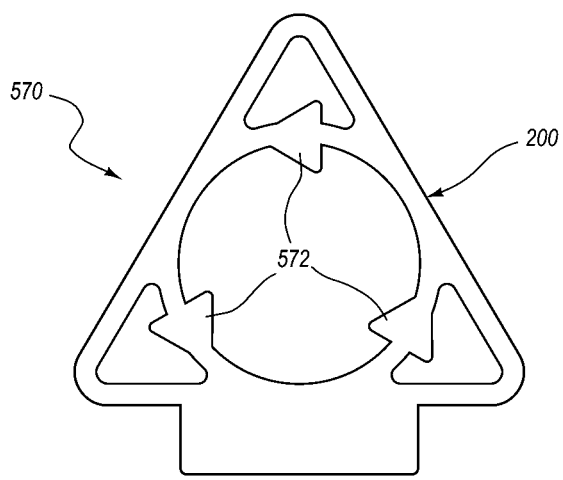
FIGS. 73A and 73B show various views of an identifier for an access port according to one embodiment.
Figure 73B:
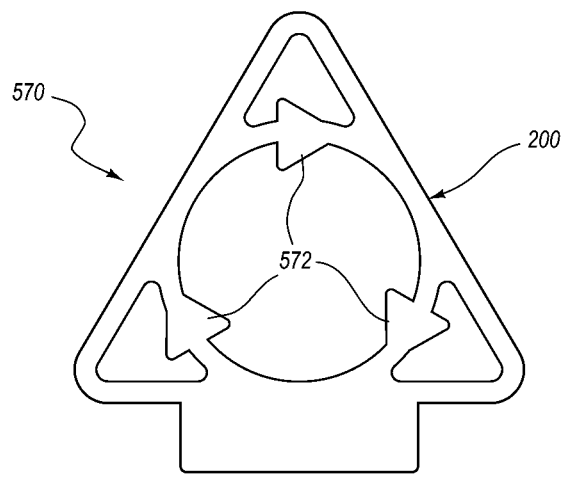

FIGS. 73A and 73B depict yet another example of a radiopaque identification feature wherein the identification feature 200 is included in an insert 570 formed from a radiopaque material, such as tungsten or other suitable material. The insert 570 is suitable for placement in a plastic or other radiotranslucent port such that the insert is visible under x-ray imaging to identify an attribute or characteristic of the port. Orientation arrows 572 provide useful indicia of the orientation of the port. By examining the direction of the arrows 572, a clinician observing an x-ray image of the port insert 570 can determine whether the port is flipped in the body of the patient. In addition to these, other indicia indicating port orientation can be included on the insert in other embodiments.

Figure 75A:
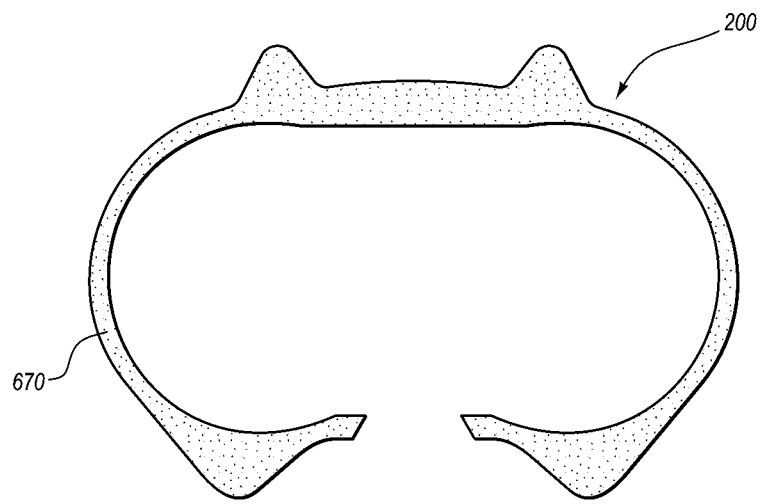
Figure 75C:
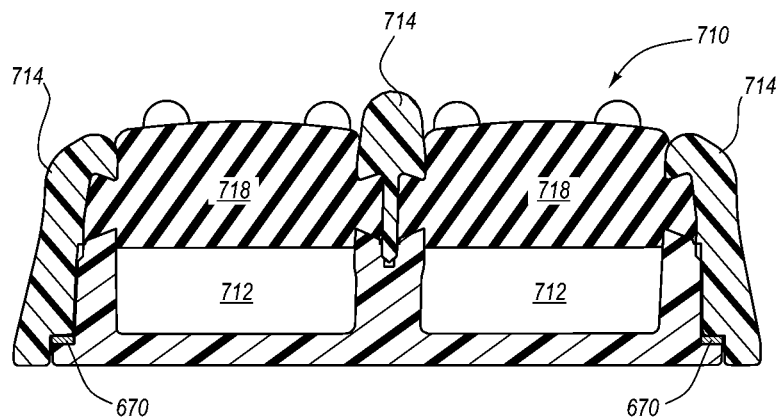

FIGS. 75A-75C show implementation of another example of a radiopaque insert, in addition to that shown in FIGS. 73A and 73B, which is included to serve as the identification feature 200 for identifying a predetermined attribute or characteristic of a port, including a plastic port, as in the present embodiment. In particular, a radiopaque insert 670 is shown, configured to be interposed between a cap 714 and a base 716 of a port 710. Note that, though the insert 670 shown here is configured to fit over a dual fluid cavity 712 of the port 710, other inserts including a variety of radiopaque compositions can be configured to be included in other ways with a port. Additionally, the port can define one, two, or more fluid cavities covered by septa 718, without limitation.

As shown in FIG. 75B, the insert 670 fits over the fluid cavities 712 of the port 710 so as to rest on a portion of the port base 716. So positioned, the insert 670 is sandwiched and secured between the base 716 and the cap 714 when the base and cap are mated together to form the port 710. Such mating can be accomplished by ultrasonic welding, adhesives, etc.

The resulting interposition of the insert 670 between the base 716 and cap 714 is shown in FIG. 75C. When the port 710 is later imaged via x-ray after patient implantation, the insert 670 is readily visible, thus enabling the predetermined attribute/characteristic(s) of the port to be identified.

While certain representative embodiments and details have been shown for purposes of illustrating aspects contemplated by the instant disclosure, it will be apparent to those skilled in the art that various changes in the methods and apparatus disclosed herein may be made without departing form the scope contemplated by the instant disclosure, which is defined in the appended claims. For example, other access port sizes and shapes may be employed; and various other embodiments and structures may be employed for forming at least one identifiable feature of an access port contemplated by the instant disclosure. In particular, FIGS. 25-51 illustrate a number of additional exemplary embodiments of access port 10. As is apparent from these figures, access port 10 may be formed in any number of shapes and sizes, such that any number of modifications and changes are possible to any of the embodiments described and illustrated herein without departing from the spirit and scope of the instant disclosure.

What is claimed is:

1. An access port for providing subcutaneous access to a patient, comprising:
   a port base defining a fluid cavity, the port base formed from a base material;
   a substrate separate from the port base formed from a substrate material, the substrate attached to the port base, the substrate including an inner surface facing toward the fluid cavity and an outer surface facing away from the fluid cavity; and
   a radiopaque material adhered to the substrate inner surface prior to attachment of the substrate to the port base, the radiopaque material including an identification feature.

2. The access port as defined in claim 1, wherein the substrate material includes an acetyl resin or a high-density polyethylene.

3. The access port as defined in claim 1, wherein the substrate material and the base material are substantially similar.

4. The access port as defined in claim 1, wherein the identification feature is visible through the substrate after attachment of the substrate to the port base.

5. The access port as defined in claim 1, wherein the substrate is insert molded with the port base, and wherein the radiopaque material includes a metallic powder intermixed with an ink.

6. The access port as defined in claim 5, wherein the metallic powder is tungsten powder and wherein the tungsten powder is intermixed with the ink at a ratio of three parts tungsten powder to one part ink.

7. The access port as defined in claim 1, wherein the identification feature includes the letters "C" and "T".

8. The access port as defined in claim 7, wherein the letters are outlined by a double-triangle border.

9. The access port as defined in claim 1, wherein the identification feature identifies the access port as power injectable.

10. The access port as defined in claim 9, wherein the identification feature further identifies one or more of: the access port lot number, a hospital identification, and the access port brand.

11. The access port as defined in claim 1, wherein the substrate material comprises a woven material, and wherein the port base is insert molded over the substrate.

12. The access port as defined in claim 11, wherein the substrate is removed after the molding process is complete.

13. The access port as defined in claim 12, wherein the substrate includes flaps or flanges extending from the outer perimeter to facilitate separation of the substrate from the port.

14. A power injectable access port, comprising:
   a port base defining a fluid cavity, the port base formed from a base material;
   a substrate separate from the port base formed from a substrate material, the substrate material being the same as the base material
   a radiopaque material deposited on a surface of the substrate, the radiopaque material including a feature identifying the access port as power injectable,
   wherein the substrate is coupled to the port base such that:
      the radiopaque material is encapsulated between the substrate material and the base material; and
      the feature identifying the access port as power injectable is visible through the substrate prior to implantation.

15. The power injectable access port as defined in claim 14, further comprising a port cap positioned over the port base to capture a septum therebetween.

16. The power injectable access port as defined in claim 14, wherein the radiopaque material comprises a metallic powder intermixed with a marking ink.

17. The power injectable access port as defined in claim 14, wherein the radiopaque material is included on a raised surface of the substrate.

18. The power injectable access port as defined in claim 14, wherein the radiopaque material is deposited on the surface of the substrate via a process selected from the group consisting of pad printing, manual painting, automatic painting, and silk screening.

19. The power injectable access port as defined in claim 14, wherein the substrate has a thickness in the range from about 0.002 inch to about 01015 inch.

* * * * *